United States Patent [19]
Tsugita et al.

[11] Patent Number: 6,046,053
[45] Date of Patent: Apr. 4, 2000

[54] METHOD FOR AMINO ACID SEQUENCING OF PROTEIN OR PEPTIDE FROM CARBOXY TERMINUS THEREOF

[75] Inventors: Akira Tsugita, Kashiwa; Keiji Takamoto, Nagareyama; Tatsuaki Ataka, Chiba; Toshihiko Sakuhara, Chiba; Toyoaki Uchida, Chiba, all of Japan

[73] Assignee: Seiko Instruments Inc., Japan

[21] Appl. No.: 08/862,625

[22] Filed: May 23, 1997

[30] Foreign Application Priority Data

| May 24, 1996 | [JP] | Japan | 8-130381 |
|---|---|---|---|
| Feb. 19, 1997 | [JP] | Japan | 9-035312 |
| Feb. 20, 1997 | [JP] | Japan | 9-036610 |
| Apr. 9, 1997 | [JP] | Japan | 9-091215 |

[51] Int. Cl.[7] ............ G01N 33/50; G01N 33/00
[52] U.S. Cl. .................................. 436/89; 436/90
[58] Field of Search .................................. 436/89, 90

[56] References Cited

U.S. PATENT DOCUMENTS

| 4,548,904 | 10/1985 | Kent et al. | 436/89 |
|---|---|---|---|
| 4,837,165 | 6/1989 | Hawke | 436/89 |
| 4,863,870 | 9/1989 | Stolowitz et al. | 436/89 |
| 4,935,494 | 6/1990 | Miller | 530/345 |
| 5,049,507 | 9/1991 | Hawke et al. | 436/89 |
| 5,051,368 | 9/1991 | Boyd et al. | 436/89 |
| 5,059,540 | 10/1991 | Bailey | 436/89 |
| 5,064,767 | 11/1991 | Le et al. | 436/89 |
| 5,180,807 | 1/1993 | Bailey et al. | 530/345 |
| 5,227,309 | 7/1993 | Bailey et al. | 436/89 |
| 5,246,865 | 9/1993 | Stolowitz | 436/89 |
| 5,468,843 | 11/1995 | Boyd et al. | 530/345 |
| 5,521,097 | 5/1996 | Uchida et al. | 436/86 |
| 5,641,685 | 6/1997 | Anumula | 436/89 |
| 5,665,603 | 9/1997 | Boyd et al. | 436/89 |

FOREIGN PATENT DOCUMENTS

| 217634 | 9/1985 | European Pat. Off. |
|---|---|---|
| 1250863 | 10/1989 | Japan . |
| WO9503066 | 2/1995 | WIPO . |

OTHER PUBLICATIONS

Tsugita et al., Meth. Prot. Seq. Anal., Proc. Int. Conf., 9th, Imahori et al., Eds., Plenum, New York, NY, "Development of Novel C–Terminal Sequencing Methods", pp. 55–62, 1993.

Techniques in Protein Chemistry III, Academic Press, Inc., San Diego, California, (1992), pp. 11–21, Jerome M. Bailey et al., "Automated C–Terminal Sequencing of Peptides".

Biopolymers, vol. 31, John Wiley & Sons, Inc., (1991), pp. 1763–1774, Gautam Basu et al., "Conformational Preferences of Oligopeptides Rich in α–Aminoisobutyric Acid. I. Observation of a $3_{10}$/α–Helical Transition Upon Sequence Permutation".

*Primary Examiner*—Jon P. Weber
*Attorney, Agent, or Firm*—Adams & Wilks

[57] ABSTRACT

A process is disclosed for sequencing proteins or peptides from the C-terminal end. The process comprises the steps of reacting the peptide or protein with an alkyl acid anhydride to convert the carboxy-terminal thereof into oxazolone, liberating the C-terminal amino acid by reaction with acid and alcohol or with ester, and identifying the liberated amino acid or amino acid derivative.

46 Claims, 45 Drawing Sheets

Ac : Acetyl group
Rn : Side chain of amino acids

Ac : Acetyl group
Rn : Side chain of amino acids
R' : Alkyl group

Fig. 37

$H_2NCHR_1CO\cdot\cdot NHCHR_{n-1}CONHCHR_nCOOH$

↓ Acid anhydride

→ [$AcNHCHR_1CO\cdot\cdot NHCHR_{n-1}CONHCHR_nCOOH$]

↓ Acid anhydride $AcNHCHR_1CO\cdot\cdot NHCHR_{n-1}C=N-CHR_n$ (*)
   $\diagdown \quad \diagup$
   $O-CO$ $AcNHCHR_1CO\cdot\cdot NHCHR_{n-1}CONHCHCH_2CO$
   $\diagdown \quad \diagup$
   $OC-O$ ↓ Alcohol (in the presence of acid)

$AcNHCHR_1CO\cdot\cdot NHCHR_{n-1}COOR' + H_2NCHR_nCOOH$ (*)

$AcNHCHR_1CO\cdot\cdot NHCHR_{n-1}CONHCHCOOH$
   $\mid$
   $CH_2COOR'$

↓ Acid anhydride $AcNHCHR_1CO\cdot\cdot NHCHR_{n-1}COOR' + AcNHCHR_nCOOH$ (*)

$AcNHCHR_1CO\cdot\cdot NHCHR_{n-1}C=N-CHCH_2COOR'$
   $\diagdown \quad \diagup$
   $O-CO$ ↓ Alcohol (in the presence of acid)

$AcNHCHR_1CO\cdot\cdot NHCHR_{n-1}COOR' + AcNHCHR_nCOOH$ (*)

$AcNHCHR_1CO\cdot\cdot NHCHR_{n-1}COOR' + H_2NCHCOOH$
   $\mid$
   $CH_2COOR'$

↓ Amine

⎡ $AcNHCHR_1CO\cdot\cdot NHCHR_{n-1}COOH + AcNHCHR_nCOOH$ (*)
⎣ $AcNHCHR_1CO\cdot\cdot NHCHR_{n-1}COOH + H_2NCHCOOH$
   $\mid$
   $CH_2COOH$ Ac : Acetyl group $R_n$ : Side chain of amino acids, R' : Alkyl group

* : when the C-terminal amino acid is not aspartic acid

METHOD FOR AMINO ACID SEQUENCING OF PROTEIN OR PEPTIDE FROM CARBOXY TERMINUS THEREOF

BACKGROUND OF THE INVENTION

The present invention relates to a method for analyzing the primary structure of a protein or a peptide.

In order to determine an amino acid sequence of a protein or a peptide from a carboxy terminus thereof (hereinafter sometimes referred to as a C-terminal), a method, such as that shown in FIG. 3 is used, comprising steps of allowing a protein or a peptide to react with carboxypeptidase, collecting portions of the reaction mixture with the passage of time, analyzing the reaction mixture by an amino acid analyzer, and analyzing the liberated amino acid (Seikagakujikkenkouza Vol.1, Tanpakushitunokagaku II, edited by Nihonseikagakukai, p203–211, 1976).

And, a method for analyzing the mass of a C-terminal truncated protein or a C-terminal truncated peptide by analyzing the reaction mixture using a mass spectrograph is reported (A. Tsugita, R. van den Broek, M. Pyzybylski, FEBS. Lett. 137, 19(1982)). Also, as an example of the chemical methods, a method for analyzing a sequence comprising repeating a series of operations consisting of activating the C-terminal with acetic anhydride, binding trimethylsilylisothiocyanate, and cleaving with hydrochloric acid is reported as shown in FIG. 4 (D. H. Hawke, H-. W. Lahm, J. E. Shively, C. W. Todd, Anal. Biochem. 166, 298(1987)).

The conventional method using carboxypeptidase has difficulty in accurate determination by cleavage at undesirable peptide bonds derived from the diversity of substrate specificity and activity of the enzyme depending upon the C-terminal amino acid or an adjacent amino acid thereof, and from the contamination of the other protease. Also this method is not suitable for microanalysis, since the contamination by the mixture therein of amino acid and peptide occurs because of the reasons that the enzyme has an autolytic property and is unsatisfactorily purified sometimes.

Further, the other chemical method is not sufficiently made to a practical use.

SUMMARY OF THE INVENTION

It is an object of the present invention to provide a chemical method for amino acid sequencing of a protein or a peptide from a C-terminus thereof without using enzymes.

It is another object of the present invention to provide a chemical method which is suitable for microanalysis of amino acid sequencing of a protein or peptide.

BRIEF DESCRIPTION OF THE DRAWINGS

FIG. 37 shows a reaction scheme illustrating another experimental procedure of the present invention;

DETAILED DESCRIPTION OF THE PREFERRED EMBODIMENTS

Figure 1:
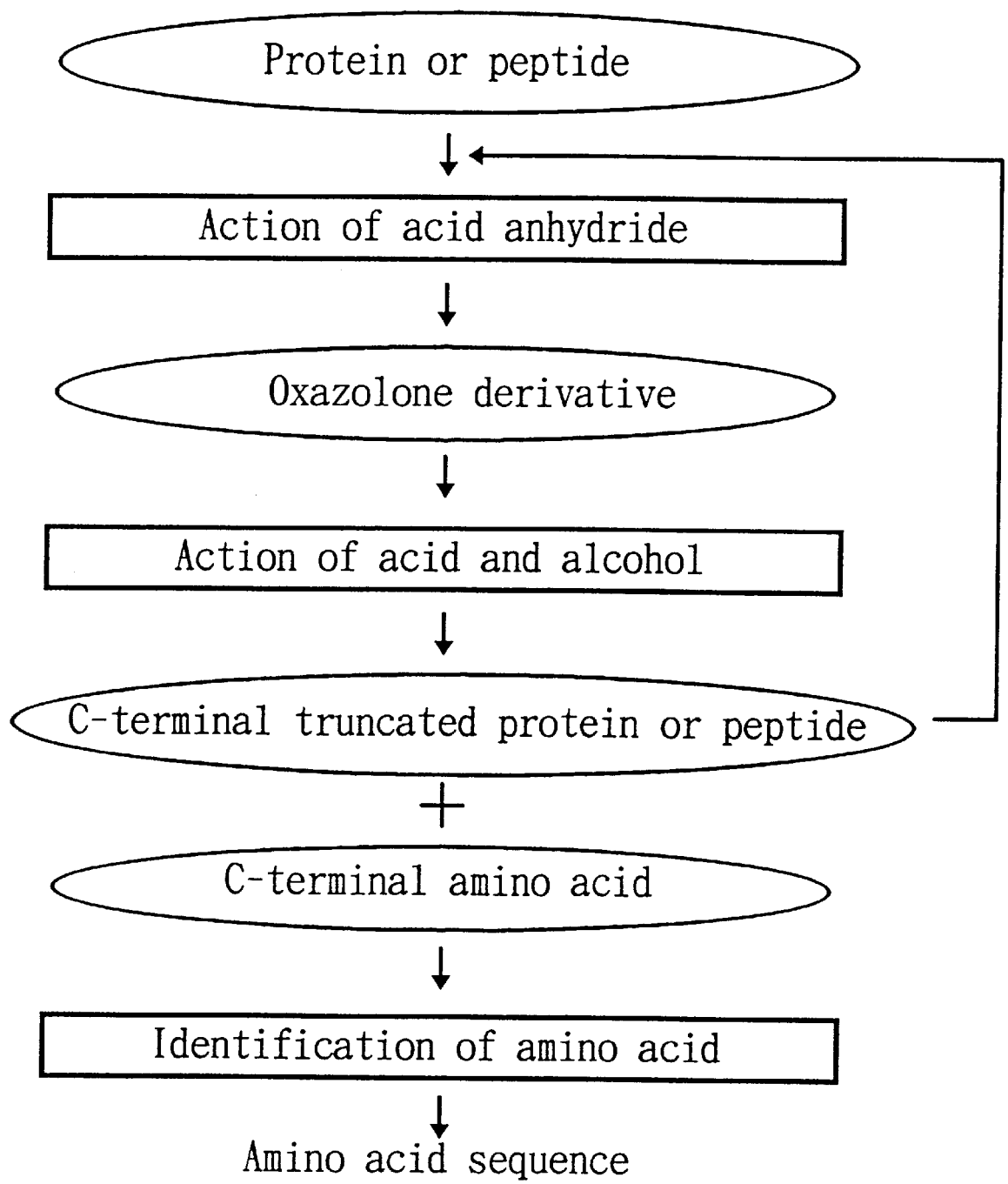
FIG. 1 shows a first flow chart representing a method for analyzing amino acid sequence of the present invention.

As a procedure for carrying out the present invention, a combination is repeated which comprises an operation consisting of a first and a second processes described below and an operation of isolating and identifying amino acid prepared.

First Process

A protein or a peptide is allowed to react with an acid anhydride, an amino terminal of the protein or the peptide is protected, and an amino acid residue at a C-terminal is modified to generate oxazolone.

Second Process

A protein or a peptide generated, whose carboxy terminal is oxazolone, is allowed to react with an acid and alcohol to liberate the carboxy-terminal amino acid.

As another example of the procedure, in order to overcome the problems described above and to sequentially determine an amino acid from a C-terminus thereof, a combination of steps is repeated which comprises a series of operations consisting of the respective first and second processes described above wherein acetic acid is added in the first process and an operation of isolating and identifying the amino acid obtained.

As a further another procedure for carrying out the present invention, a combination is repeated which comprises a series of the operations consisting of the respective processes of a first process to a third process described below and an operation of isolating and identifying an amino acid generated.

First Process

A protein or a peptide is allowed to react with an acid anhydride, an amino group of the protein or the peptide is protected, and an amino acid residue at a C-terminal thereof is modified to generate oxazolone.

Second Process

The reaction product in the first process is allowed to react with an alcohol, the oxazolone contained therein is subjected to alcoholysis (esterification), and the carboxy-terminal amino acid is liberated.

Third Process

The reaction product in the second process is allowed to react with an amine, the ester contained therein is hydrolyzed.

As still another example of the procedure, a combination of steps is repeated which comprises a series of the operations consisting of the respective processes of the first process to the third process described above wherein acetic acid is added in the first process and an operation of isolating and identifying the amino acid generated.

As still another example of the procedure, a combination of steps is repeated which comprises a series of the operations consisting of from the first process to the third described above wherein in the second process the reaction with an alcohol is carried out in the presence of acid and an operation of isolating and identifying the amino acid generated.

As yet another procedure for carrying out the present invention, a combination is repeated which comprises an operation consisting of a first process to a fifth process described below and an operation of isolating and identifying the amino acid or the amino acid derivative generated.

First Process

A protein or a peptide is allowed to react with an acid anhydride, an amino terminal of the protein or the peptide is protected, and an amino acid residue at a C-terminal thereof is modified to generate oxazolone or an intramolecular acid anhydride (when the C-terminal amino acid is aspartic acid).

Second Process

The reaction product in the first process is allowed to react with an alcohol in the presence of acid, the oxazolone contained therein is subjected to alcoholysis (esterification), and the carboxy-terminal amino acid is liberated or the intramolecular acid anhydride is ring-opened by alcoholysis.

Third Process

The reaction product in the second process is allowed to react with an acid anhydride, the amino acid residue at the C-terminus of the protein or the peptide, whose C-terminal is not esterified, contained therein is modified to generate oxazolone.

Fourth Process

The reaction product in the third process is allowed to react with an alcohol in the presence of acid, the oxazolone contained therein is subjected to alcoholysis (esterification), and the carboxy-terminal amino acid is liberated.

Fifth Process

The reaction product in the fourth process is allowed to react with an amine and the ester contained therein is hydrolyzed.

As still further another example of the procedure, a combination is repeated which comprises a series of the operations consisting of from the first process to the third described above wherein the acid anhydride is changed for an ester of a halogenated formic acid in the first process and an operation of isolating and identifying the amino acid or the amino acid derivative generated.

As yet further another example of the procedure above, a combination is repeated which comprises a series of the operations consisting of the respective processes of the first process to the third process described above wherein the second and fourth processes to react with an alcohol are carried out in the presence of acid and an operation of isolating and identifying the amino acid or the amino acid derivative generated.

The present invention will be further described with reference to the following examples.

EXAMPLE 1

FIG. 1 shows a flow chart illustrating the present invention.

First Process

A protein or a peptide is allowed to react with an anhydride of an organic acid represented by the general formula;

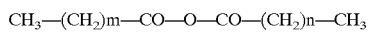
$CH_3-(CH_2)m-CO-O-CO-(CH_2)n-CH_3$ (m and n is an integer of 0 or above, respectively) to give a protein or a peptide whose amino group is modified and C-terminal amino acid converted into oxazolone.

Second Process

Subsequently, the protein or the peptide, whose amino group is modified and C-terminal amino acid is converted into oxazolone, is allowed to react with an acid and alcohol to give a mixture of a protein or a peptide whose amino group is modified and one amino acid residue at the C-terminus is lacking and the original C-terminal amino acid.

The amino acid obtained thereby is isolated and identified to determine the C-terminal amino acid of the protein or the peptide.

Then the operations of the first and second processes using the protein or the peptide whose amino group is modified and one amino acid residue at the C-terminus is lacking, and the operation of isolating and identifying the amino acid obtained are repeatedly carried out to analyze the amino acid sequence of the protein or the peptide from the C-terminus.

EXAMPLE 2

Here, an example of the operation procedure of the present invention is described which analyzes an amino acid sequence of a protein or a peptide from a C-terminus thereof by repeating operations of the first and second processes using a protein or a peptide and an operation of isolating and identifying the amino acid from the mixture obtained in the second process.

Figure 2:
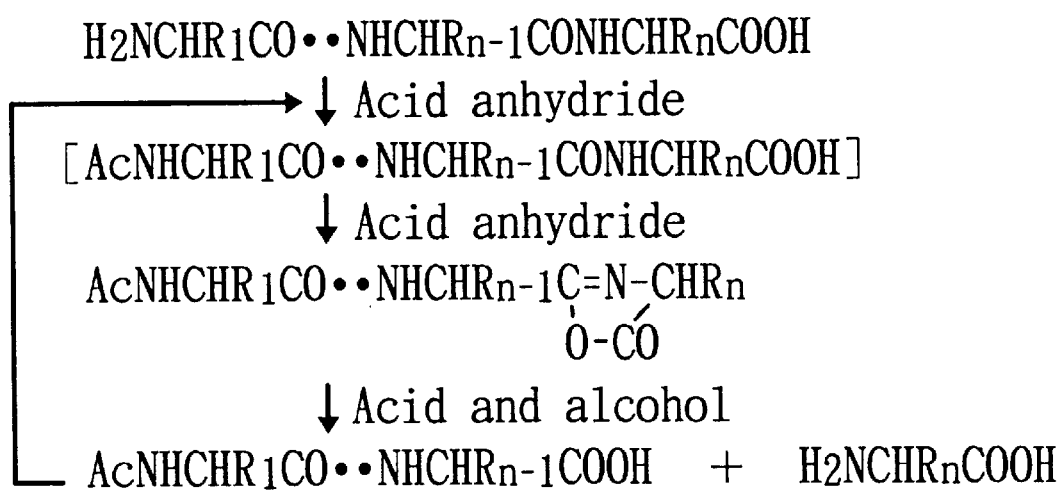
FIG. 2 shows a reaction scheme illustrating an experimental procedure of the present invention.
Figure 3:
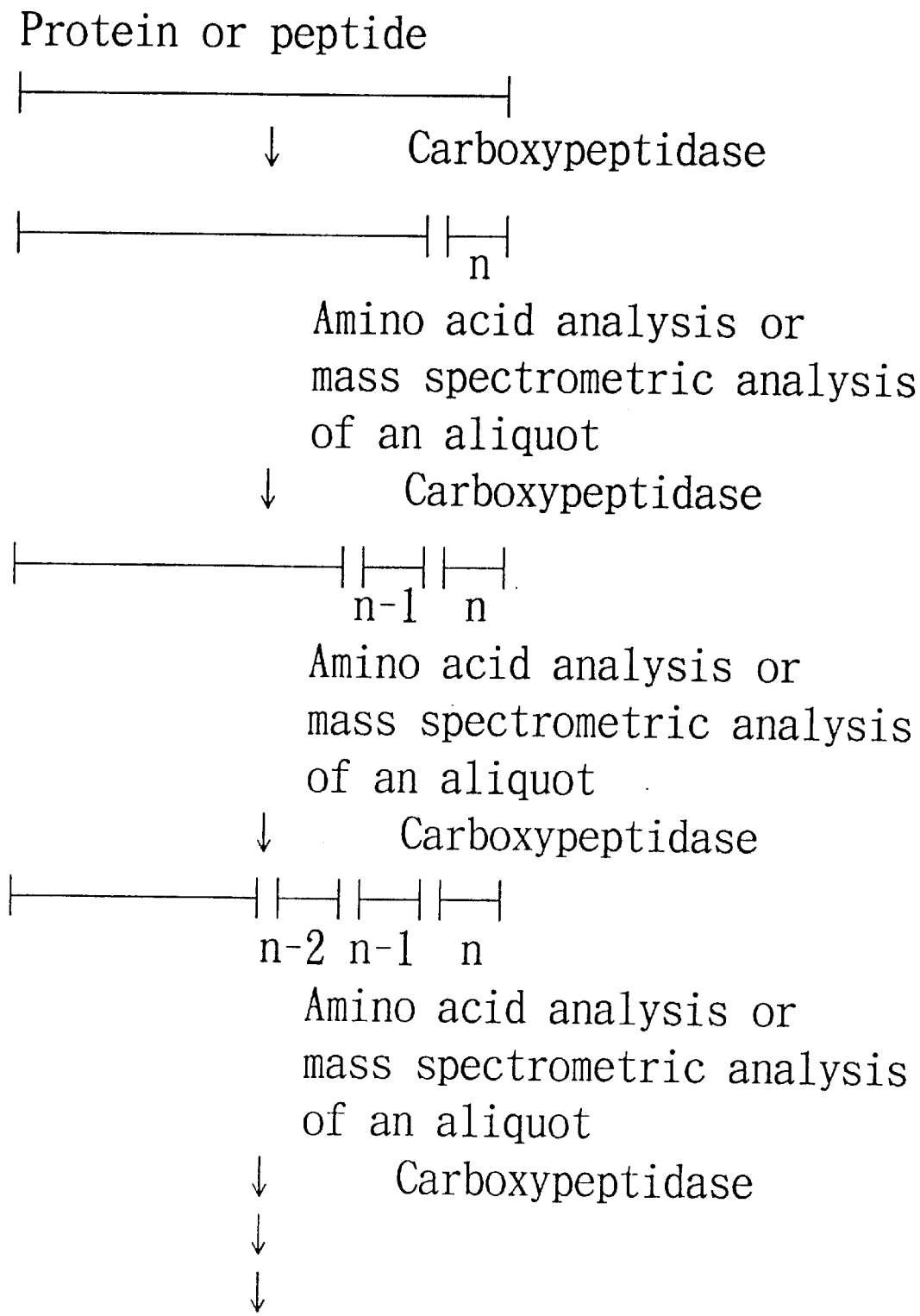
FIG. 3 shows a flow chart representing a conventional determination method using carboxypeptidase.
Figure 4:
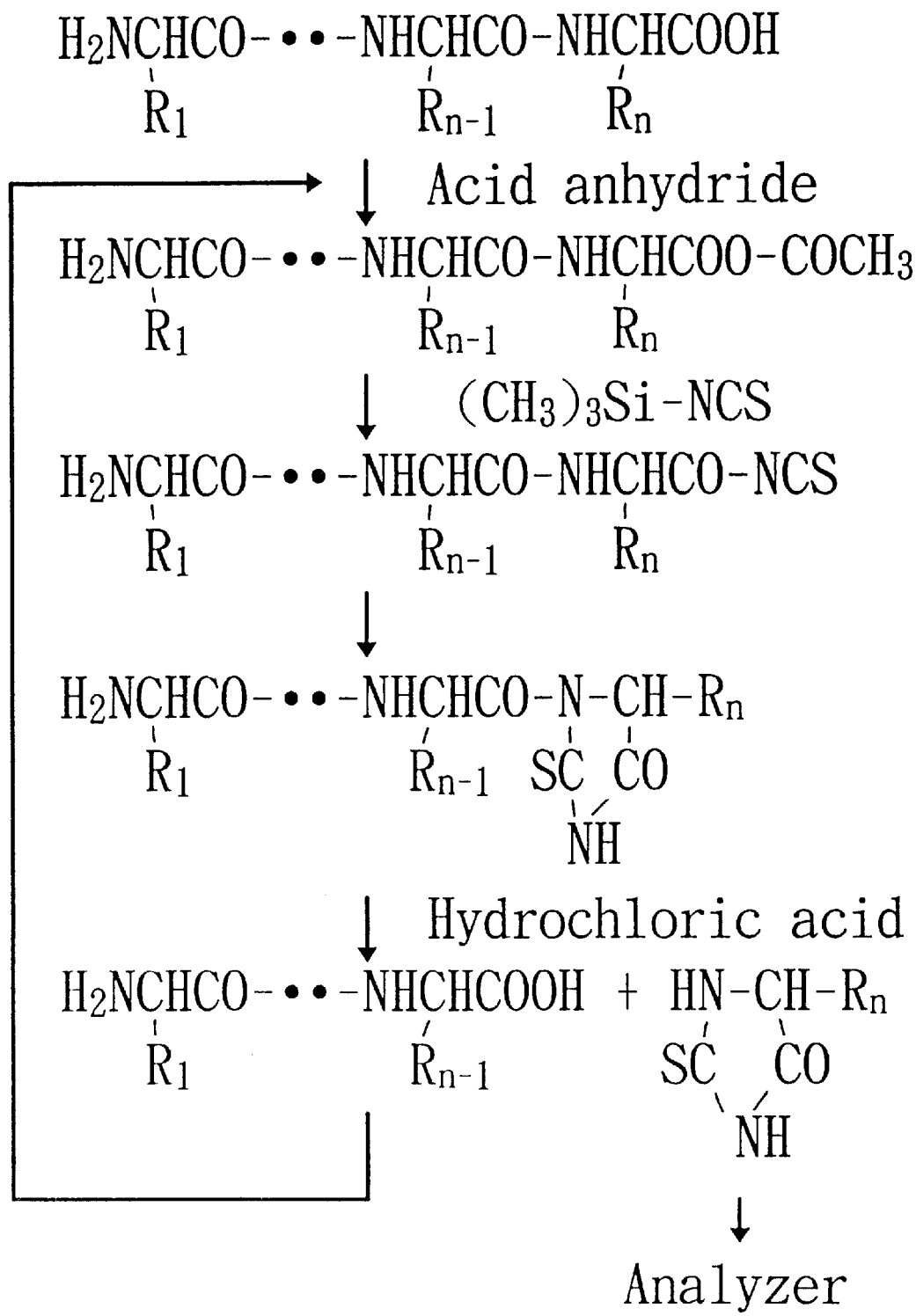
FIG. 4 shows a flow chart representing a conventional determination method using trimethylsilylisothiocyanate.

FIG. 2 shows a reaction scheme illustrating the experimental procedure of the present invention.

First Process

A sample is allowed to react with acetic anhydride. The reaction conditions are as follows.

Reaction conditions

Concentration of acetic anhydride: 20% (acetonitrile solution, acetic acid added to adjust to 1% of the concentration)

Reaction temperature: 60° C.

Reaction period: 30 minutes

After this reaction, the reaction mixture is evaporated under reduced pressure to dryness to remove the reagent and solvent.

Second Process

The sample obtained is allowed to react with pentafluoropropionic acid (PFPA) and methanol. The reaction conditions are as follows.

Reaction conditions

Concentration of PFPA: 50% (methanol solution)

Reaction temperature: 60° C.

Reaction period: 30 minutes

Under these conditions, an ester, methylpentafluoropropionate is generated by the reaction of PFPA with methanol.

Then the reaction mixture is evaporated under reduced pressure to dryness to remove the reagent and solvent.

After the second process, the amino acid is isolated from the sample obtained and identified.

Then a combination of the procedures consisting of the first and second processes using the protein or the peptide whose amino group is modified and one amino acid residue at the C-terminus is lacking and the operation of isolating and identifying the amino acid obtained in the second process is repeatedly carried out to analyze the amino acid sequence of the protein or the peptide from the C-terminus.

EXAMPLE 3

Here, the conditions for analysis by high precision liquid chromatography (hereinafter referred to as HPLC) describing the present invention and the results of analyzing standard compounds by HPLC are described.

The conditions for the HPLC analysis are as follows.

Analysis conditions

Column: Shiseido C18 MICROBORE

Elution: Gradient elution with the following solution A and B

Solution A: 0.1% TFA aqueous solution

Solution B: 80% acetonitrile aqueous solution containing 0.1% TFA

TABLE 1

| Retention Time | Composition of Eluent | Flow Rate (ml/min) |
| --- | --- | --- |
| 0–5 min | Solution A, 100% | 0.15 |
| 5–30 min | Solution A, 100→0% (linear gradient) | 0.15 |
| 30–35 min | Solution A, 0% | 0.15 |
| 35–36 min | Solution A, 0→100% (linear gradient) | 0.15→0.30 |
| 36–44 min | Solution A, 100% | 0.30 |
| 44–45 min | Solution A, 100% | 0.30→0.15 |

Detection: Absorption at 280 nm

Figure 5:
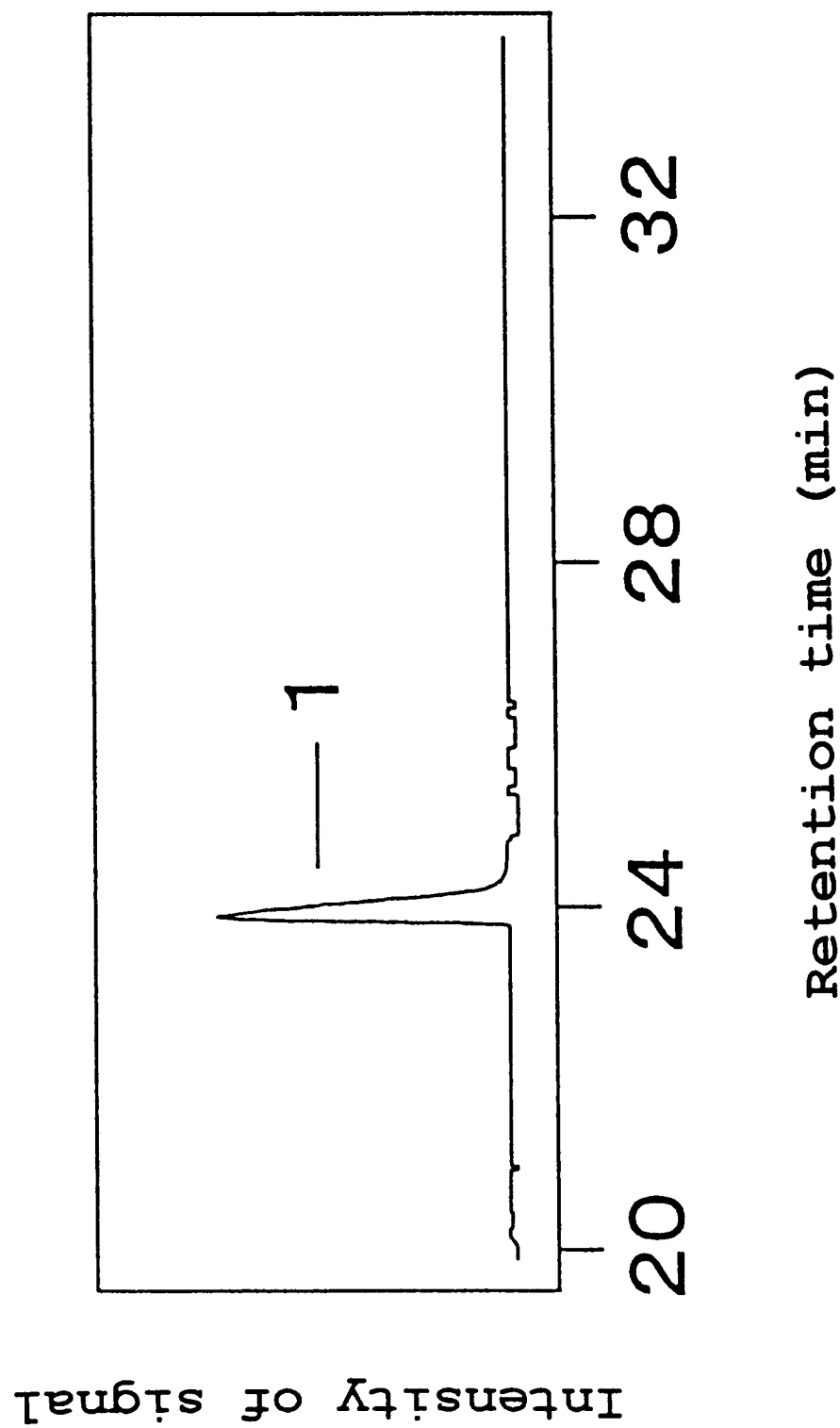
FIG. 5 shows a drawing showing a result of HPLC analysis to confirm the retention time of alanyltryptophan.
Figure 6:
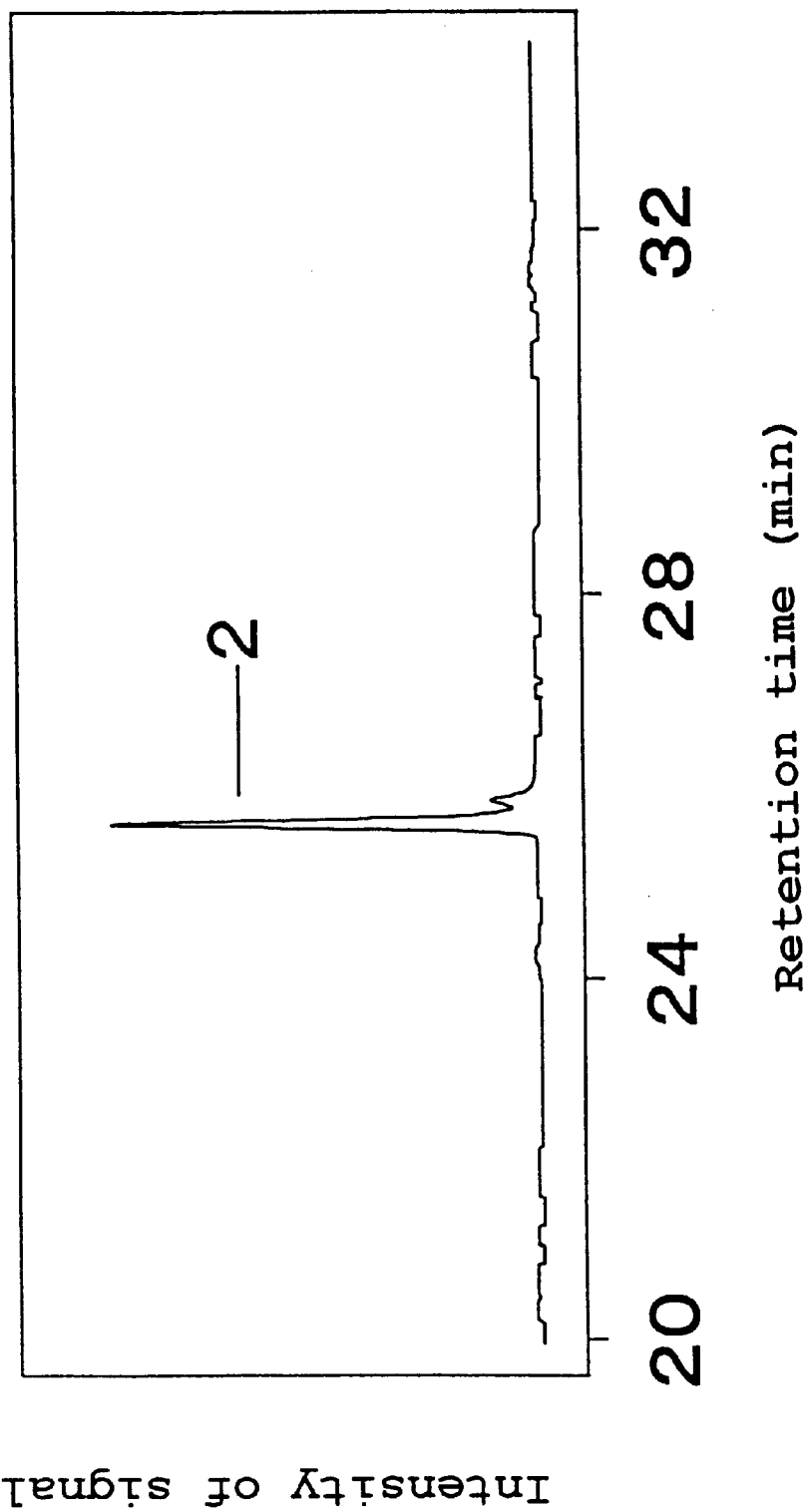
FIG. 6 shows a drawing showing a result of HPLC analysis to confirm the retention time of N-acetylalanyltryptophan.
Figure 7:
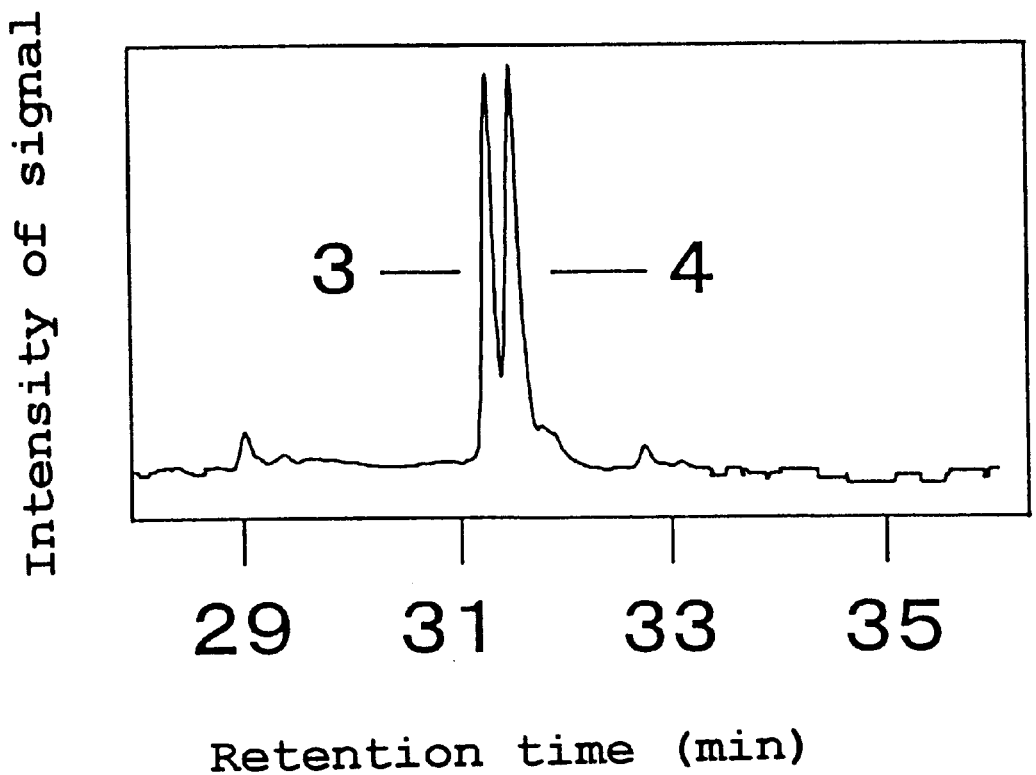
FIG. 7 shows a drawing showing a result of HPLC analysis to confirm the retention time of N-acetylalanyltryptophanylmethionylarginylphenylalanine.
Figure 8:
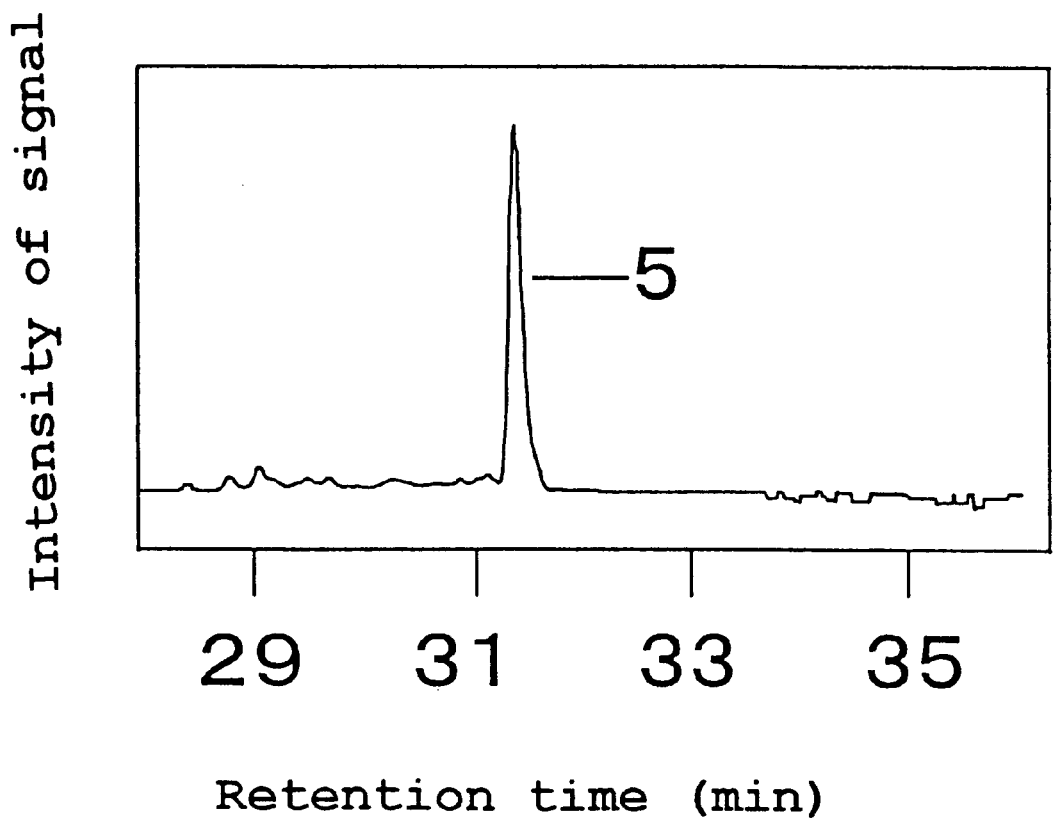
FIG. 8 shows a drawing showing a result of HPLC analysis to confirm the retention time of N-acetylalanyltryptophanylmethionylarginylphenylalanylalanine.

The standard compounds analyzed under these conditions are as described below. The results of analysis will be shown in the figures as follows, respectively. FIG. 5 shows a result of HPLC analysis of alanyltryptophan (Ala-Trp). In the figure, numeral 1 shows a peak corresponding to alanyltryptophan. FIG. 6 shows a result of HPLC analysis of N-acetylalanyltryptophan (Ac-Ala-Trp). In the figure, numeral 2 shows a peak corresponding to N-acetylalanyltryptophan. FIG. 7 shows a result of HPLC analysis of sequence No. 1 ("SEQ ID NO: 1") N-acetylalanyl-tryptophanyl-methionyl-arginyl-phenylalanine (Ac-Ala-Trp-Met-Arg-Phe). In the figure, numeral 3 shows a peak corresponding to N-acetylalanyltryptophanylmethionylarginylphenylalanine and numeral 4 shows a peak corresponding to N-acetylalanyltryptophanylmethionylarginylphenylalanine. FIG. 8 shows a result of HPLC analysis analysis of sequence No. 2 ("SEQ ID NO: 2") N-acetylalanyl-tryptophanyl-methionyl-arginyl-phenylalanyl-alanine (Ac-Ala-Trp-Met-Arg-Phe-Ala). In the figure, numeral 5 shows a peak corresponding to N-acetylalanyl tryptophanyl-methionylarginylphenylalanylalanine In FIG. 7, two peaks corresponding to N-acetylalanyl-tryptophanyl-methionyl-arginyl-phenylalanine are observed. They are isomers.

EXAMPLE 4

Figure 9:
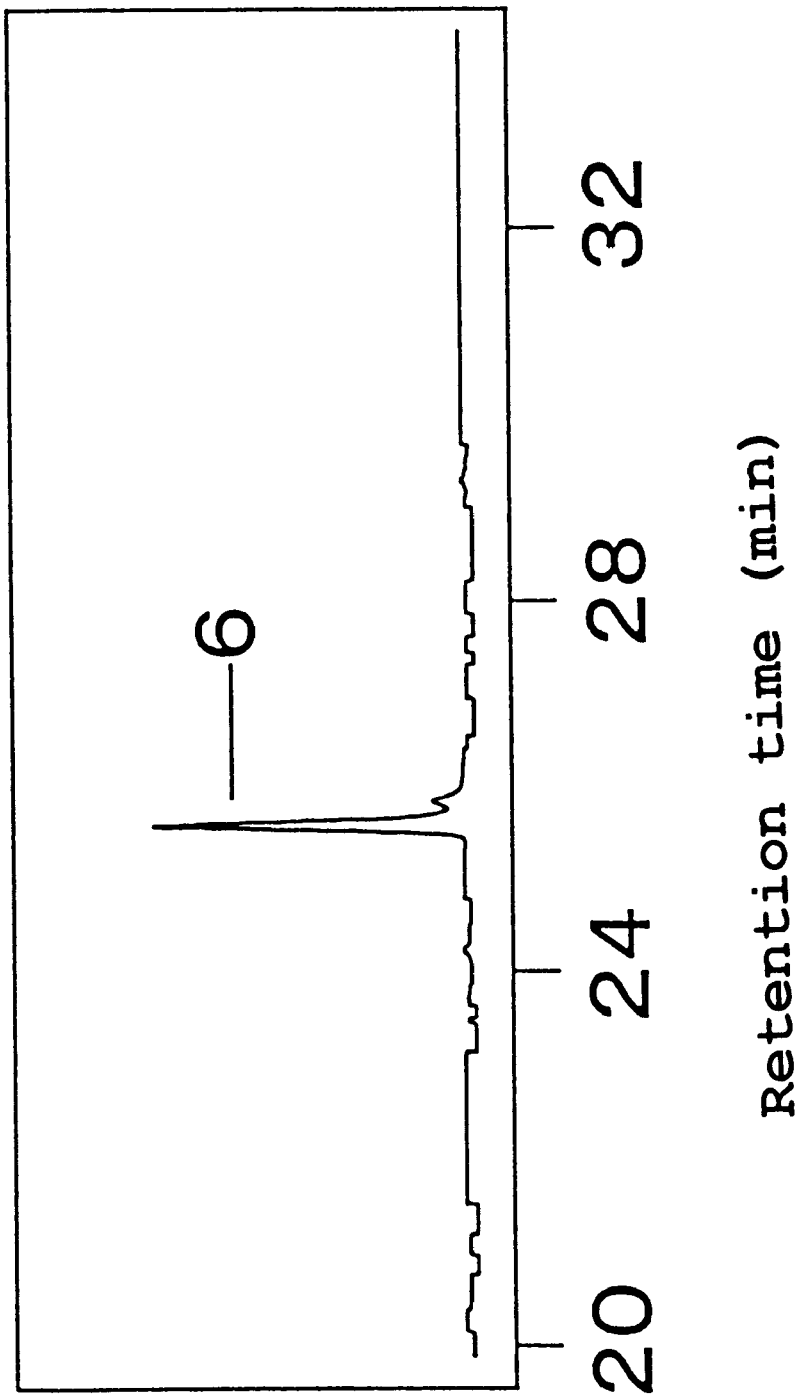
FIG. 9 shows a drawing showing a result of HPLC analysis to confirm generation of oxazolone.

Here, generation of oxazolone under the conditions for the operation of the first process is described. As the sample, alanyltryptophan (Ala-Trp) was used. The oxazolone was detected using the cleavage reaction easily caused by water. Detection was carried out by HPLC. FIG. 9 shows a result of HPLC analysis analysis of the reaction product obtained by allowing the sample obtained in the first process to react with water. The conditions for HPLC analysis analysis are as described in Example 3.

The procedure of preparing the sample for HPLC analysis is as follows.

(1) Evaporate the sample under reduced pressure to dryness.

(2) Dissolve the residue in 0.1% trifluoroacetic acid (referred to as TFA)

Compared with FIG. 7, N-acetylalanyltryptophan (Ac-Ala-Trp) 6 was detected in FIG. 9, this indicates generation of oxazolone in the first process. Here, alanyltryptophan used as the sample was not detected.

EXAMPLE 5

Here, cleavage of oxazolone under the conditions for the operation of the second process is described. As the sample, SEQ ID NO: 2N-acetylalanyltryptophanylmethionyl- arginylphenylalanylalanine (Ac-Ala-Trp-Met-Arg-Phe-Ala) was used. Detection was carried out by HPLC analysis under the same conditions as in Example 4. The procedure of preparing the sample for HPLC analysis was as described in Example 4.

Figure 10:
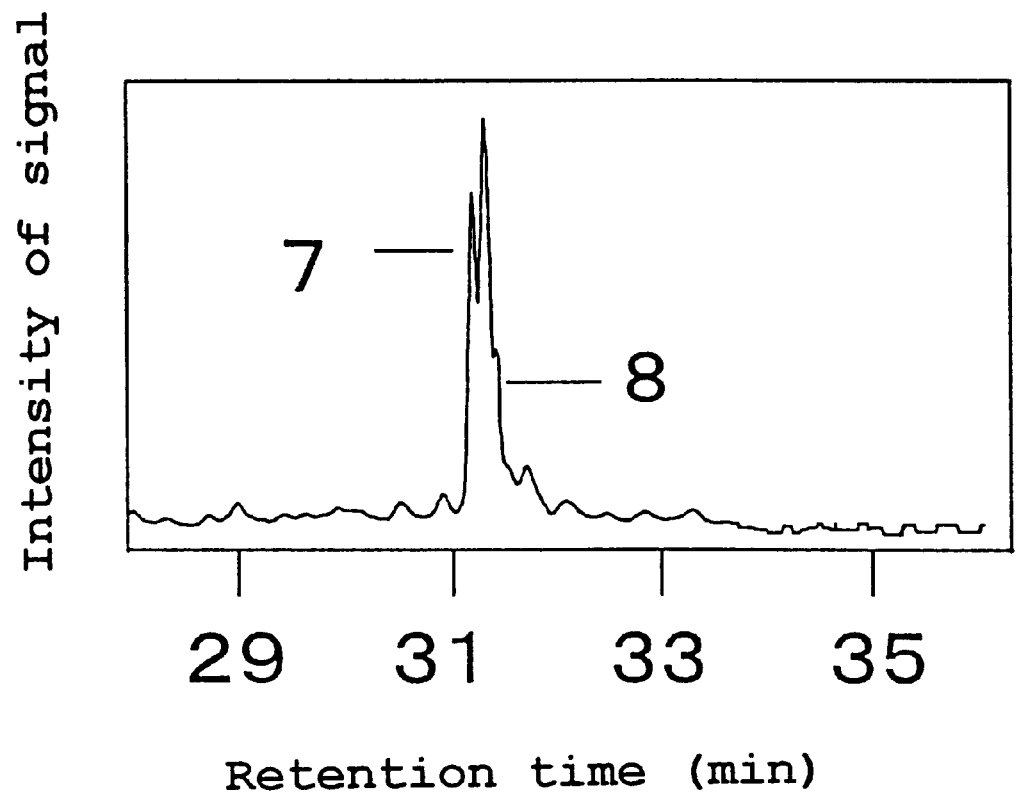
FIG. 10 shows a drawing showing a result of HPLC analysis to confirm cleavage of the oxazolone ring.

FIG. 10 shows a result of analyzing the reaction product obtained in the second process described in Example 2. Compared with FIG. 7, SEQ ID NO: 1 N-acetylalanyltryptophanylmethionylarginylphenylalanine (Ac-Ala-Trp-Met-Arg-Phe), denoted by reference numerals 7 and 8, which is a product lacking the C-terminal amino acid, alanine, of SEQ ID NO: 2 N-acetylalanyltryptophanylmethionylarginylphenylalanyl-alanine (Ac-Ala-Trp-Met-Arg-Phe-Ala) used as the sample was detected in FIG. 10. This indicates cleavage of the oxazolone ring under the conditions for the second process, liberaton of the C-terminal amino acid, and generation of the peptide lacking the C-terminal amino acid (having acetylated amino terminal). This C-terminal amino acid is identified to determine the C-terminal of the peptide.

Then, a combination of the operations consisting of the first and second processes using the peptide lacking the C-terminal amino acid (having acetylated amino terminal) and the operation of isolating and identifying the amino acid obtained is repeatedly carried out to analyze the amino acid sequence of the protein or the peptide used from the C-terminus.

Accordingly, the results of Example 1 to 5 are summarized as follows.

In the present invention, in order to analyze the amino acid sequence from the C-terminus, a combination of the operations consisting of the following first and second processes and the operation of isolating and identifying the amino acid obtained was repeatedly carried out.

First Process

A protein or a peptide is allowed to react with an acid anhydride, the amino terminal of the protein or the peptide is protected, and the amino acid residue at the C-terminus is modified to generate oxazolone.

Second Process

The protein or the peptide generated, whose carboxy terminal is oxazolone, is allowed to react with an acid and alcohol to liberate the carboxy-terminal amino acid.

Hereinafter another procedure for carrying out the present invention will be further described.

EXAMPLE 6

Figure 11:
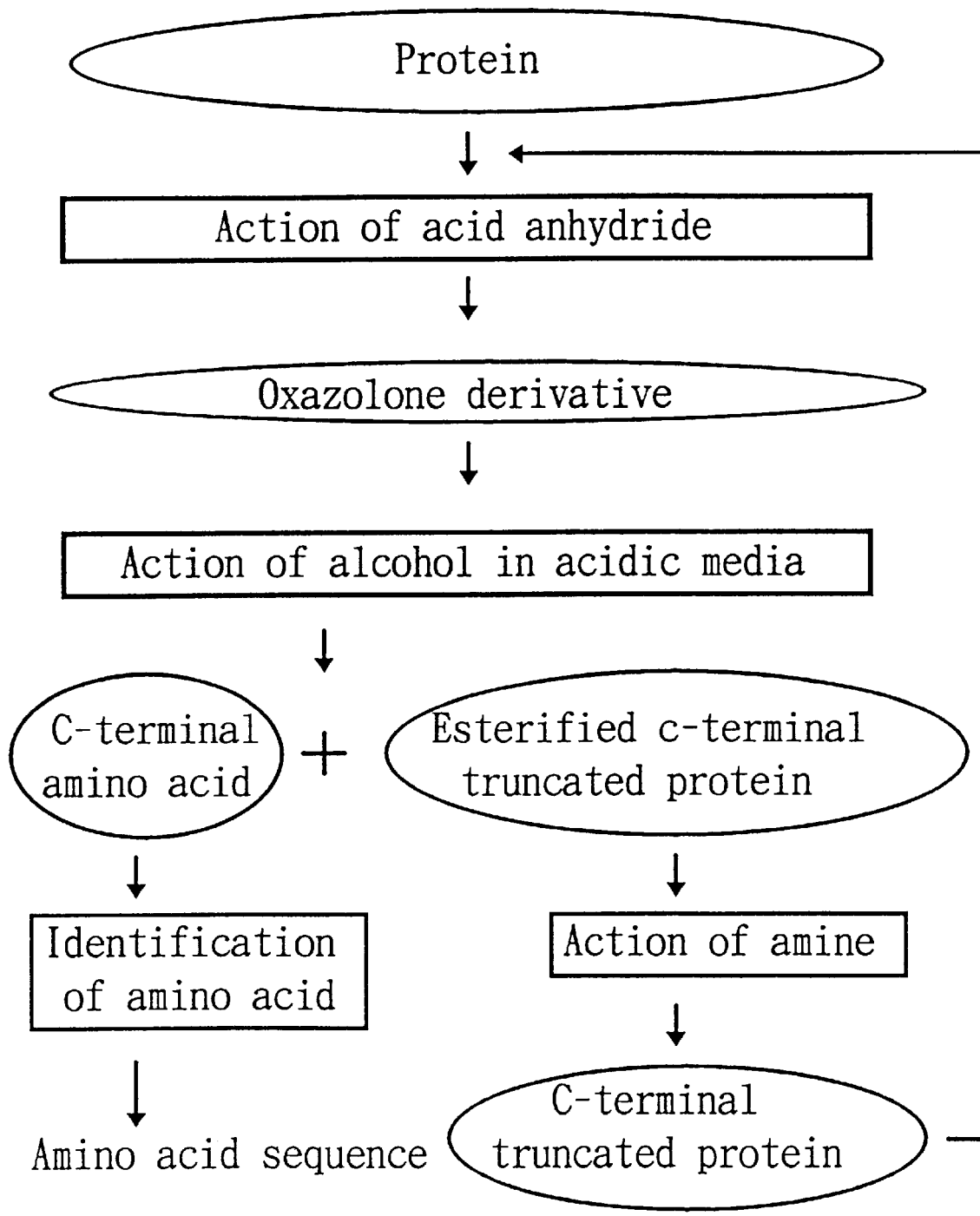
FIG. 11 shows a second flow chart representing a method for analyzing amino acid sequence of the present invention.

FIG. 11 shows a flow chart illustrating the present invention.

First Process

A protein or a peptide is allowed to react with an anhydride of an organic acid represented by the general formula;

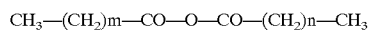

(m and n is an integer of 0 or above, respectively) to give a protein or a peptide whose amino group is modified and C-terminal amino acid is converted into oxazolone.

Second Process

Then, the protein or the peptide, whose amino group is modified and C-terminal amino acid is converted into oxazolone,is allowed to react with an alcohol in the presence of acid to give a mixture of a protein or a peptide newly generated whose amino group is modified, the C-terminal amino acid is lacking, and the carboxy group of the C-terminal amino acid is esterified and the original C-terminal amino acid.

Third Process

The mixture of the protein or the peptide newly generated, whose amino group is modified, C-terminal amino acid is lacking, and carboxy group of the C-terminal amino acid is esterified, and the amino acid is allowed to react with an aqueous solution of an amine, for instance an amine represented by a general formula;

NR1R2R3, to give a mixture of a protein or a peptide of which the amino group is modified and the C-terminal amino acid is lacking and the amino acid.

The amino acid obtained in the first to third processes described above is isolated and identified to determine the C-terminal amino acid of the protein or the peptide.

Then a series of the operations of the first to third processes using the protein or the peptide, whose amino group is modified and the C-terminal amino acid is lacking, and the operation of isolating and identifying the amino acid obtained are repeatedly carried out to analyze the amino acid sequence of the protein or the peptide from the C-terminus.

EXAMPLE 7

Here, an example of the operation procedure of the present invention is described which analyzes an amino acid sequence of a protein or a peptide from a C-terminus thereof by repeating a series of the operations of the first to third processes using a protein or a peptide and an operation of isolating and identifying the amino acid from the mixture obtained in the second process.

Figure 12:
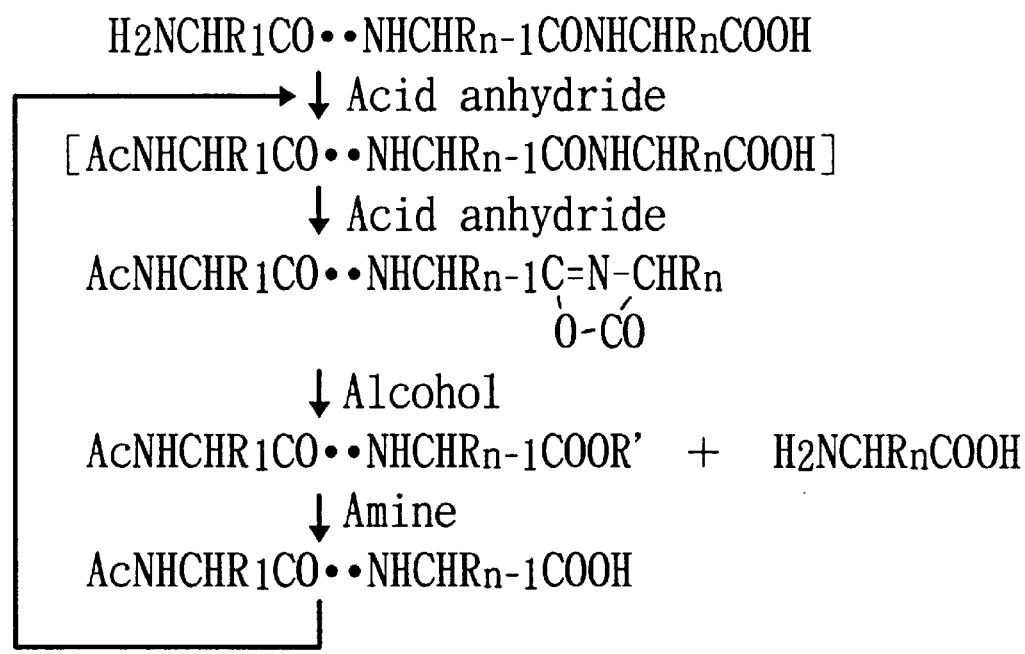
FIG. 12 shows a reaction scheme illustrating another experimental procedure of the present invention.

FIG. 12 shows an example of a reaction scheme illustrating an experimental procedure of the present invention.

First Process

A sample is allowed to react with acetic anhydride. An example of the reaction conditions is as follows.

Reaction conditions

Concentration of acetic anhydride: 20% (acetonitrile solution, acetic acid added to adjust to 1% of the concentration)

Reaction temperature: 60° C.

Reaction period: 30 minutes

After this reaction, the reaction mixture is evaporated under reduced pressure to dryness to remove the reagent and solvent.

Second Process

The sample obtained thereby is allowed to react with methanol in the presence of pentafluoropropionic acid ($CF_3$—$CF_2$—COOH: hereinafter referred to as PFPA) 1. An example of the reaction conditions is as follows.

Reaction conditions

Concentration of PFPA: 10% (methanol solution)

Reaction temperature: 60° C.

Reaction period: 30 minutes

After this reaction, the reaction mixture is evaporated under reduced pressure to dryness to remove the reagent and solvent.

Third Process

The sample obtained thereby is allowed to react with 2-dimethylaminoethanol (hereinafter referred to as DMAE). The reaction conditions are as follows.

Reaction conditions

Concentration of DMAE: 10% (aqueous solution)

Reaction temperature: 60° C.

Reaction period: 30 minutes

In a series of these operations, after the second process, the amino acid is isolated from the sample obtained and identified.

Then, the combination of a series of the procedures of the first to third processes using the protein or the peptide, whose amino group is modified and the C-terminal amino acid is lacking, and the operation of isolating and identifying the amino acid obtained in the second process is repeatedly carried out to analyze the amino acid sequence of the protein or the peptide from the C-terminus.

EXAMPLE 8

Here, an example of the operation procedure of the present invention is described which analyzes an amino acid sequence of a protein or a peptide from a C-terminus thereof by repeating a combination of a series of the operations of the first to third processes using a protein or a peptide and an operation of isolating and identifying the amino acid from the mixture obtained in the third process.

A series of the operations of the first to third processes is the same as described in Example 7. In a series of these operations, after the third process, the amino acid is isolated from the sample obtained and identified.

Then, a series of the procedures of the first to third processes using the protein or the peptide, whose amino group is modified and the C-terminal amino acid is lacking, and the operation of isolating and identifying the amino acid obtained in the third process are repeatedly carried out to analyze the amino acid sequence of the protein or the peptide from the C-terminus.

EXAMPLE 9

Here, the conditions for HPLC analysis analysis describing the present invention and the results of analyzing standard compounds by HPLC are described.

The conditions for the HPLC analysis were as follows.

Analysis conditions

Column: Shiseido C18 MICROBORE

Elution: Gradient elution with the following solution A and B

Solution A: 0.1% TFA aqueous solution

Solution B: 80% acetonitrile aqueous solution containing 0.1% TFA

TABLE 2

| Retention Time | Composition of Eluent | Flow Rate (ml/min) |
| --- | --- | --- |
| 0–5 min | Solution A, 100% | 0.15 |
| 5–30 min | Solution A, 100→0% (linear gradient) | 0.15 |
| 30–35 min | Solution A, 0% | 0.15 |
| 35–36 min | Solution A, 0→100% (linear gradient) | 0.15→.30 |
| 36–44 min | Solution A, 100% | 0.30 |
| 44–45 min | Solution A, 100% | 0.30→0.15 |

Detection: Absorption at 280 nm

Figure 13:
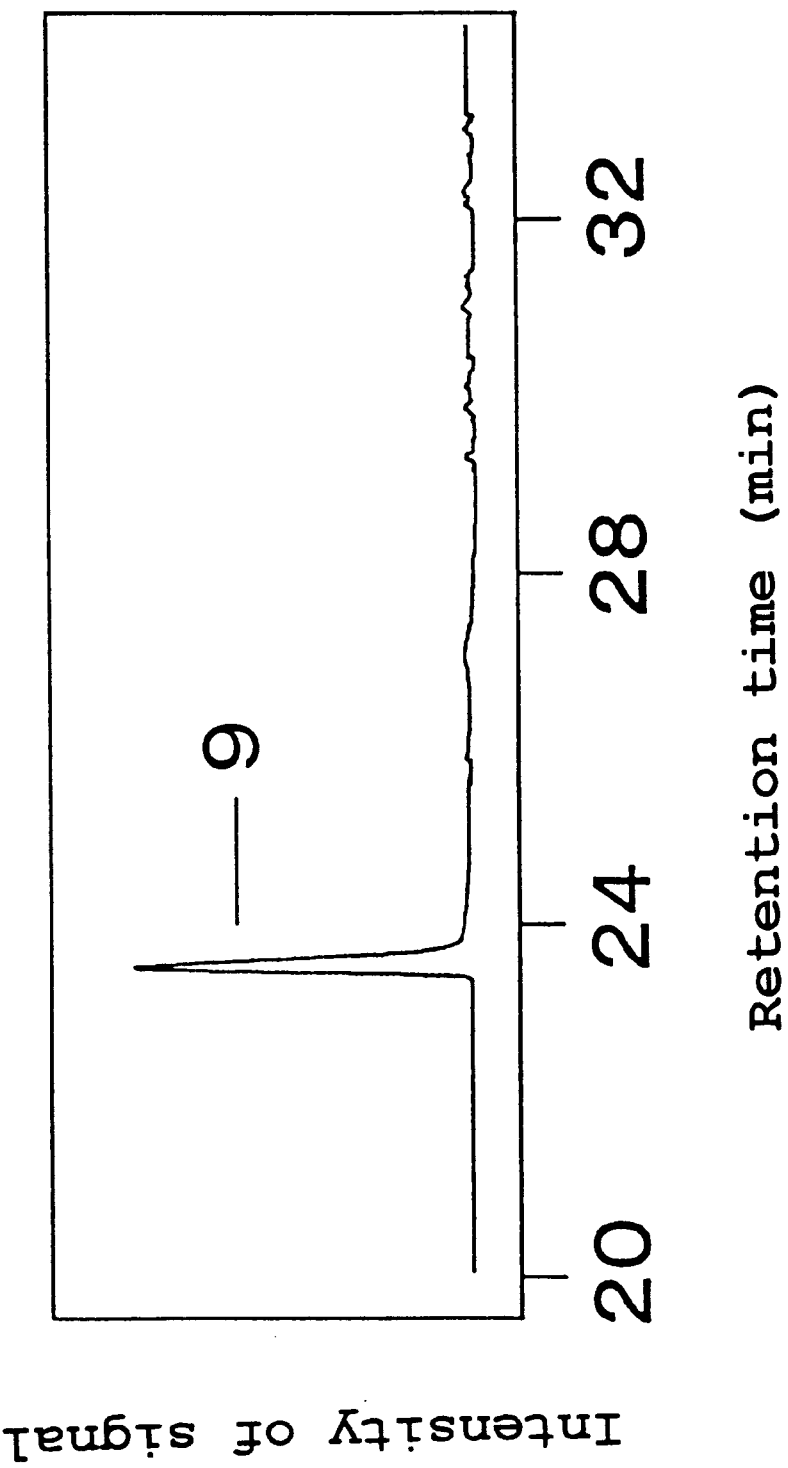
FIG. 13 shows a drawing showing a result of HPLC analysis to confirm the retention time of tryptophan.
Figure 14:
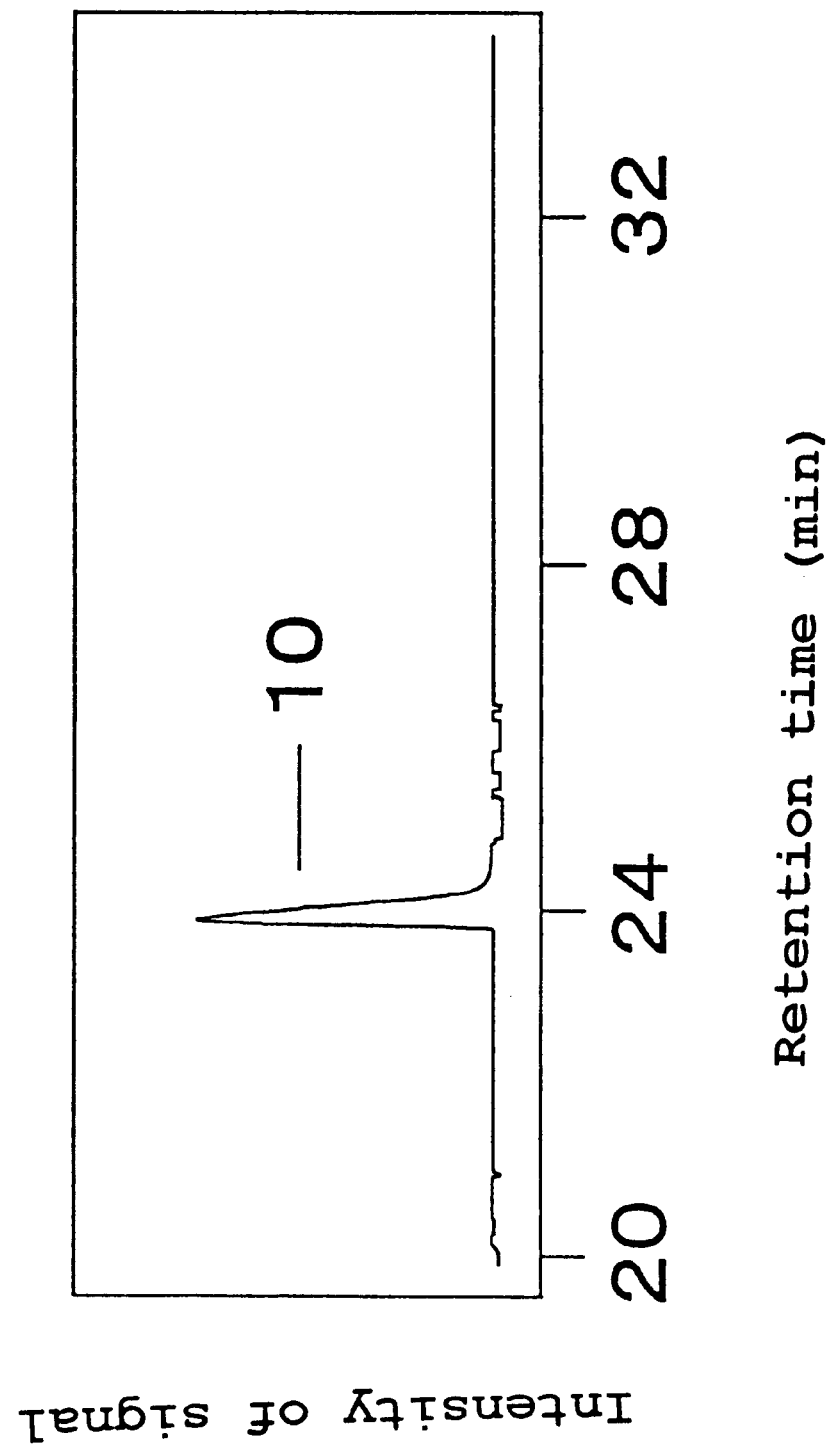
FIG. 14 shows a drawing showing a result of HPLC analysis to confirm the retention time of alanyltryptophan.
Figure 15:
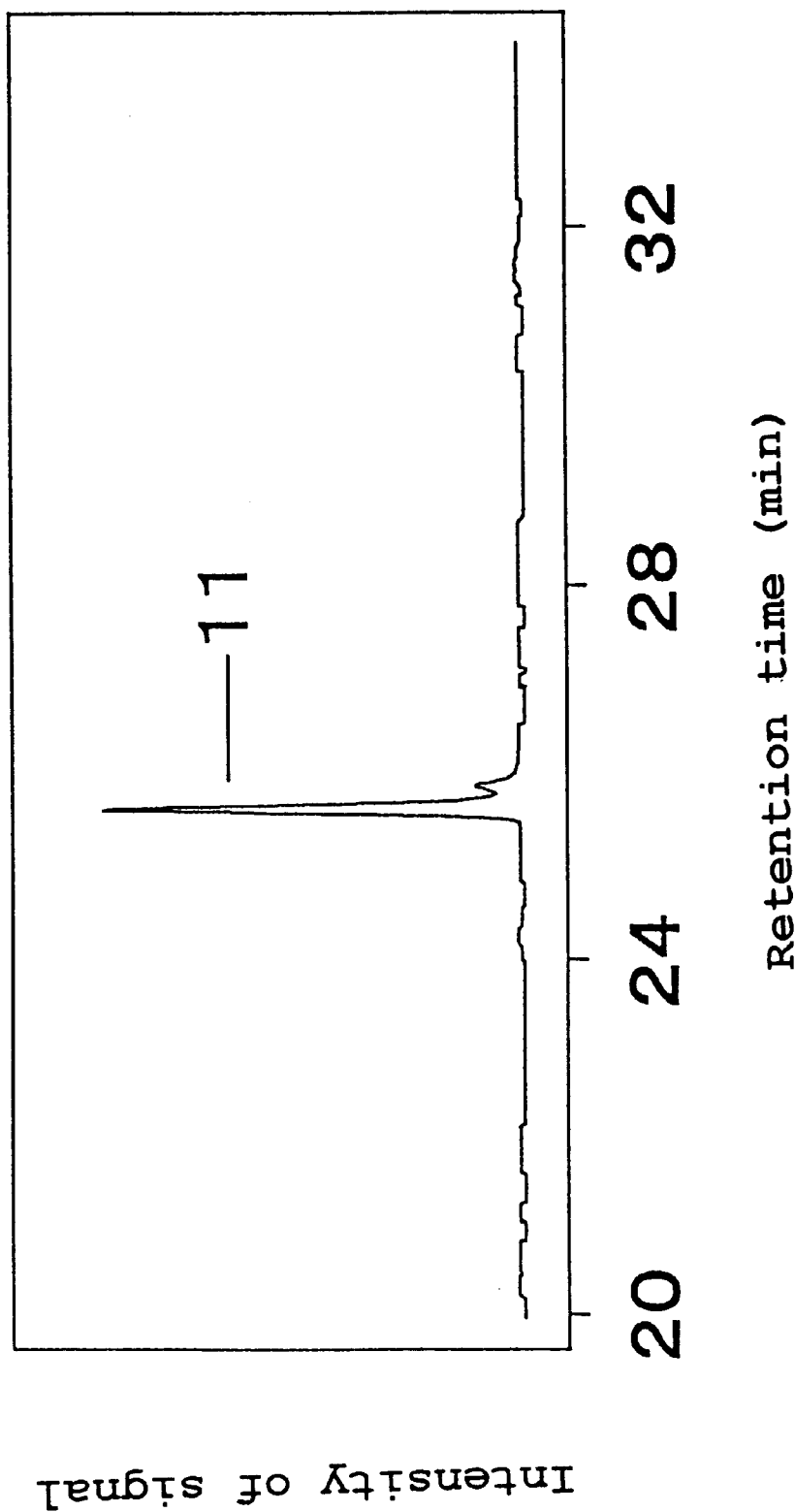
FIG. 15 shows a drawing showing a result of HPLC analysis to confirm the retention time of N-acetylalanyltryptophan.
Figure 16:
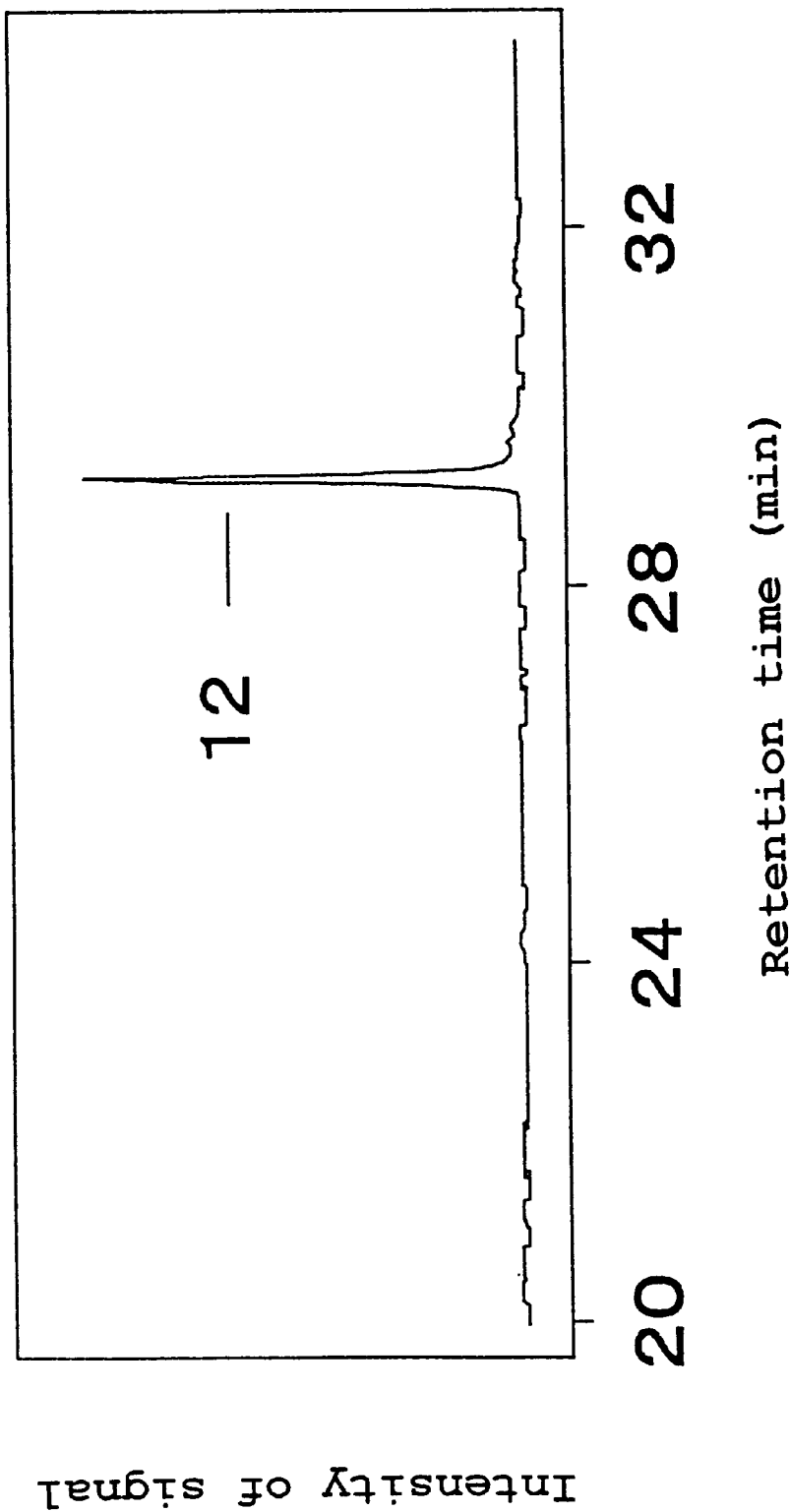
FIG. 16 shows a drawing showing a result of HPLC analysis to confirm the retention time of the ethyl ester of N-acetylalanyltryptophan.

The standard compounds analyzed under these conditions are as described below. The results of analysis will be shown in the figures as follows, respectively. FIG. 13 shows the result of HPLC analysis analysis of tryptophan (Trp). In the figure, numeral 9 shows a peak corresponding to tryptophan. FIG. 14 shows that of alanyltryptophan (Ala-Trp). In the figure, numeral 10 shows a peak corresponding to alanyltryptophan. FIG. 15 shows that of N-acetylalanyltryptophan (Ac-Ala-Trp). In the figure, numeral 11 shows a peak corresponding to N-acetylalanyltryptophan. FIG. 16 shows that of the ethyl ester of N-acetylalanyltryptophan (Ac-Ala-Trp-OEt). In the figure, numeral 12 shows a peak corresponding to the ethylester of N-acetylalanyltryptophan.

EXAMPLE 10

Here, generation of oxazolone under the conditions in the operation of the first process is described. As the sample, alanyltryptophan (Ala-Trp) was used. The oxazolone was detected using the cleavage reaction easily caused by water. Detection was carried out by HPLC analysis. FIG. 9 shows the result of HPLC analysis of the reaction product obtained by allowing the sample obtained in the first process to react with water. The conditions for HPLC analysis are as described in Example 9.

The procedure of preparing the sample for HPLC analysis is as follows.

(1) Evaporate the sample under reduced pressure to dryness.

Figure 17:
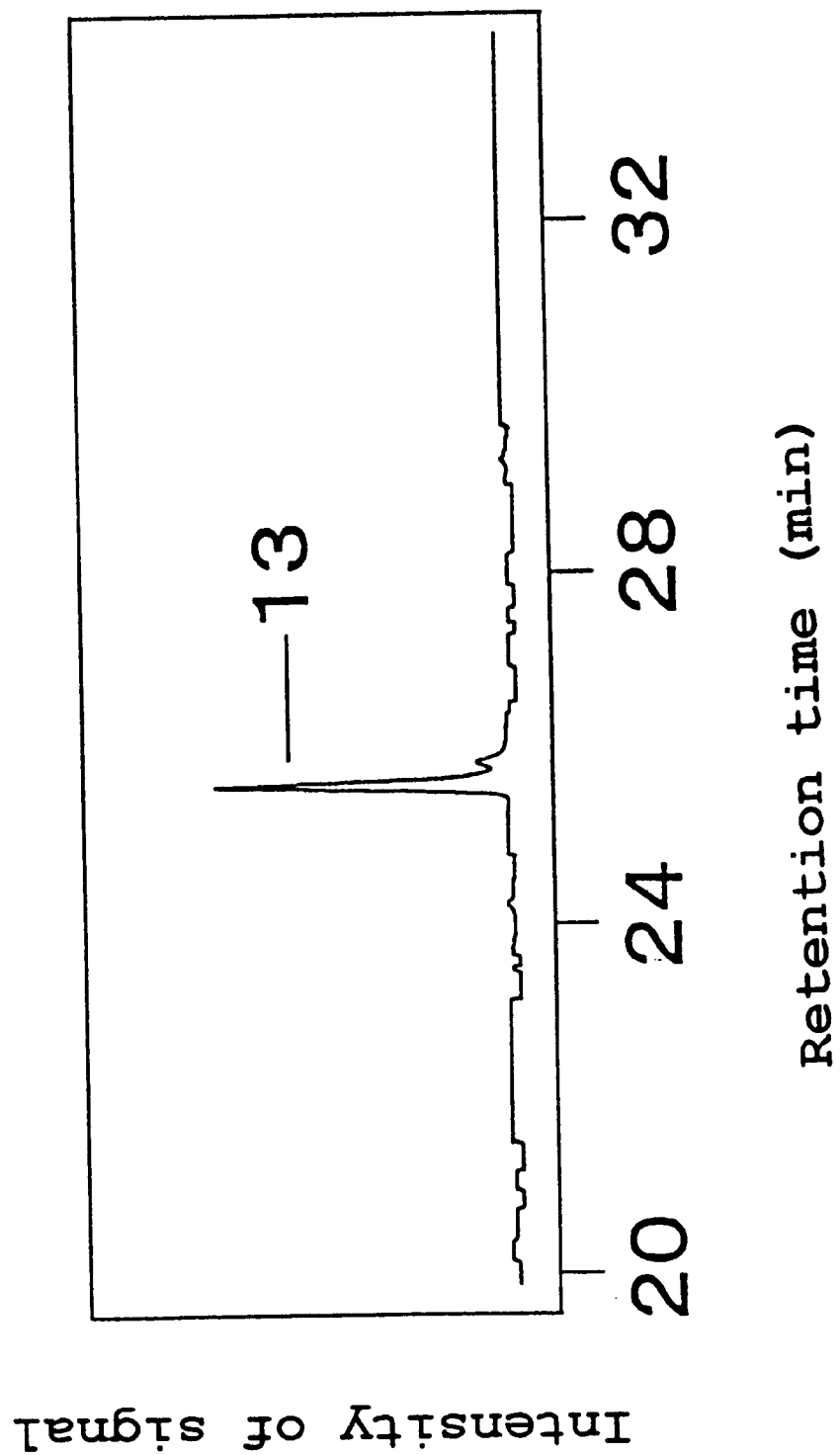
FIG. 17 shows a drawing showing a result of HPLC analysis to confirm generation of oxazolone.

(2) Dissolve the residue in 0.1% TFA Compared with FIG. 15, N-acetylalanyltryptophan (Ac-Ala-Trp) denoted by reference numeral 13 was detected in FIG. 17, this indicates generation of oxazolone in the first process. Here, alanyltryptophan used as the sample was not detected.

EXAMPLE 11

Here, cleavage of oxazolone under the conditions in the operation of the second process is described. As the sample, alanyltryptophan was used in the same manner as in Example 10. Detection was carried out by HPLC analysis under the same conditions as in Example 9. The procedure of preparing the sample for HPLC analysis was as described in Example 5.

Figure 18:
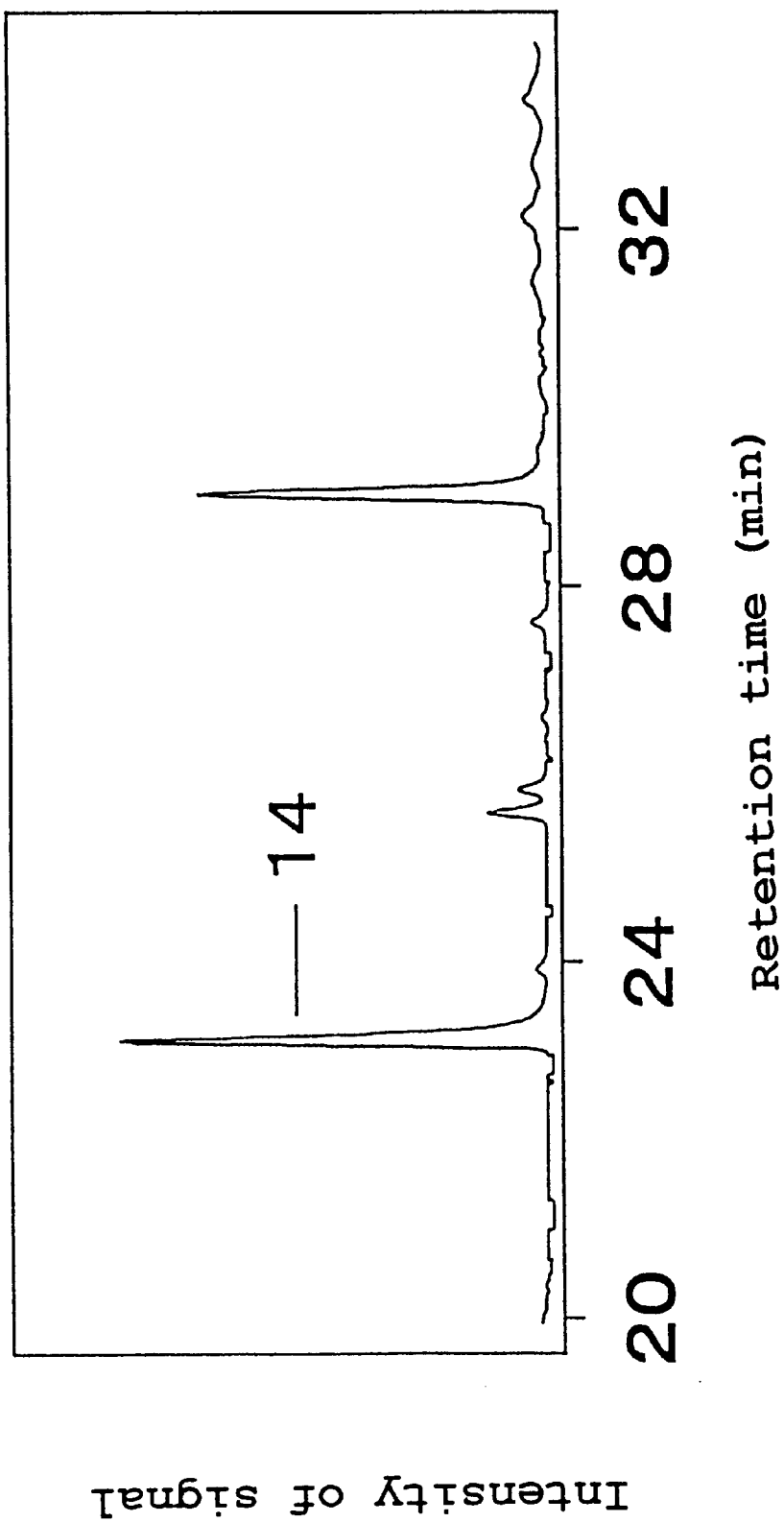
FIG. 18 shows a drawing showing a result of HPLC analysis to confirm cleavage of the oxazolone ring.

FIG. 10 shows the result of analyzing the reaction product obtained in the first and second processes described in Example 7. Compared with FIG. 13, tryptophan (reference numeral 14) was detected in FIG. 18 to indicate cleavage of the oxazolone ring under the conditions in the second process and liberation of the C-terminal amino acid.

EXAMPLE 12

In Example 11, the oxazolone was allowed to react with an alcohol solution of PFPA to liberate the carboxy-terminal amino acid. By the action of this alcohol (alcoholysis), the carboxyl group newly generated at the C-terminus is esterified in concurrence with the liberation of the amino acid. In order to continue the amino acid sequencing of the protein or the peptide from the C-terminus, the ester requires to be hydrolyzed to give a carboxyl group.

Here, hydrolysis of the ester under the conditions in the operation of the third process is described. As the sample, the ethyl ester of N-acetylalanyltryptophan (Ac-Ala-Trp-OEt) was used. Detection was carried out by HPLC analysis under the same conditions as in Example 9.

The procedure of preparing the sample for HPLC analysis was as described in Example 5.

Figure 19:
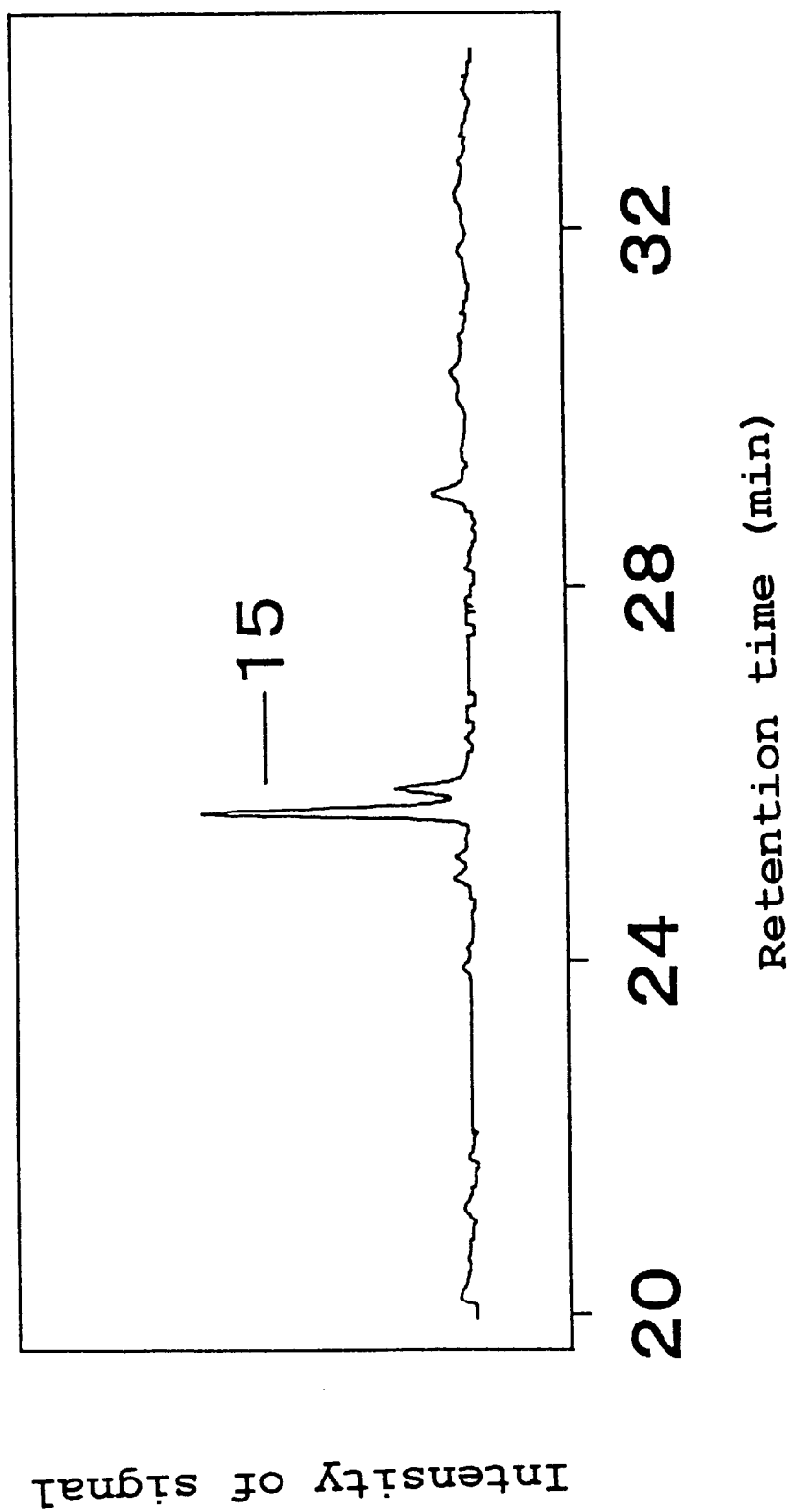
FIG. 19 shows a drawing showing a result of HPLC analysis to confirm hydrolysis.

FIG. 11 shows the result of analyzing the reaction product obtained in the third process described in Example 7. Compared with FIG. 1S, N-acetylalanyltryptophan (Ac-Ala-Trp) (reference numeral 15) was detected in FIG. 19 to indicate hydrolysis of the ester by the action of the aqueous solution of amine under the conditions in the third process of Example 7.

EXAMPLE 13

In the subsequent examples, the present invention will be described using mass spectrometry.

This example shows the conditions of mass spectrometric analysis and the procedure for sample preparation.

Conditions for mass spectrometric analysis

Analyzer: Double focusing mass spectrometer HX-110 (Nihon Denshi)

| Analysis conditions: | |
|---|---|
| Accelerating potential | 10 kV |
| Resolution | 1,000 |
| Ion source | FAB(fast-atom bombardment method) |
| Ionization gas | Xe |
| Ion mode | cationic |
| FAB gun accelerating potential | 6 kV |
| Detector | MULTIPLIER |
| Load potential | −20 kV |
| Data processing system | DA5000 |
| Matrix | | glycerol:thioglycerol:m-nitrobenzyl alcohol = 1:1:1

Procedure for sample preparation (1) Evaporate a sample under reduced pressure to dryness.

(2) Dissolve the residue in 67% acetic acid (or dimethylformamide) aqueous solution.

(3) Place the matrix of 1 μl on the target.

(4) Place the sample solution of 1 μl on the target and allow them to mix.

(5) Introduce the mixture into the ion source.

EXAMPLE 14

Here, an investigation of the reaction conditions for generation of oxazolone in the first process using mass spectrometry is described. As the sample, a pentapeptide of Sequence No.3, ("SEQ ID NO: 3") leucyltryptophanylmethionylarginylphenylalanine (Leu-Trp-Met-Arg-Phe), was used. In this example, the second process was successively carried out after the first process.

The reaction conditions in the first process are the same as in Example 2 as follows.

Reaction conditions

Concentration of acetic anhydride: 20% (acetonitrile solution, acetic acid added to adjust to 1% of the concentration)

Reaction temperature: 60° C.

Reaction period: 30 minutes

The reaction conditions in the second process were as follows. Heptafluorobutyric acid (CF3—CF2—CF2—COOH; hereinafter referred to as HFBA) and ethanol were used as the acid and the alcohol, respectively.

Reaction conditions

Concentration of HFBA: 5% (ethanol solution)

Reaction temperature: 60° C.

Reaction period: 30 minutes

Figure 20:
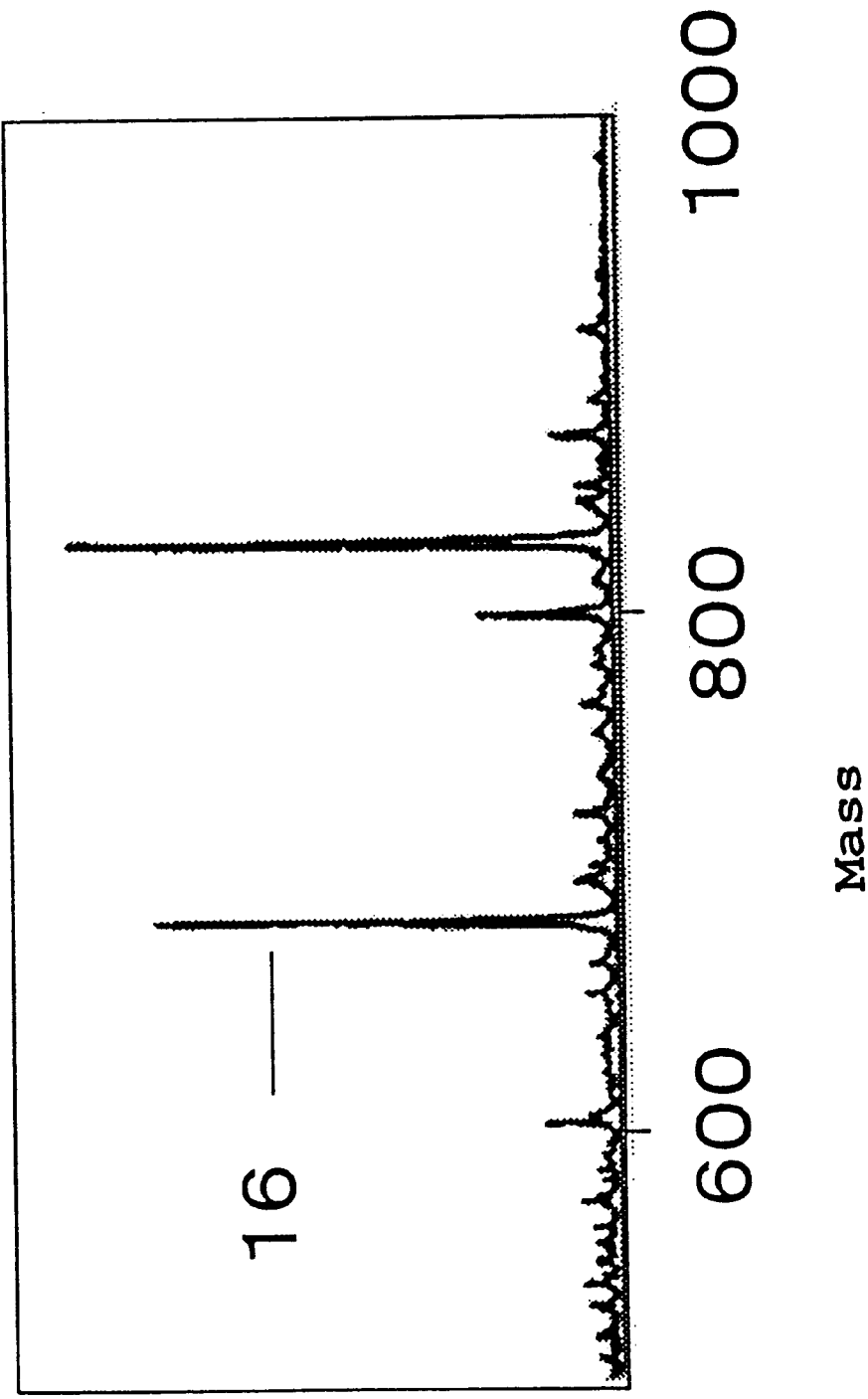
FIG. 20 shows a drawing showing a result of mass spectrometric analysis of the sample obtained in Example 8.

FIG. 20 shows a result of mass spectrometric analysis of the sample obtained. Here, a molecular ion (reference numeral 16) corresponding to the reaction product whose amino terminal was acetylated, C-terminal amino acid was lacking, and carboxyl group at the C-terminus was esterified with an ethyl group (the ethyl ester of acetylleucyltriptophanylmethionylarginine, molecular weight of 675; hereinafter referred to as Ac-LWMR-OEt) was detected to indicate generation of oxazolone in the first process and liberation of the C-terminal amino acid in the second process.

EXAMPLE 15

Here, another example of the reaction conditions in the first process is described. As the sample, the pentapeptide of Sequence No.3 was used in the same manner as in Example 14. The procedures are the same as in Example 14. The reaction conditions in the first process were as follows.

| Reaction conditions | |
|---|---|
| Concentration of acetic anhydride (acetonitrile solution, without addition of acetic acid) | 20% |
| Reaction temperature | 60° C. |
| Reaction period | 30 minutes |

The reaction conditions in the second process are the same as in Example 13.

Figure 21:
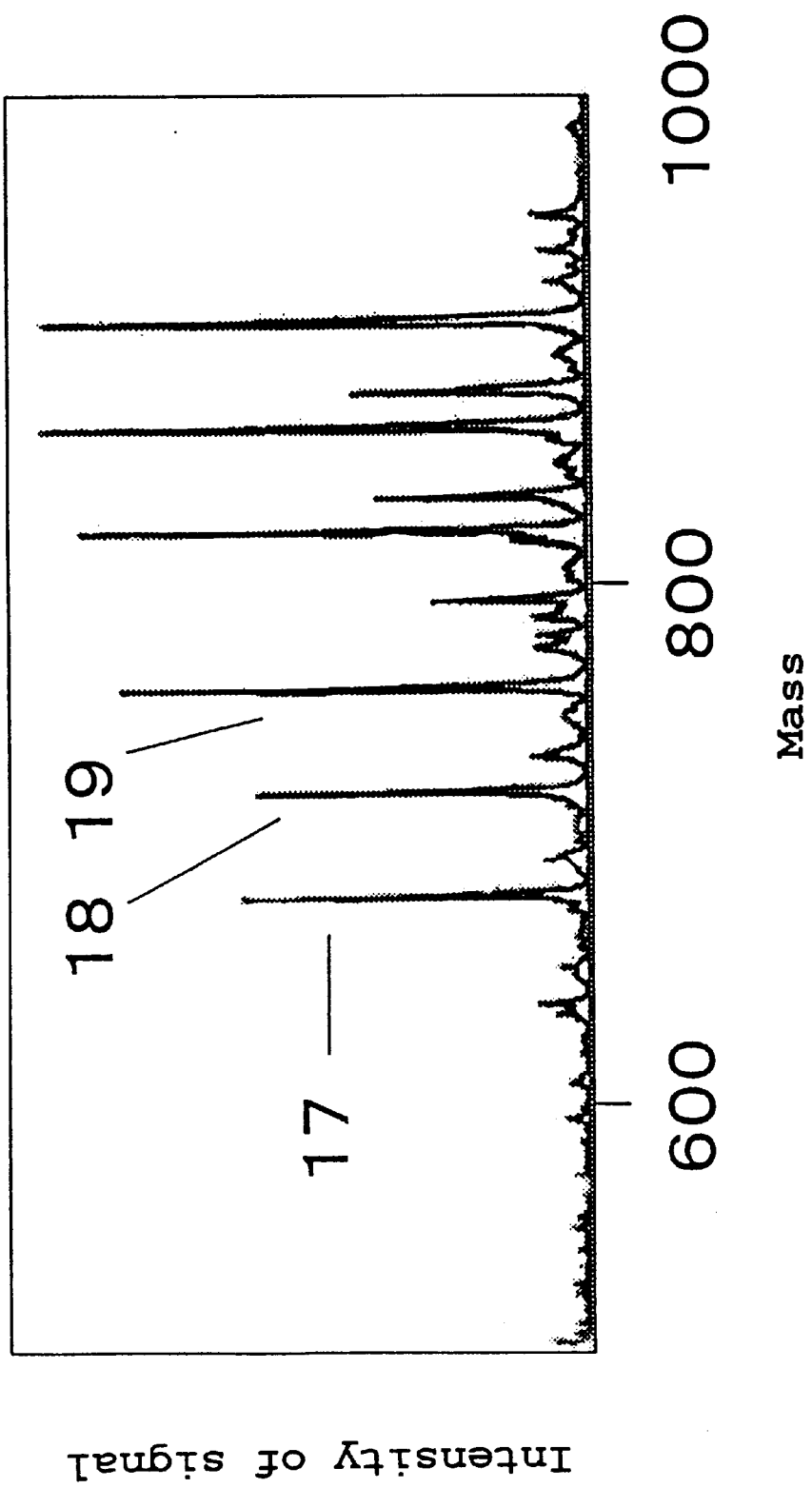
FIG. 21 shows a drawing showing a result of mass spectrometric analysis of the sample obtained in Example 9.

FIG. 21 shows a result of mass spectrometric analysis of the sample obtained. Under these conditions, also, molecular ion corresponding to Ac-LWMR-OEt was detected (reference numeral 17) to indicate generation of oxazolone in the first process. Simultaneously, molecular ion having 718 and 761 of molecular weight were detected (reference numerals 18 and 19, respectively), to indicate generation of chemical species which were further acetylated reaction products, whose amino terminal was acetylated, the C-terminal amino acid was lacking, and the carboxyl group at the C-terminus was esterified with an ethyl group.

EXAMPLE 16

Here, another example of the reaction conditions in the first process is described. As the sample, the pentapeptide of Sequence No.3 was used in the same manner as in Example 9. The procedures followed in Example 14. The reaction conditions in the first process were as follows.

| Reaction conditions | |
| --- | --- |
| Concentration of acetic anhydride (acetonitrile solution, acetic acid added to adjust to 2% of the concentration) | 20% |
| Reaction temperature | 60° C. |
| Reaction period | 30 minutes |

The reaction conditions in the second process are the same as in Example 16.

Figure 22:
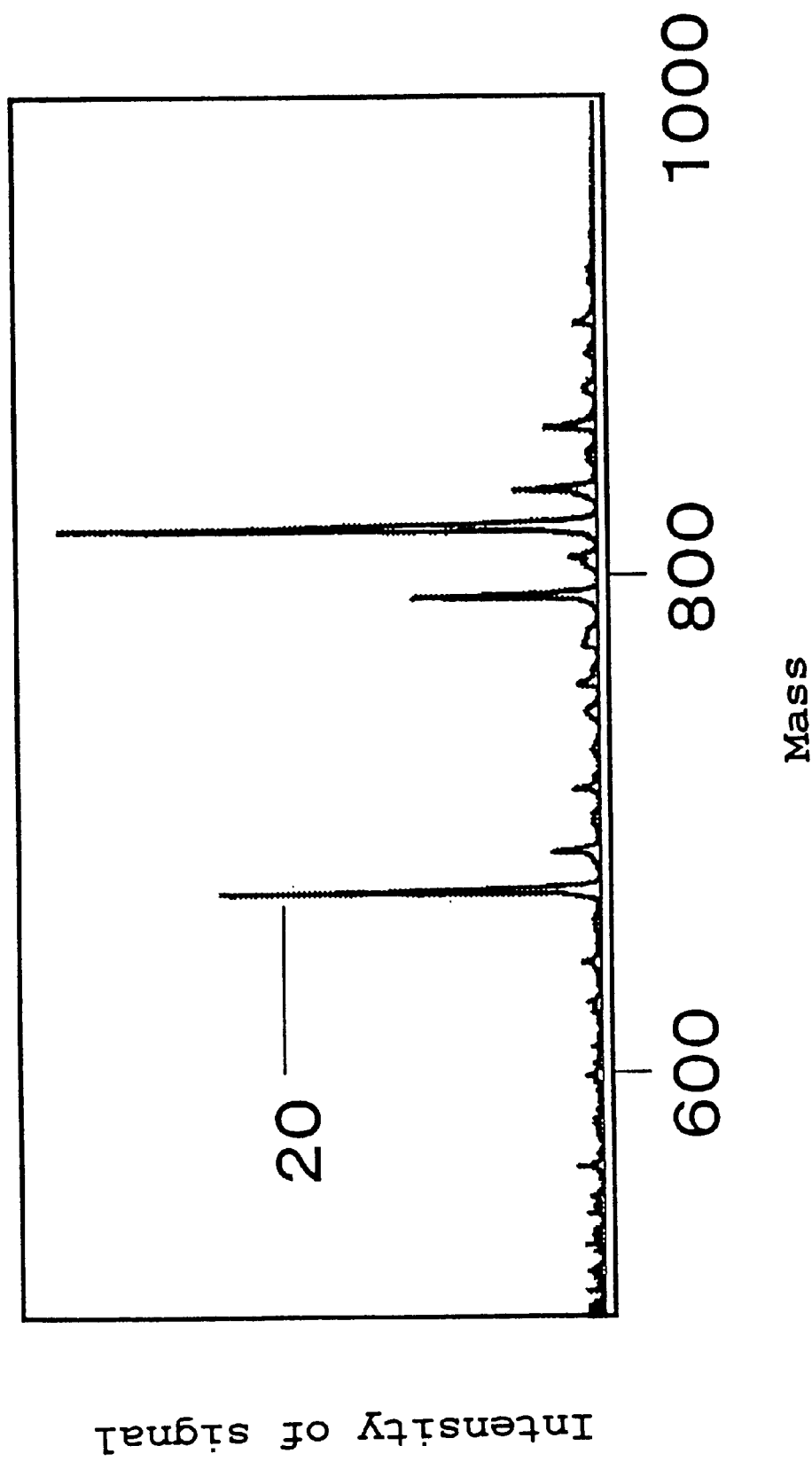
FIG. 22 shows a drawing showing a result of mass spectrometric analysis of the sample obtained in Example 10.

FIG. 22 shows a result of mass spectrometric analysis of the sample obtained. Under these conditions, also, molecular ion corresponding to Ac-LWMR-OEt (reference numeral 20) was detected to indicate generation of oxazolone in the first process.

EXAMPLE 17

Here, another example of the reaction conditions in the first process is described. As the sample, the pentapeptide of Sequence No.3 was used in the same manner as in Example 9. The procedures followed in Example 14. The reaction conditions in the first process were as follows.

| Reaction conditions | |
| --- | --- |
| Concentration of acetic anhydride | 5% (acetonitrile solution, acetic acid added to adjust to 1% of the concentration) |
| Reaction temperature | 60° C. |
| Reaction period | 30 minutes |

The reaction conditions in the second process are the same as in Example 14.

Figure 23:
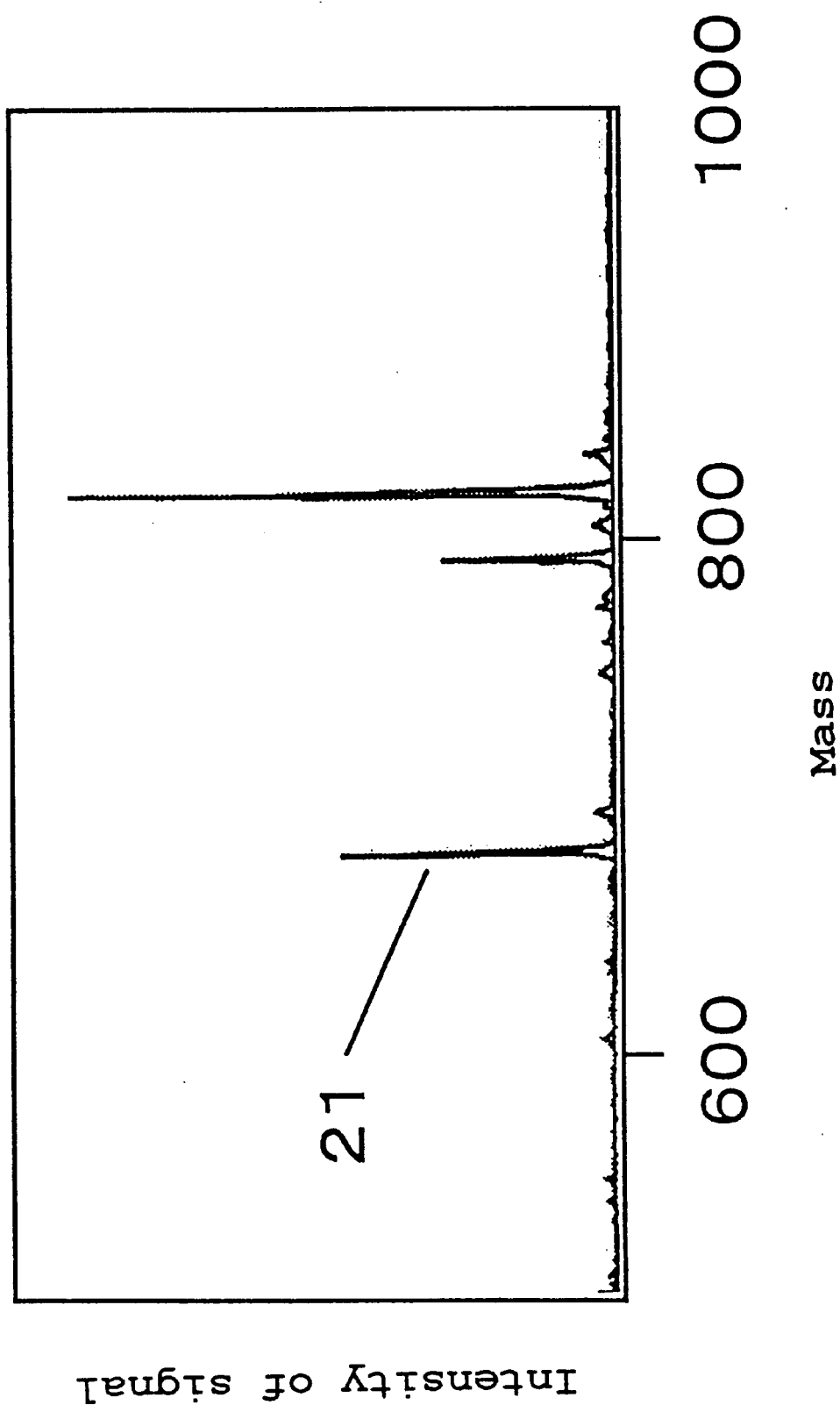
FIG. 23 shows a drawing showing a result of mass spectrometric analysis of the sample obtained in Example 11.

FIG. 23 shows a result of mass spectrometric analysis of the sample obtained. Under these conditions, also, molecular ion corresponding to Ac-LWMR-OEt (reference numeral 21) was detected to indicate generation of oxazolone in the first process.

EXAMPLE 18

Here, an investigation of the reaction conditions for liberation of the C-terminal amino acid in the second process is described. As the sample, a pentapeptide of Sequence No.3 was used. In the subsequent examples, also, the second process was successively carried out after the first process.

Figure 24:
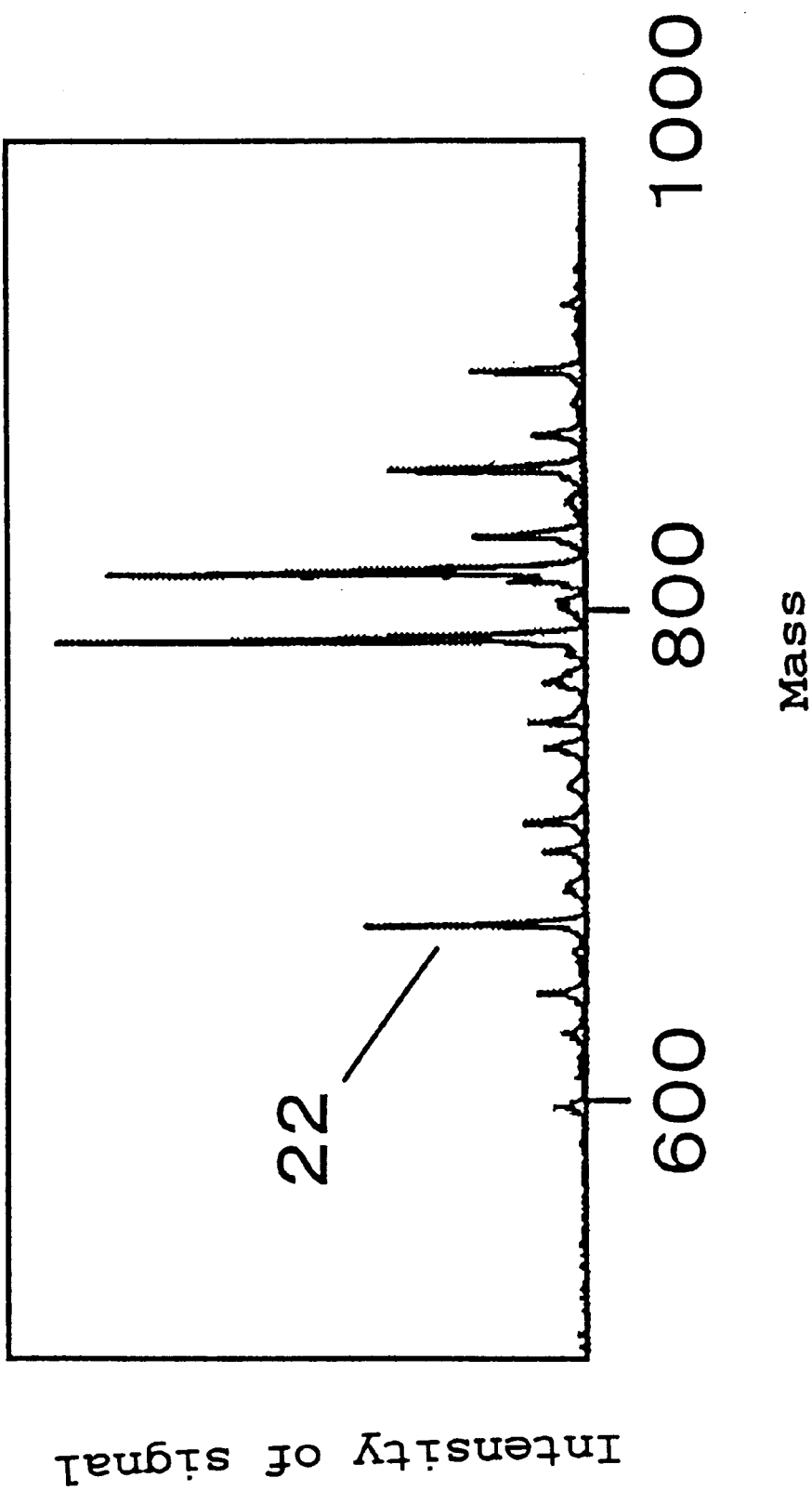
FIG. 24 shows a drawing showing a result of mass spectrometric analysis of the sample obtained in Example 12.

The reaction conditions in the first process are the same as in Example 14 as follows.
Reaction conditions
Concentration of acetic anhydride: 20% (acetonitrile solution, acetic acid added to adjust to 1% of the concentration)
Reaction temperature: 60° C.
Reaction period: 30 minutes The reaction conditions in the second process were changed as follows.
Reaction conditions
Concentration of HFBA: 2% (ethanol solution)
Reaction temperature: 60° C.
Reaction period: 30 minutes FIG. 24 shows a result of mass spectrometric analysis of the sample obtained. Here, a molecular ion corresponding to Ac-LWMR-OEt (reference numeral 22) was detected to indicate generation of oxazolone in the first process and liberation of the C-terminal amino acid in the second process.

EXAMPLE 19

Here, the reaction conditions in the second process were changed as follows.
Reaction conditions
Concentration of HFBA: 5% (ethanol solution)
Reaction temperature: 60° C.
Reaction period: 10 minutes The reaction conditions in the first process followed in Example 9.

Figure 25:
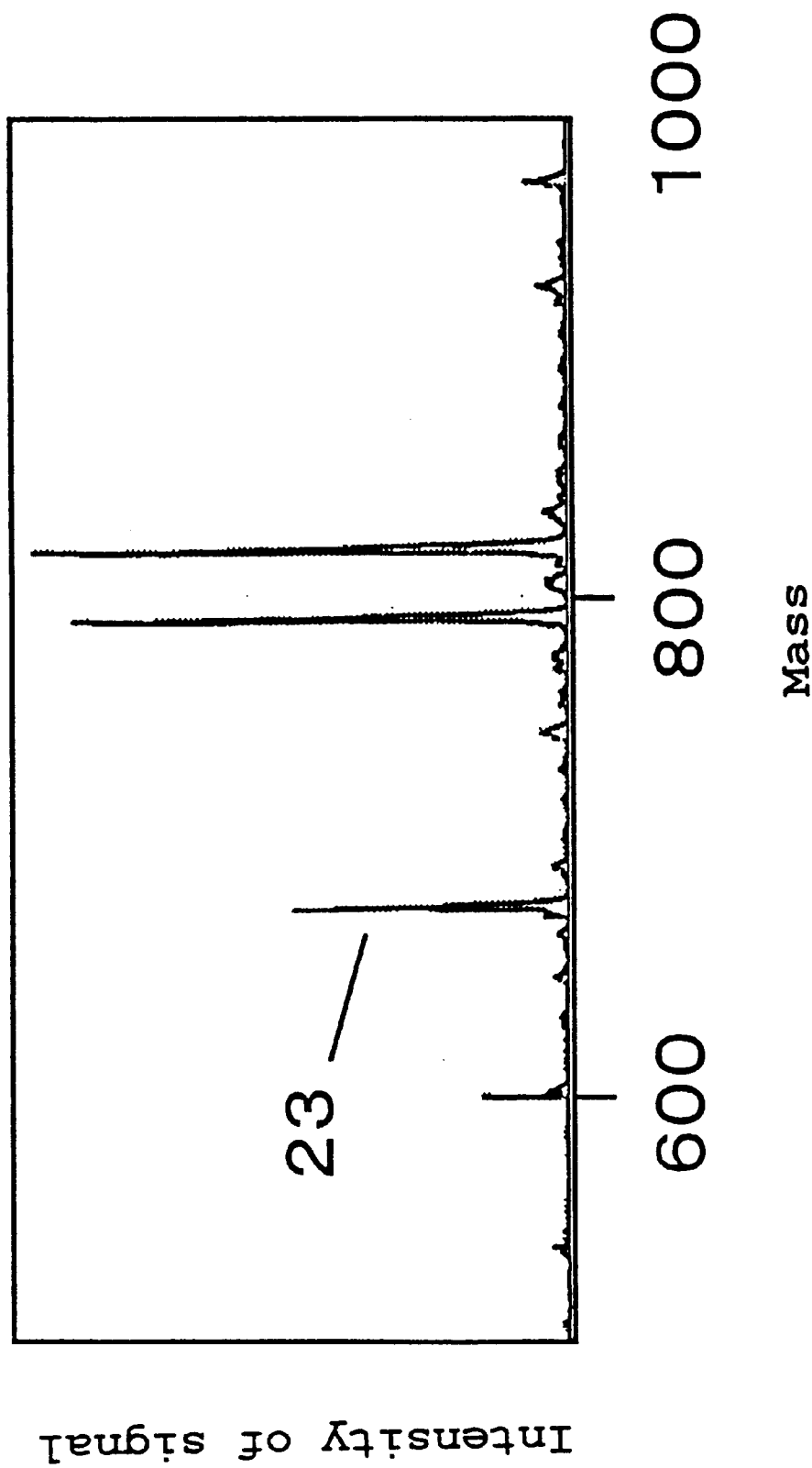
FIG. 25 shows a drawing showing a result of mass spectrometric analysis of the sample obtained in Example 13.

FIG. 25 shows a result of mass spectrometric analysis of the sample obtained. Under these conditions, also, a molecular ion corresponding to Ac-LWMR-OEt (reference numeral 23) was detected to indicate generation of oxazolone in the first process and liberation of the C-terminal amino acid in the second process.

EXAMPLE 20

Here, the reaction conditions in the second process were changed as follows.
Reaction conditions
Concentration of HFBA: 5% (ethanol solution)
Reaction temperature: room temperature
Reaction period: 30 minutes The reaction conditions in the first process are the same as in Example 14.

Figure 26:
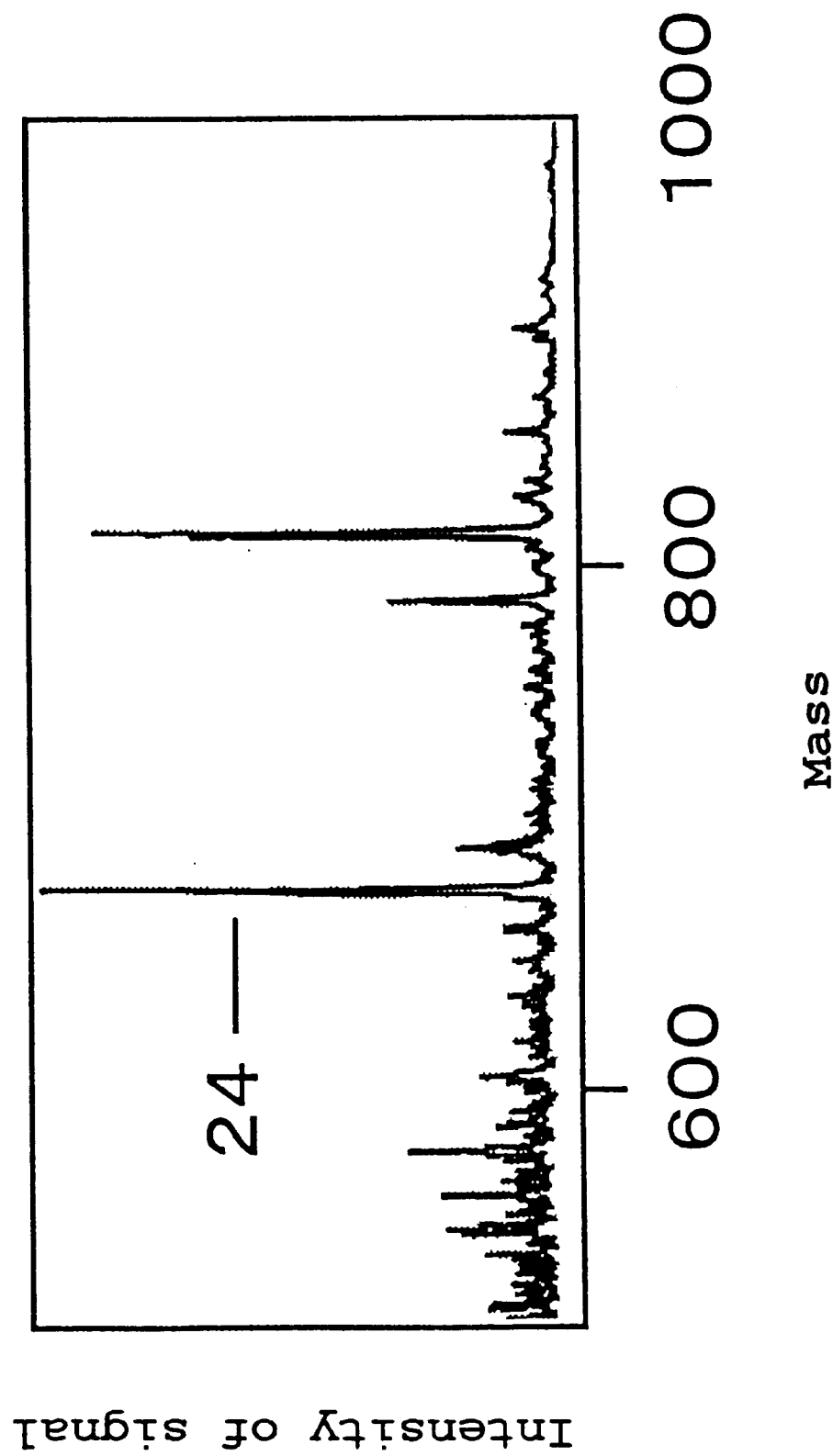
FIG. 26 shows a drawing showing a result of mass spectrometric analysis of the sample obtained in Example 14.

FIG. 26 shows the result of mass spectrometric analysis of the sample obtained. Under these conditions, also, a molecular ion corresponding to Ac-LWMR-OEt (reference numeral 24) was detected to indicate generation of oxazolone in the first process and liberation of the C-terminal amino acid in the second process.

EXAMPLE 21

Here, the reaction conditions in the second process were changed as follows.
Reaction conditions
Concentration of HFBA: 5% (ethanol solution)
Reaction temperature: 5° C.
Reaction period: 30 minutes The reaction conditions in the first process are the same as in Example 14.

Figure 27:
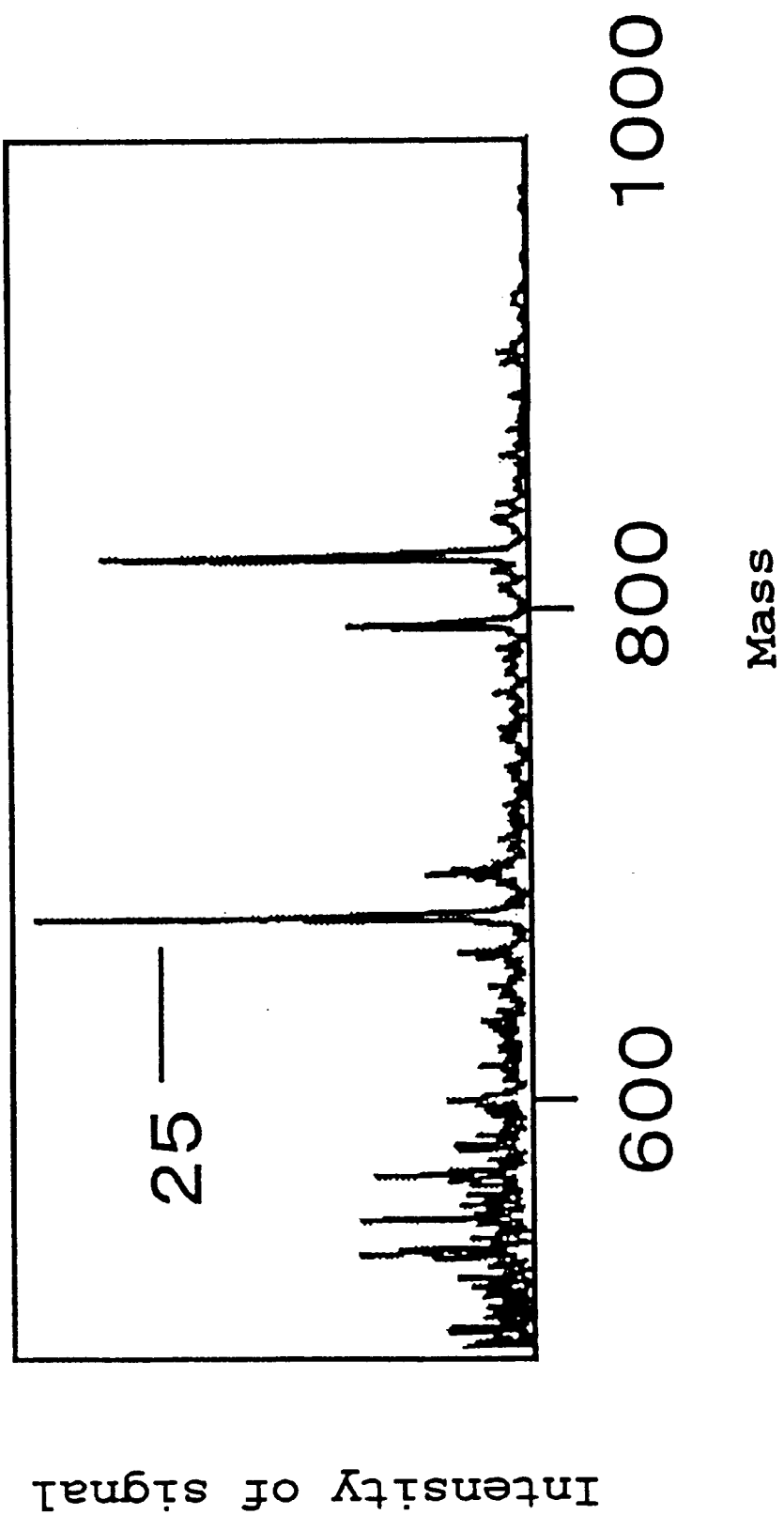
FIG. 27 shows a drawing showing a result of mass spectrometric analysis of the sample obtained in Example 15.

FIG. 27 shows the result of mass spectrometric analysis of the sample obtained. Under these conditions, also, a molecular ion corresponding to Ac-LWMR-OEt (reference numeral 25) was detected to indicate generation of oxazolone in the first process and liberation of the C-terminal amino acid in the second process.

EXAMPLE 22

Here, the reaction conditions in the second process were changed as follows.

Reaction conditions

Concentration of HFBA: 5% (ethanol solution)

Reaction temperature: 100° C.

Reaction period: 15 minutes

The reaction conditions in the first process followed in Example 14.

Figure 28:
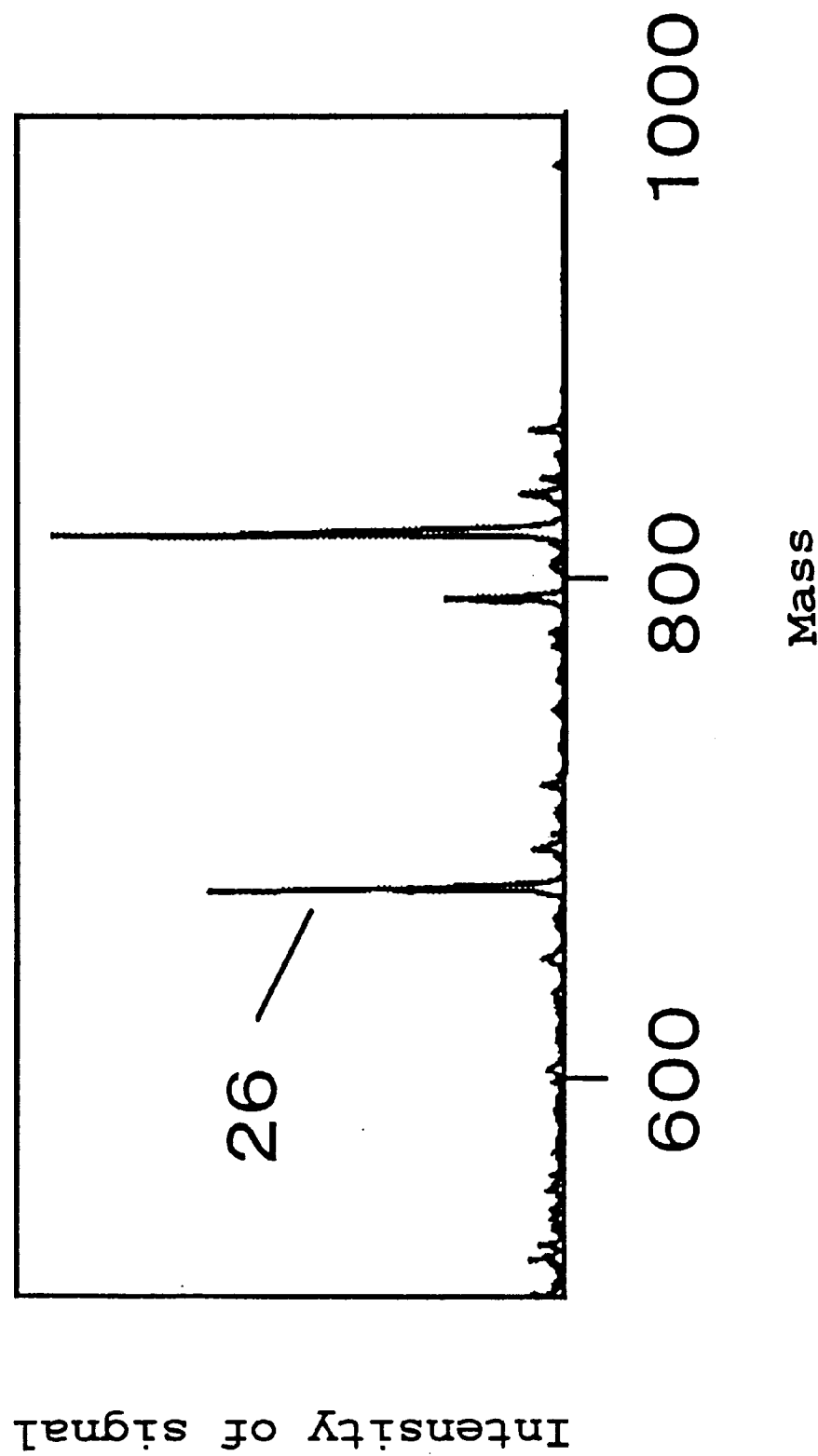
FIG. 28 shows a drawing showing a result of mass spectrometric analysis of the sample obtained in Example 16.

FIG. 28 shows a result of mass spectrometric analysis of the sample obtained. Under these conditions, also, a molecular ion corresponding to Ac-LWMR-OEt (reference numeral 26) was detected to indicate generation of oxazolone in the first process and liberation of the C-terminal amino acid in the second process.

EXAMPLE 23

Here, the reaction conditions in the second process were changed as follows.

Reaction conditions

Concentration of HFBA: 5% (methanol solution)

Reaction temperature: 60° C.

Reaction period: 30 minutes

The reaction conditions in the first process are the same as in Example 14.

Figure 29:
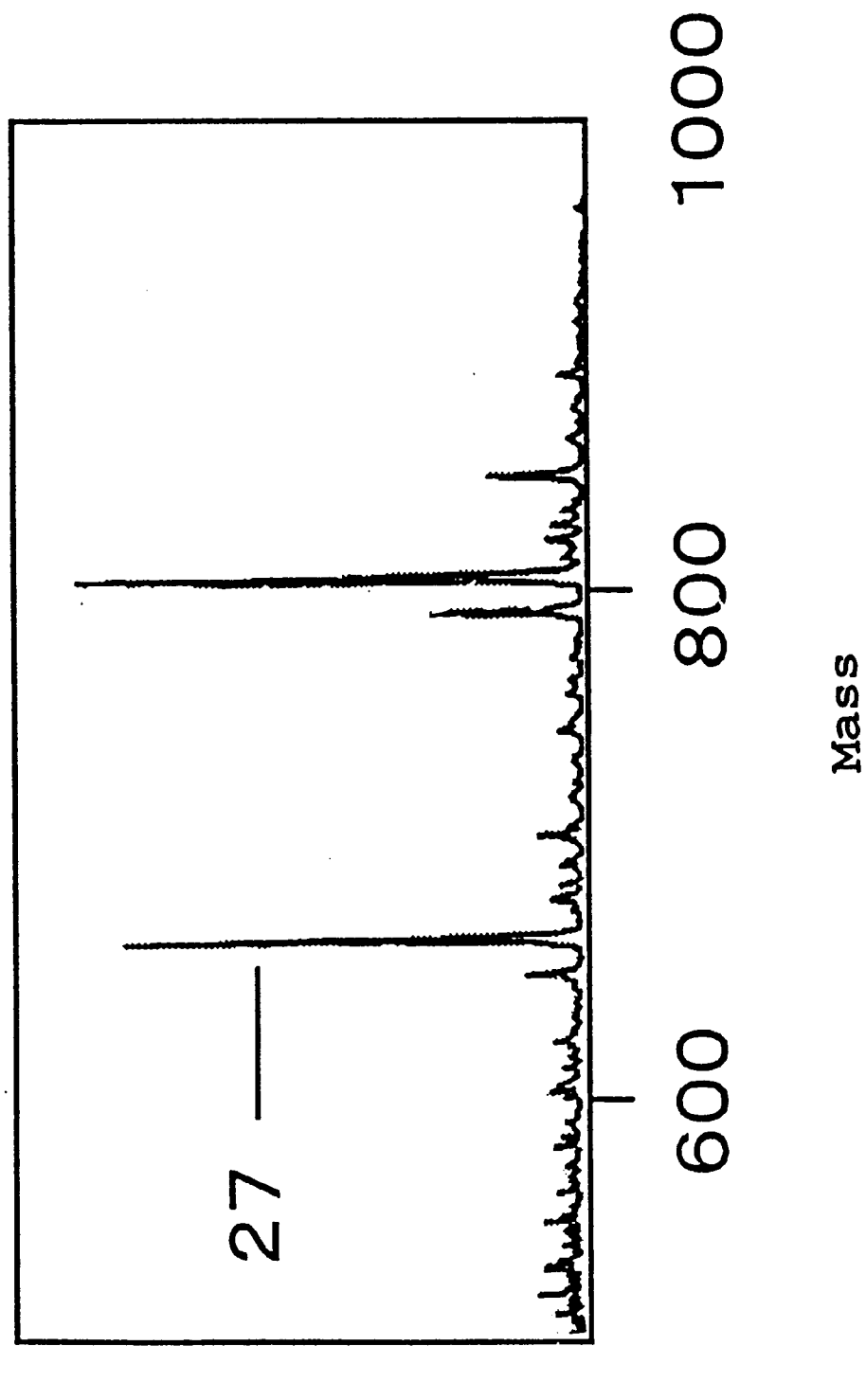
FIG. 29 shows a drawing showing a result of mass spectrometric analysis of the sample obtained in Example 17.

FIG. 29 shows a result of mass spectrometric analysis of the sample obtained. Under these conditions, a molecular ion (corresponding to the reaction product, whose amino terminus was acetylated, C-terminal amino acid was lacking, and carboxyl group at the C-terminus was esterified with a methyl group (the methyl ester of acetylleucyltriptophanylmethionylarginine, molecular weight of 661; hereinafter referred to as Ac-LWMR-OMe) (reference numeral 27) was detected to indicate generation of oxazolone in the first process and liberation of the C-terminal amino acid in the second process.

EXAMPLE 24

Here, the reaction conditions in the second process were changed as follows.

Reaction conditions

Concentration of HFBA: 5% (methanol solution)

Reaction temperature: 5° C.

Reaction period: 30 minutes

The reaction conditions in the first process are the same as in Example 14.

Figure 30:
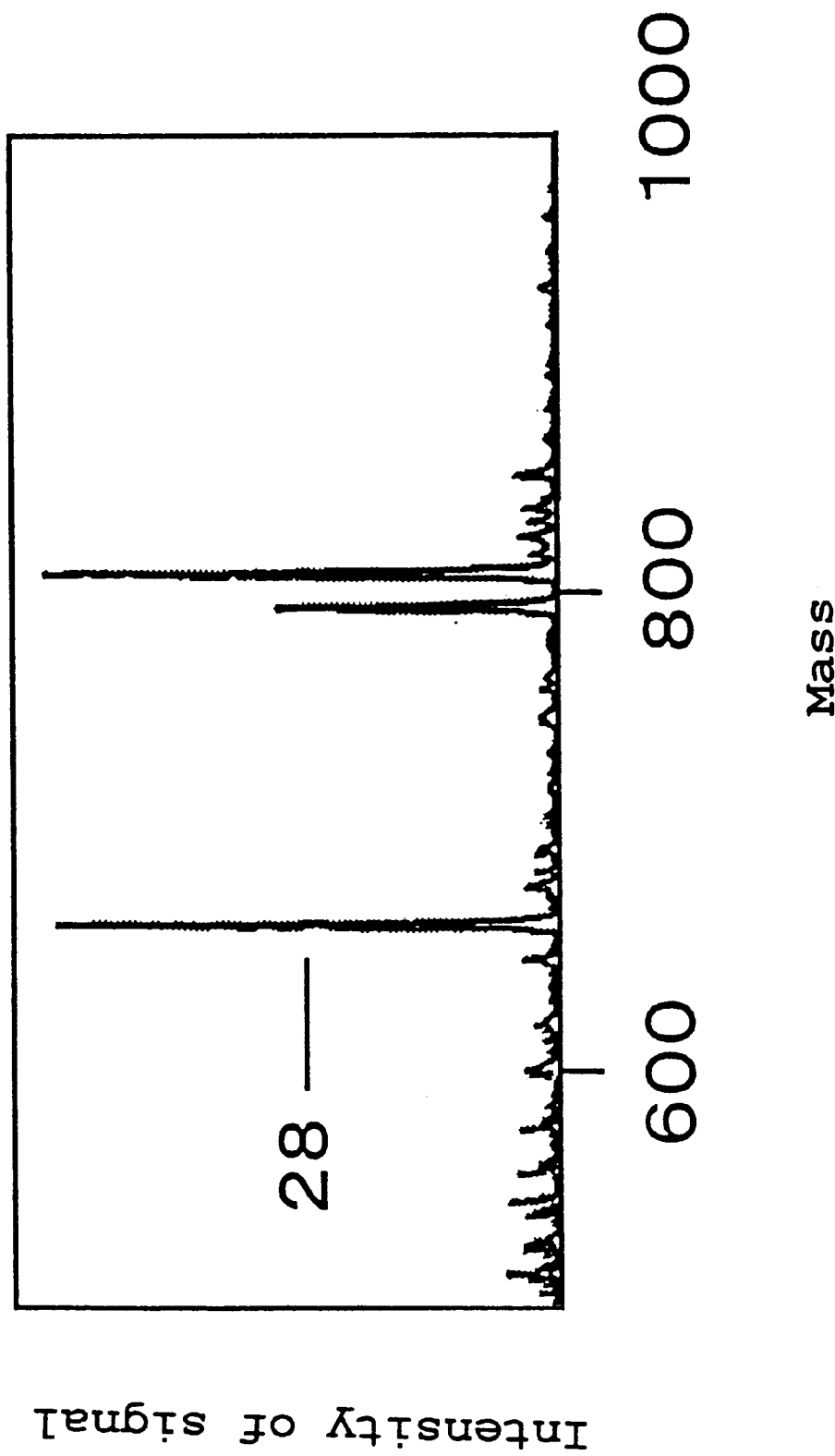
FIG. 30 shows a drawing showing a result of mass spectrometric analysis of the sample obtained in Example 18.

FIG. 30 shows a result of mass spectrometric analysis of the sample obtained. Under these conditions, also, a molecular ion corresponding to Ac-LWMR-OMe (reference numeral 28) was detected to indicate generation of oxazolone in the first process and liberation of the C-terminal amino acid in the second process.

EXAMPLE 25

Here, the reaction conditions in the second process were changed as follows.

Reaction conditions

Concentration of PFPA: 5% (ethanol solution)

Reaction temperature: 60° C.

Reaction period: 30 minutes

The reaction conditions in the first process are the same as in Example 14.

Figure 31:
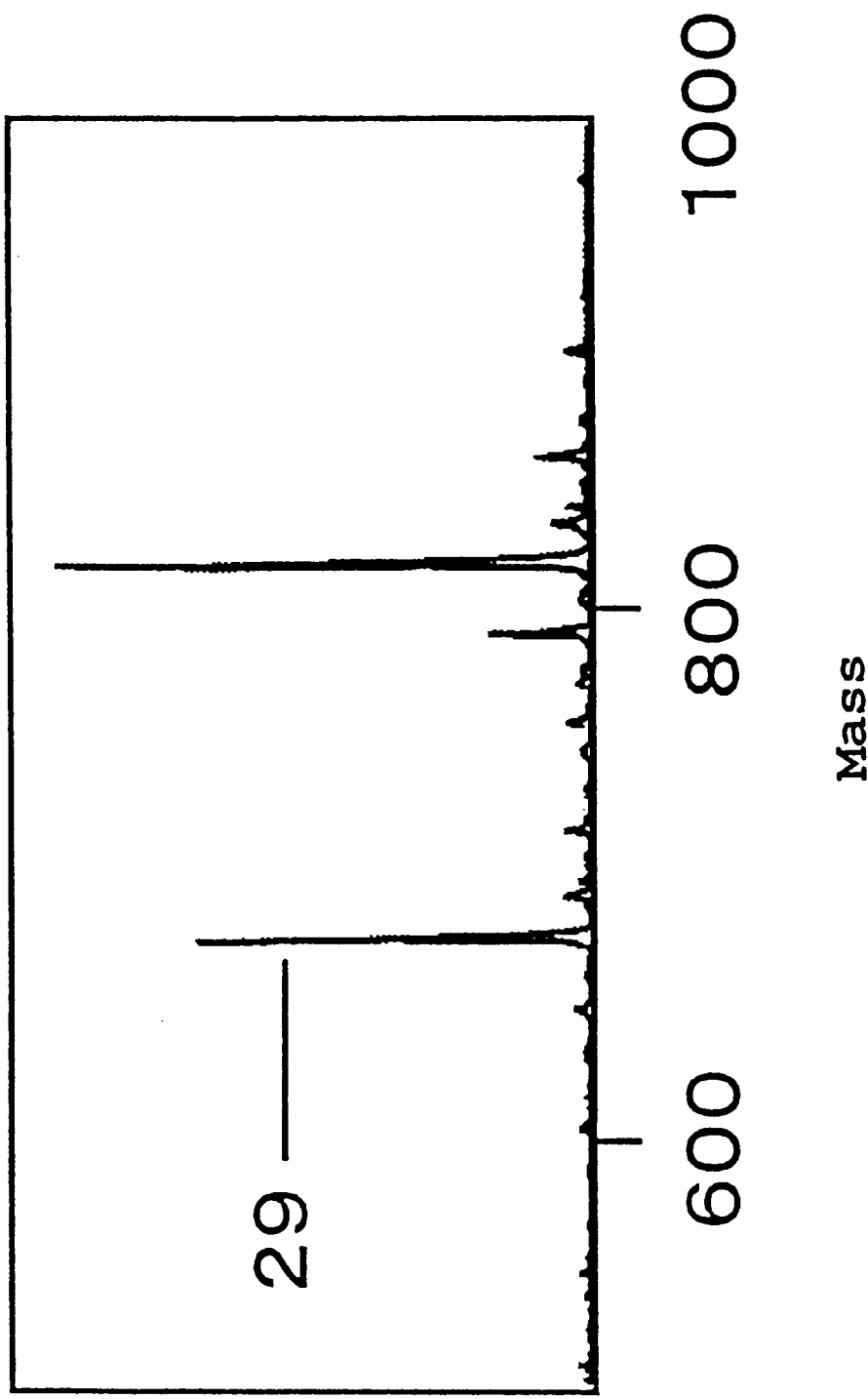
FIG. 31 shows a drawing showing a result of mass spectrometric analysis of the sample obtained in Example 19.

FIG. 31 shows a result of mass spectrometric analysis of the sample obtained. Under these conditions, a molecular ion corresponding to Ac-LWMR-OEt (reference numeral 29) was detected to indicate generation of oxazolone in the first process and liberation of the C-terminal amino acid in the second process.

EXAMPLE 26

Here, the reaction conditions in the second process were changed as follows.

Reaction conditions

Concentration of PFPA: 20% (ethanol solution)

Reaction temperature: 60° C.

Reaction period: 30 minutes

The reaction conditions in the first process are the same as in Example 14.

Figure 32:
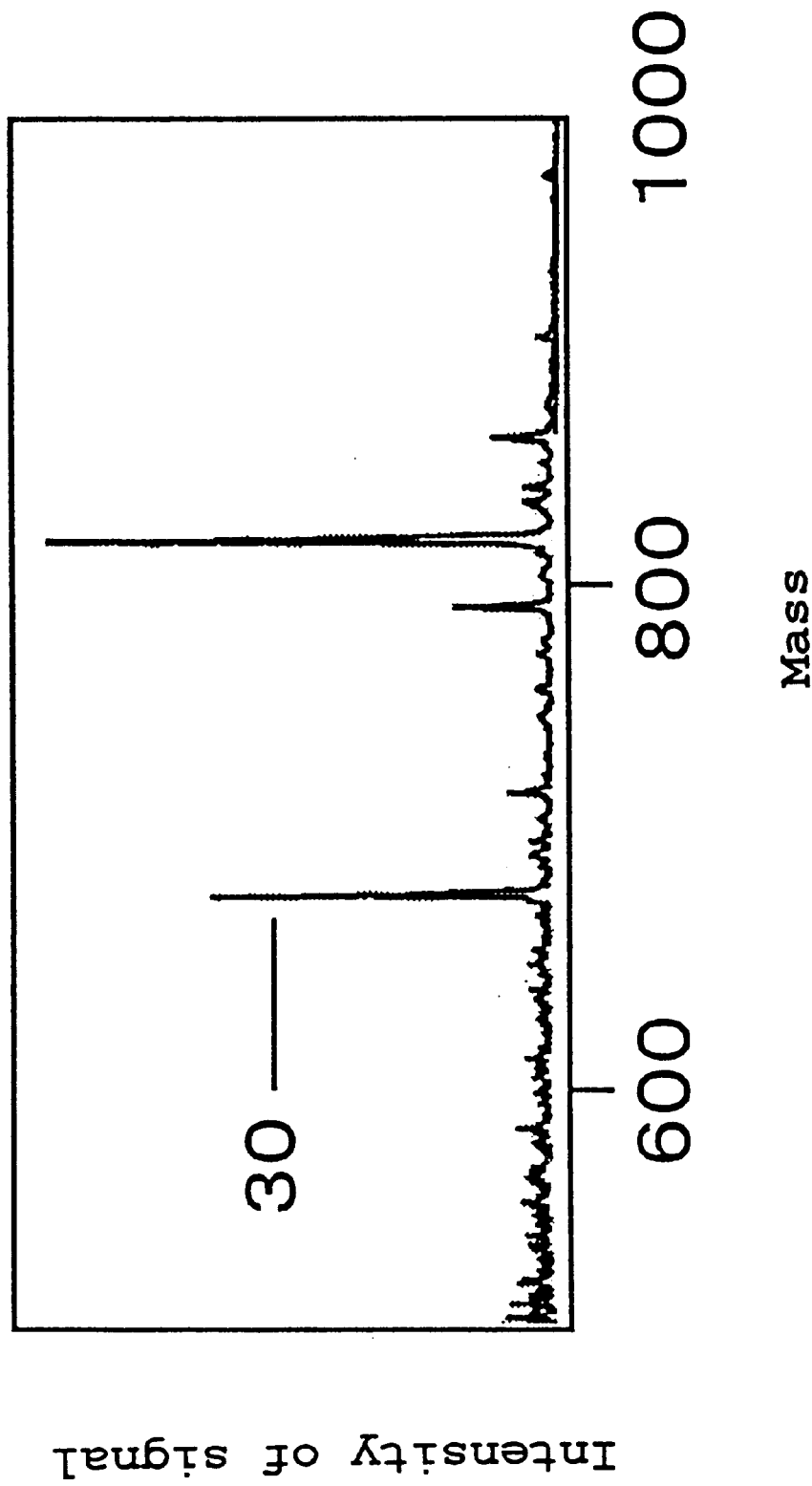
FIG. 32 shows a drawing showing a result of mass spectrometric analysis of the sample obtained in Example 20.

FIG. 32 shows a result of mass spectrometric analysis of the sample obtained. Under these conditions, also, a molecular ion corresponding to Ac-LWMR-OEt (reference numeral 30) was detected to indicate generation of oxazolone in the first process and liberation of the C-terminal amino acid in the sec ond process.

EXAMPLE 27

Here, the reaction conditions in the first process were as follows.

Reaction conditions

Concentration of acetic anhydride: 20% (acetonitrile solution, acetic acid added to adjust to 1% of the concentration)

Reaction temperature: 60° C.

Reaction period: 10 minutes

The reaction conditions in the second process were as follows.

Reaction conditions

Concentration of HFBA: 5% (methanol solution)

Reaction temperature: room temperature

Reaction period: 30 minutes

Figure 33:
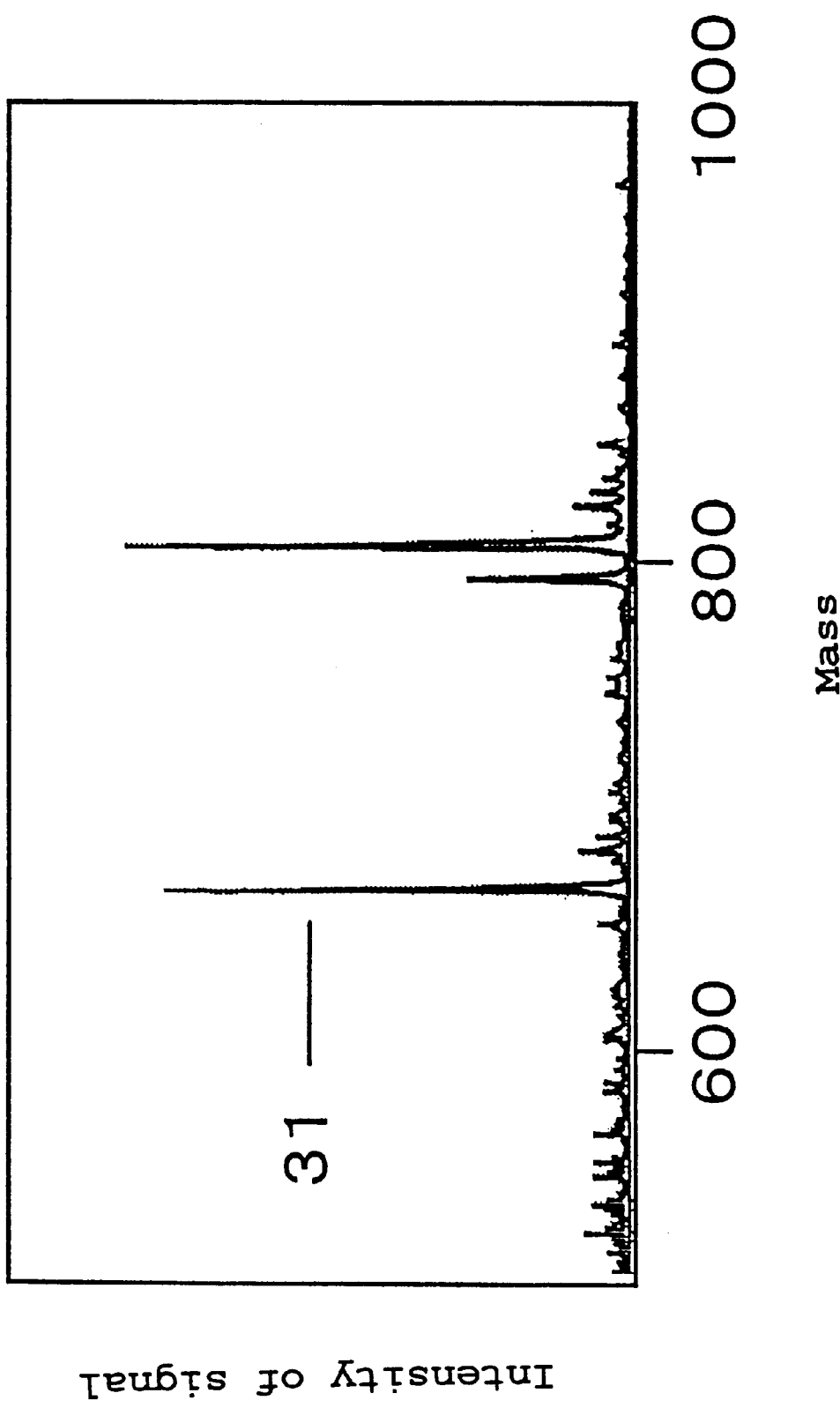
FIG. 33 shows a drawing showing a result of mass spectrometric analysis of the sample obtained in Example 21.

FIG. 33 shows a result of mass spectrometric analysis of the sample obtained. Under these conditions, also, a molecular ion corresponding to Ac-LWMR-OMe (reference numeral 31) was detected to indicate generation of oxazolone in the first process.

EXAMPLE 28

Here, the reaction conditions in the first process were as follows.

Reaction conditions

Concentration of acetic anhydride: 20% (acetonitrile solution, acetic acid added to adjust to 1% of the concentration)

Reaction temperature: 90° C.

Reaction period: 10 minutes

The reaction conditions in the second process were as follows.

Reaction conditions

Concentration of HFBA: 5% (methanol solution)

Reaction temperature: room temperature

Reaction period: 30 minutes

Figure 34:
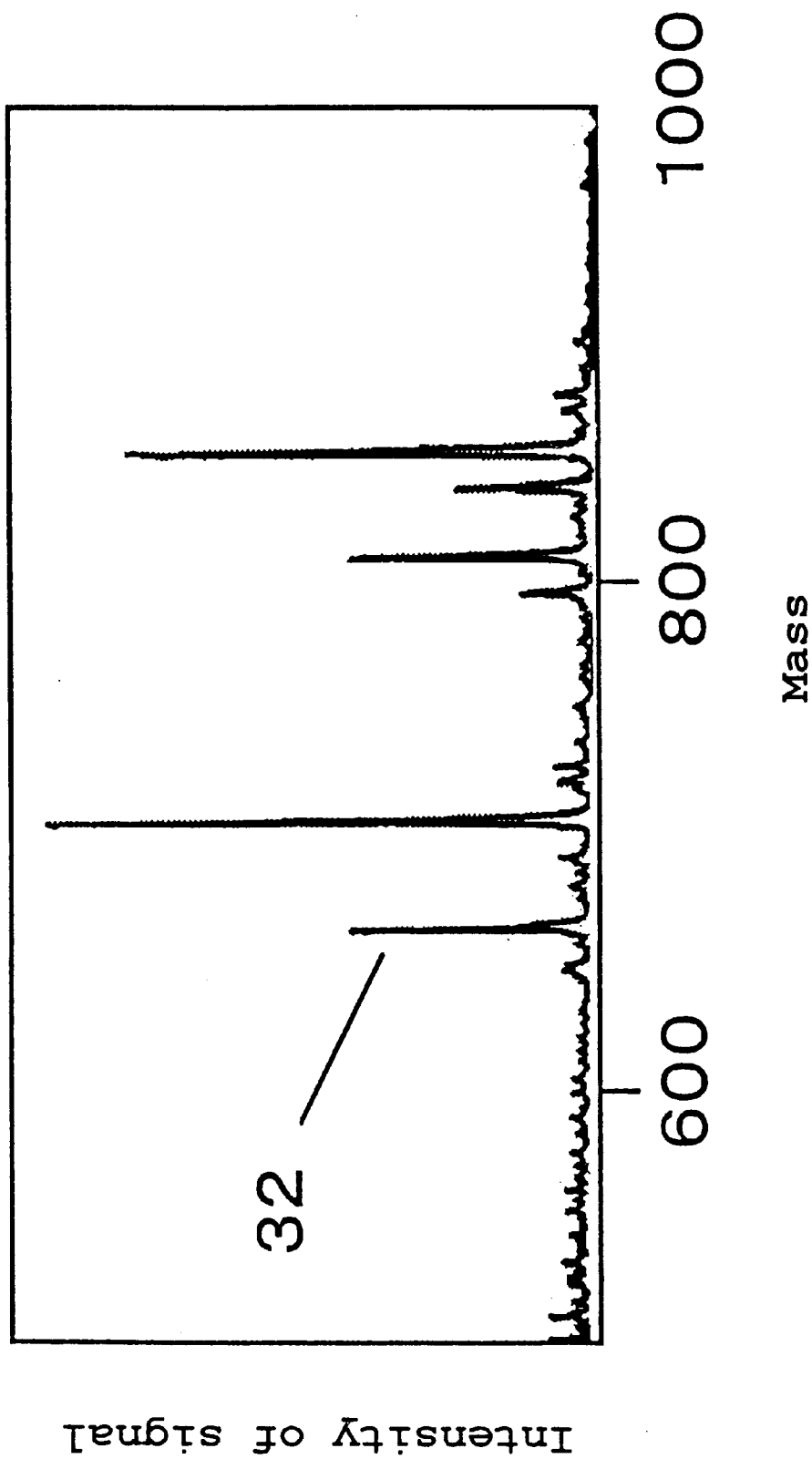
FIG. 34 shows a drawing showing a result of mass spectrometric analysis of the sample obtained in Example 22.

FIG. 34 shows a result of mass spectrometric analysis of the sample obtained. Under these conditions, also, a molecular ion corresponding to Ac-LWMR-OMe (reference numeral 32) was detected to indicate generation of oxazolone in the first process and liberation of the C-terminal amino acid in the second process.

EXAMPLE 29

Here, the reaction conditions in the first process were as follows.

Reaction conditions

Concentration of acetic anhydride: 20% (acetonitrile solution, acetic acid added to adjust to 1% of the concentration)

Reaction temperature: room temperature

Reaction period: 30 minutes

The reaction conditions in the second process were changed as follows.

Reaction conditions

Concentration of HFBA: 5% (methanol solution)

Reaction temperature: 60° C.

Reaction period: 30 minutes

Figure 35:
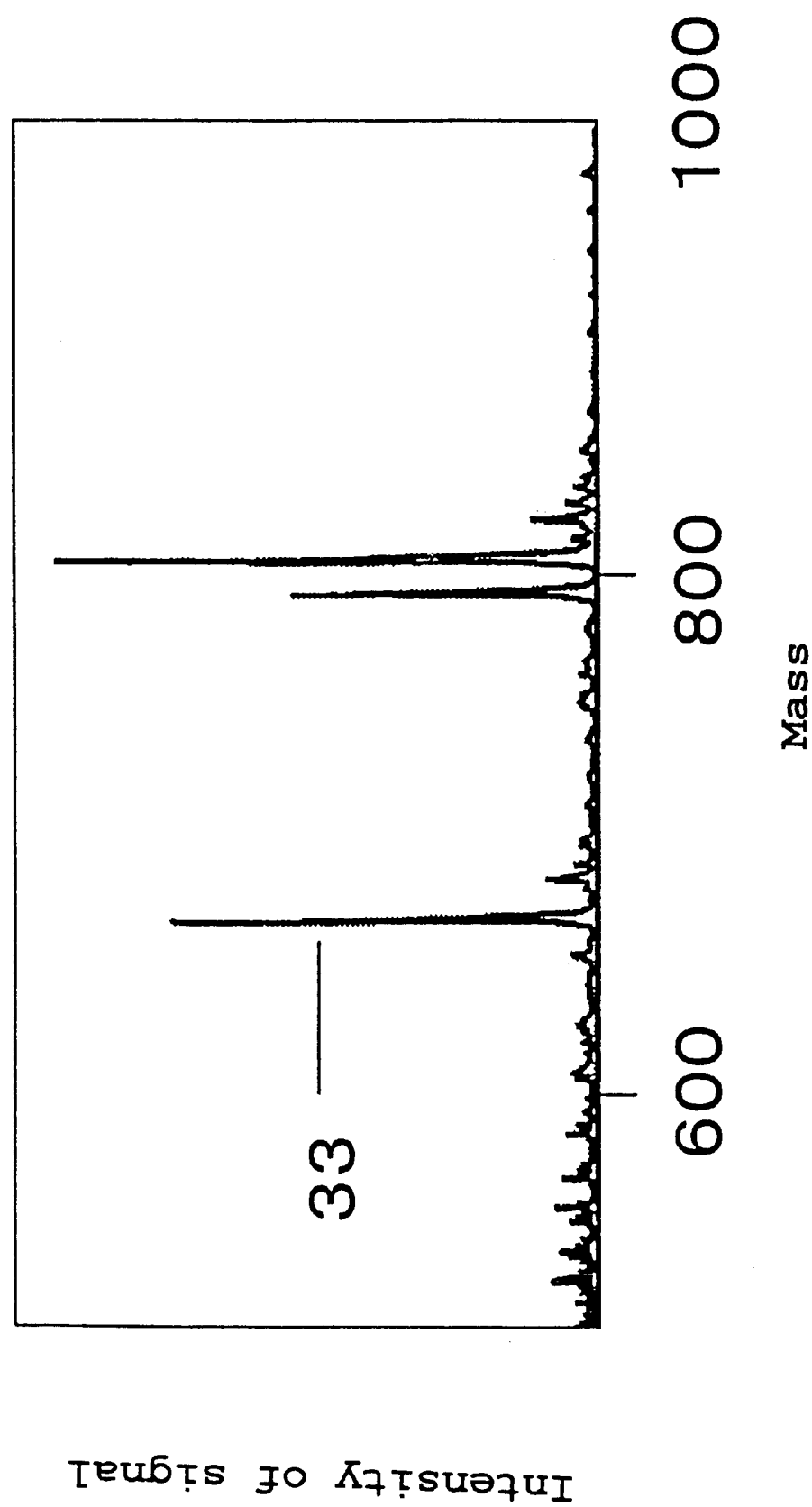
FIG. 35 shows a drawing showing a result of mass spectrometric analysis of the sample obtained in Example 23.

FIG. 35 shows a result of mass spectrometric analysis of the sample obtained. Under these conditions, also, a molecular ion corresponding to Ac-LWMR-OMe (reference numeral 33) was detected to indicate generation of oxazolone in the first process and liberation of the C-terminal amino acid in the second process.

Accordingly, the results of Example 6 to 29 are summarized as follows.

In the present invention, in order to analyze the amino acid sequence from the C-terminus, a combination of a series of the operations consisting of the following first to third processes and the operation of isolating and identifying the amino acid obtained was repeatedly carried out.

First Process

A protein or a peptide is allowed to react with an acid anhydride, the amino group of the protein or the peptide is protected, and the amino acid residue at the C-terminus is modified to generate oxazolone.

Second Process

The reaction product in the first process is allowed to react with an alcohol in the presence of acid, the oxazolone contained therein is subjected to alcoholysis (esterification), and the carboxy-terminal amino acid is liberated.

Third Process

The reaction product in the second process is allowed to react with an amine, the ester contained therein is hydrolyzed.

Hereinafter another procedure for carrying out the present invention will be further described.

EXAMPLE 30

Figure 36:
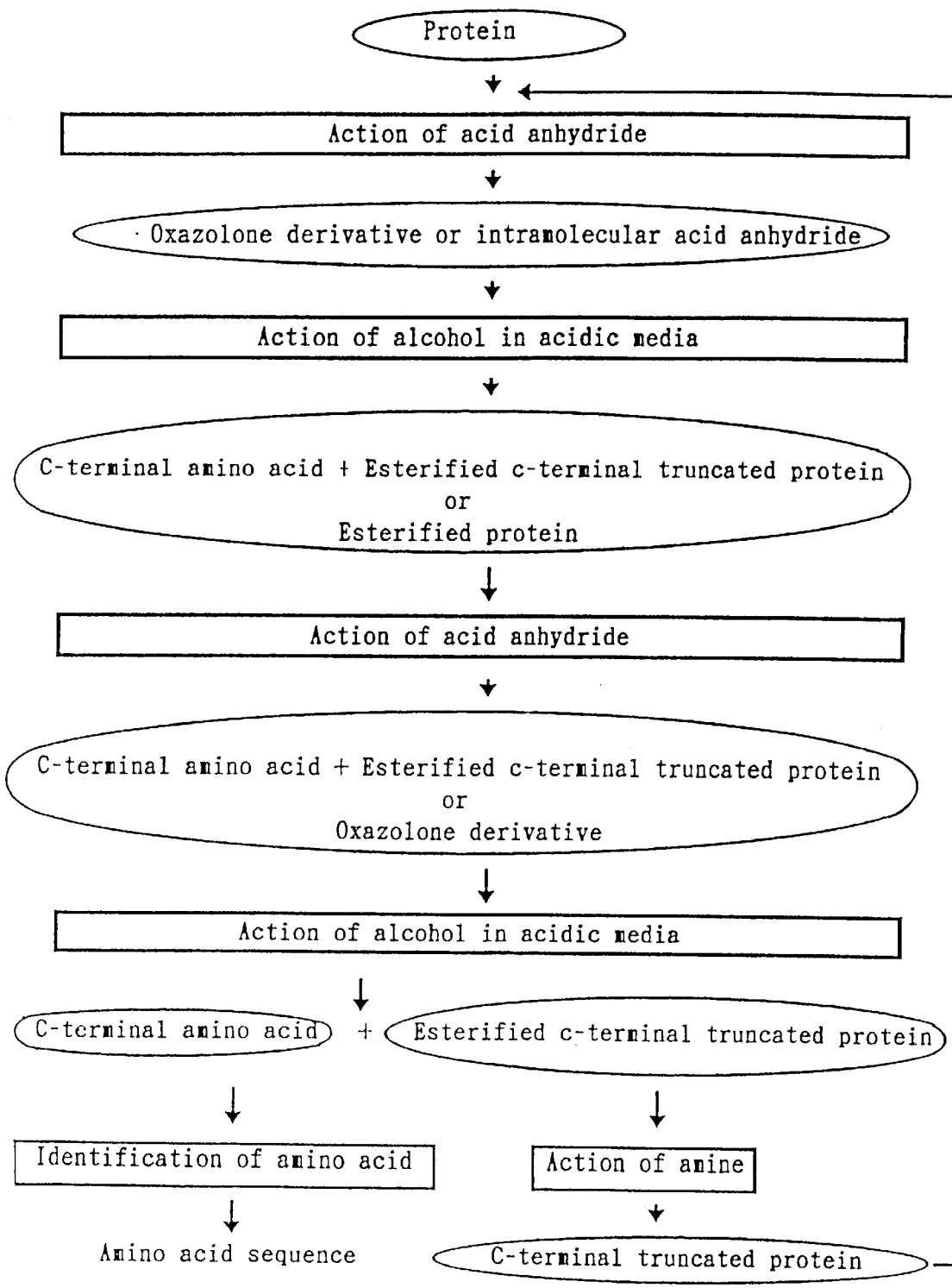
FIG. 36 shows a third flow chart representing a method for analyzing amino acid sequence of the present invention.

FIG. 36 shows a flow chart illustrating the present invention.

First Process

A protein or a peptide is allowed to react with an anhydride of an organic acid represented by the general formula;

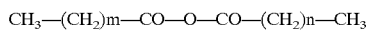

(m and n is an integer of 0 or above, respectively) to give a protein or a peptide of which the amino group is modified and C-terminal amino acid is converted into oxazolone or to give a protein or a peptide of which the amino group is acylated and the aspartic acid at the C-terminus is converted into an intramolecular acid anhydride when the C-terminal amino acid is aspartic acid.

Second Process

Then, the protein or the peptide of which the amino group is modified and C-terminal amino acid is converted into oxazolone or the protein or the peptide of which the amino group is acylated and the aspartic acid at the C-terminus is converted into an intramolecular acid anhydride is allowed to react with an alcohol in the presence of acid to give a mixture of a protein or a peptide newly generated of which the amino group is acylated, the C-terminal amino acid is lacking, and the carboxyl group of the C-terminal amino acid is esterified and the original C-terminal amino acid. At this time, the protein or the peptide of which the amino group is acylated and the aspartic acid at the C-terminus is converted into an intramolecular acid anhydride is converted into a protein or a peptide of which the amino group is acylated and the β-carboxyl group of the aspartic acid at the C-terminus is esterified.

Third Process

The mixture of a protein or a peptide newly generated, whose amino group is acylated, C-terminal amino acid is lacking, and carboxyl group of the C-terminal amino acid is esterified, and the original C-terminal amino acid, or the protein or the peptide, whose amino group is acylated, and β-carboxyl group of the aspartic acid at the C-terminus is esterified, is allowed to react with an anhydride of an organic acid represented by the general formula; $CH_3—(CH_2)_m—CO—O—CO—(CH_2)_n—CH_3$ (m and n is an integer of 0 or above, respectively). At this time, the protein or the peptide newly generated, whose amino group is modified, C-terminal amino acid is lacking, and carboxyl group of the C-terminal amino acid is esterified, is not affected at all. The original C-terminal amino acid is converted into an acylated amino acid derivative. On the other hand, the protein or the peptide, whose amino group is acylated and the β-carboxyl group of the aspartic acid at the C-terminus is esterified, is converted into a protein or a peptide, whose amino group is acylated, α-carboxyl group of the aspartic acid at the C-terminus is converted into oxazolone, and β-carboxyl group is esterified.

Fourth Process

Furthermore, the mixture of a protein or a peptide newly generated, whose amino group is acylated, C-terminal amino acid is lacking, and carboxyl group of the C-terminal amino acid is esterified, and the amino acid derivative, or the protein or the peptide, whose amino group is acylated, α-carboxyl group of the aspartic acid at the C-terminus is converted into oxazolone, and β-carboxyl group is esterified, is allowed to react with an alcohol in the presence of acid. At this time, the protein or the peptide newly generated, whose amino group is modified, C-terminal amino acid is lacking, and carboxyl group of the C-terminal amino acid is esterified, and the amino acid derivative are not affected at all. On the other hand, the protein or the peptide, whose amino group is modified, α-carboxyl group of the aspartic acid at the C-terminus is converted into oxazolone, and β-carboxyl group is esterified, is converted into a mixture of the protein or the peptide newly generated, whose amino group is modified, C-terminal amino acid is lacking, and carboxyl group of the C-terminal amino acid is esterified, and an aspartic acid whose β-carboxyl group is esterified.

Fifth Process

Then, the mixture of the protein or the peptide newly generated, whose amino group is modified, C-terminal amino acid is lacking, and carboxyl group of the C-terminal amino acid is esterified, and the amino acid derivative, or the mixture of the protein or the peptide newly generated, whose amino group is modified, C-terminal amino acid is lacking, and carboxyl group of the C-terminal amino acid is esterified, and the aspartic acid, whose β-carboxyl group is esterified, is allowed to react with an amine, for instance an amine represented by a general formula; NR1R2R3 to give a mixture of a protein or a peptide, whose amino acid is modified and C-terminal amino acid is lacking, and the amino acid derivative, or a mixture of a protein or a peptide, whose amino acid is modified and C-terminal amino acid is lacking, and aspartic acid. This aspartic acid is the original C-terminal amino acid.

The amino acid or amino acid derivative obtained in the first to fifth processes described above is isolated and identified to determine the C-terminal amino acid of the protein or the peptide.

Then a series of the operations of the first to fifth processes using the protein or the peptide, whose amino group is modified and C-terminal amino acid is lacking, and the operation of isolating and identifying the amino acid or amino acid derivative obtained is repeatedly carried out to analyze the amino acid sequence of the protein or the peptide from the C-terminus.

EXAMPLE 31

Figure 38:
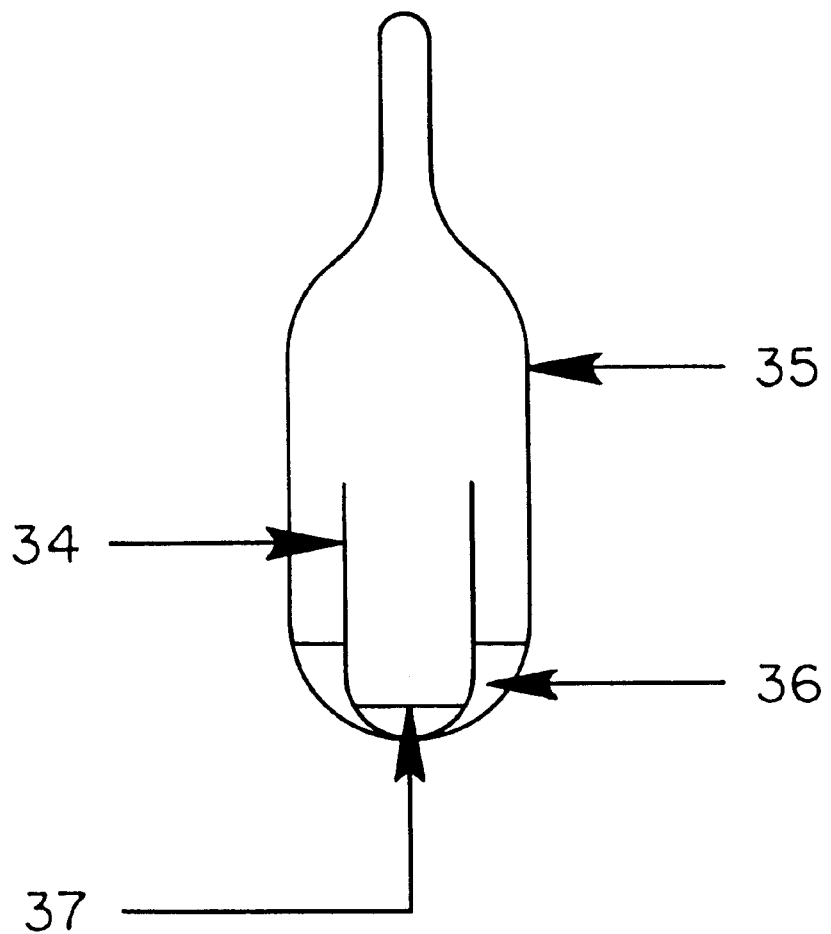
FIG. 38 shows a drawing illustrating another experimental procedure of the present invention.

Here, an example of the operation procedure of the present invention is described which analyzes an amino acid sequence of a protein or a peptide from a C-terminus thereof by repeating a series of the operations of the first to fifth processes using a protein or a peptide, an operation of isolating and identifying the amino acid from the mixture obtained in the second process, and an operation of isolating and identifying the amino acid from the mixture obtained in the fifth process. FIG. 37 shows a reaction scheme illustrating the experimental procedure of the present invention. FIG. 38 shows an experimental method of the present invention.

First Process

A sample is allowed to react with acetic anhydride. At first, a sample solution containing a protein or a peptide sample is placed into a small test tube 34 and dried. On the other hand, a solution of a reaction reagent (Here, an acetonitrile solution of acetic anhydride) 36 is placed into a test tube 35. The small test tube 34 having the sample 37 is placed into the test tube 35. This test tube 35 is sealed under reduced pressure with a vacuum pump, and the reaction proceeds.

The reaction conditions are as follows.

Reaction conditions

Concentration of acetic anhydride: 20% (acetonitrile solution)

Reaction temperature: 60° C.

Reaction period: 10 minutes

After this reaction, the top of the test tube 35 is opened and the small test tube 34 is taken out. Then the reaction mixture is evaporated under reduced pressure to dryness to remove the reagent and solvent.

Second Process

The sample obtained thereby is allowed to react with methanol in the presence of HFBA. The experimental procedure and apparatuses used for the reaction are the same as in the first process.

The reaction conditions are as follows.

Reaction conditions

Concentration of HFBA: 5% (methanol solution)

Reaction temperature: 5° C.

Reaction period: 30 minutes

After this reaction, the top of the test tube is opened and the small test tube is taken out. Then the reaction mixture is evaporated under reduced pressure to dryness to remove the reagent and solvent.

Third Process

The sample obtained thereby is allowed to react with acetic anhydride. The experimental procedure and apparatuses used for the reaction are the same as in the first process.

Fourth Process

The sample obtained thereby is allowed to react with methanol in the presence of HFBA. The experimental procedure and apparatuses used for the reaction are the same as in the second process.

Fifth Process

The sample obtained thereby is allowed to react with DMAE.

The experimental procedure and apparatuses used for the reaction follow in the first process. The solution placed into the test tube is an aqueous solution of DMAE.

The reaction conditions are as follows.

Reaction conditions

Concentration of DMAE: 50% (aqueous solution)

Reaction temperature: 50° C.

Reaction period: 30 minutes

In a series of these operations, after the second process, the amino acid is isolated from the sample obtained and identified. Furthermore, after the fifth process, the amino acid is isolated from the sample obtained and identified.

Then, a series of the procedures of the first to fifth processes using the protein or the peptide whose amino group is modified and C-terminal amino acid is lacking, the operation of isolating and identifying the amino acid obtained in the second process, the operation of isolating and identifying the amino acid obtained in the fifth process, and an operation of removing the residual amino acid and amino acid derivative are repeatedly carried out to analyze the amino acid sequence of the protein or the peptide from the C-terminus.

EXAMPLE 32

Here, an example of the operation procedure of the present invention is described which analyzes an amino acid sequence of a protein or a peptide from a C-terminus thereof by repeating a series of the operations of the first to fifth processes using a protein or a peptide and an operation of isolating and identifying the amino acid from the mixture obtained in the second process.

A series of the operations of the first to fifth processes is the same as in Example 31. In a series of these operations, after the second process, the amino acid is isolated from the sample obtained and identified. Furthermore, after the fifth process, the residual amino acid and amino acid derivative are removed. Then, a series of the procedures of the first to fifth processes using the protein or the peptide whose amino group is modified and C-terminal amino acid is lacking, the operation of isolating and identifying the amino acid obtained in the second process, and the operation of removing the residual amino acid and amino acid derivative are repeatedly carried out to analyze the amino acid sequence of the protein or the peptide from the C-terminus.

EXAMPLE 33

Here, an example of the operation procedure of the present invention is described which analyzes an amino acid sequence of a protein or a peptide from a C-terminus thereof by repeating a series of the operations of the first to fifth processes using a protein or a peptide and an operation of isolating and identifying the amino acid derivative from the mixture obtained in the third process.

A series of the operations of the first to fifth processes is the same as in Example 31. In a series of these operations, after the third process, the amino acid derivative is isolated from the sample obtained and identified. Furthermore, after the fifth process, the residual amino acid and amino acid derivative are removed. Then, a series of the procedures of the first to fifth processes using the protein or the peptide whose amino group is modified and C-terminal amino acid is lacking, the operation of isolating and identifying the amino acid derivative obtained in the third process, and the operation of removing the residual amino acid and amino acid derivative are repeatedly carried out to analyze the amino acid sequence of the protein or the peptide from the C-terminus.

EXAMPLE 34

Here, an example of the operation procedure of the present invention is described which analyzes an amino acid sequence of a protein or a peptide from a C-terminus thereof by repeating a series of the operations of the first to fifth processes using a protein or a peptide and an operation of isolating and identifying the amino acid derivative from the mixture obtained in the fourth process.

A series of the operations of the first to fifth processes is the same as in Example 31. In a series of these operations, after the fourth process, the amino acid derivative is isolated from the sample obtained and identified. Furthermore, after the fifth process, the residual amino acid and amino acid derivative are removed. Then, a series of the procedures of the first to fifth processes using the protein or the peptide, whose amino group is modified and C-terminal amino acid is lacking, the operation of isolating and identifying the amino acid derivative obtained in the fourth process, and the operation of removing the residual amino acid and amino acid derivative are repeatedly carried out to analyze the amino acid sequence of the protein or the peptide from the C-terminus.

EXAMPLE 35

Here, an example of the operation procedure of the present invention is described which analyzes an amino acid sequence of a protein or a peptide from a C-terminus thereof by repeating a series of the operations of the first to fifth processes using a protein or a peptide and an operation of isolating and identifying the amino acid and amino acid derivative from the mixture obtained in the fifth process.

A series of the operations of the first to fifth processes is the same as in Example 31. In a series of these operations, after the fifth process, the amino acid and amino acid derivative are isolated from the sample obtained and identified. Then, a series of the procedures of the first to fifth processes using the protein or the peptide whose amino group is modified and C-terminal amino acid is lacking, and the operation of isolating and identifying the amino acid and amino acid derivative obtained in the fifth process are repeatedly carried out to analyze the amino acid sequence of the protein or the peptide from the C-terminus.

EXAMPLE 36

Here, generation of oxazolone in the first process is described.

As the sample, a pentapeptide of Sequence No.3, leucyl-tryptophanylmethionylarginylphenylalanine (Leu-Trp-Met-Arg-Phe), was used.

The oxazolone was detected using the cleavage reaction easily caused by alcohol.

The sample obtained in the first process described in Example 31 was allowed to react with methanol.

Figure 39:
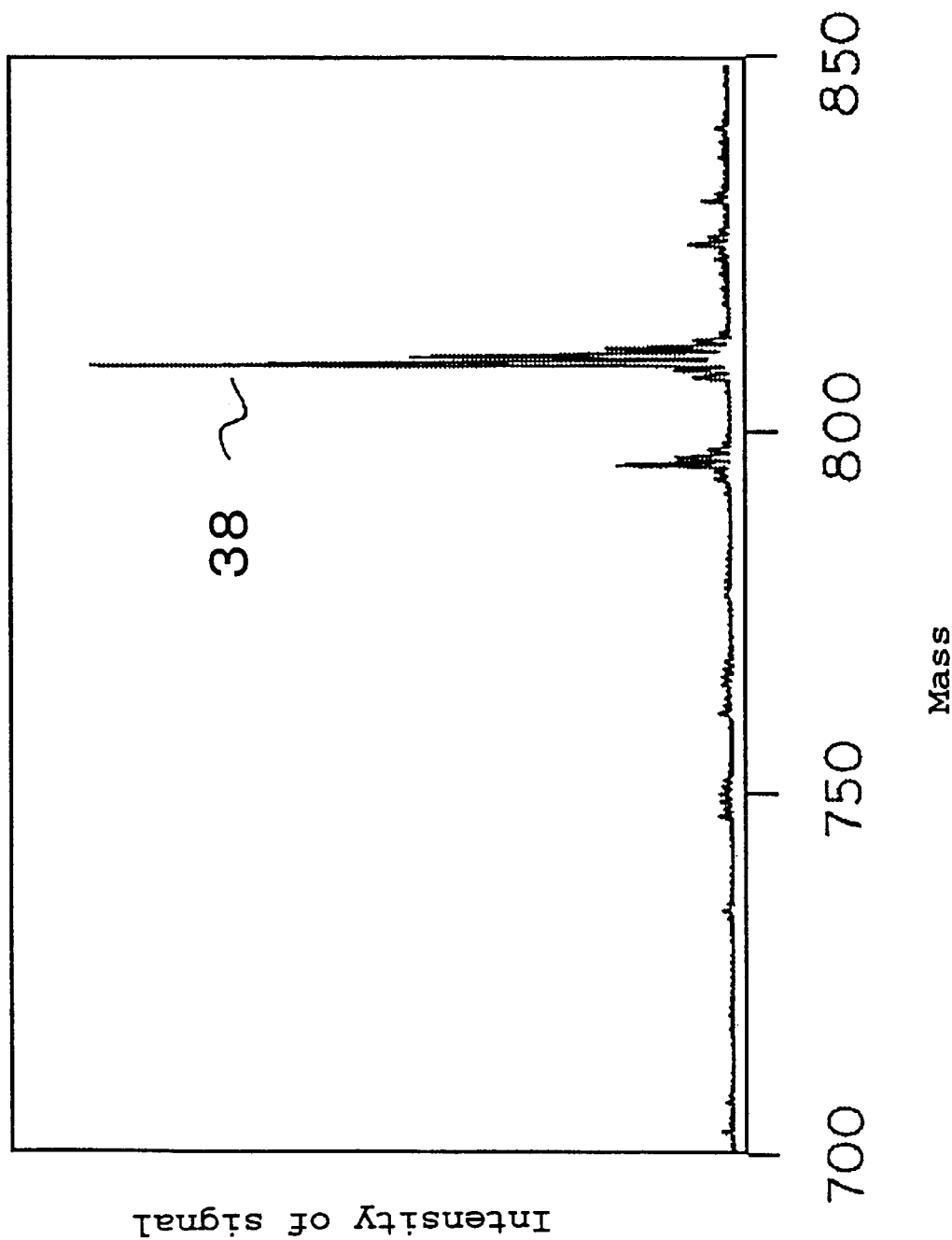
FIG. 39 shows a drawing showing a result of mass spectrometric analysis to confirm generation of oxazolone.

FIG. 39 shows a result of mass spectrometric analysis of the sample. The conditions of mass spectrometric analysis were as follows.

Conditions of mass spectrometric analysis
Analyzer: Double focusing mass spectrometer HX-110 (Nihon Denshi)

| Analysis conditions: | |
|---|---|
| Accelerating potential | 10 kV |
| Resolution | 1,000 |
| Ion source | FAB (fast-atom bombardment method) |
| Ionization gas | Xe |
| Ion mode | cationic |
| FAB gun accelerating potential | 6 kV |
| Detector | MULTIPLIER |
| Load potential | −20 kV |

Data processing system DA5000
Matrix
glycerol: thioglycerol:m-nitrobenzyl alcohol=1:1:1
Procedure for sample preparation
(1) Evaporate the sample under reduced pressure to dryness.
(2) Dissolve the residue in 67% acetic acid (or dimethylformamide) aqueous solution.
(3) Place the matrix of 1 µl on the target.
(4) Place the sample solution of 1 µl on the target and allow them to mix.
(5) Introduce the mixture into the ion source.

Here, a molecular ion (reference numeral 38) corresponding to the reaction product, whose amino terminus was acetylated and the carboxyl group at the C-terminus was esterified with a methyl group (the methyl ester of acetylleucyltriptophanylmethionylarginylphenylalanine, molecular weight of 808; hereinafter referred to as Ac-LWMRF-OMe) was detected to indicate existence of oxazolone in the sample obtained in the first process of Example 31.

EXAMPLE 37

Here, cleavage of the oxazolone ring in the second process is described.

As the sample, a pentapeptide of Sequence No.3, leucyl-tryptophanylmethionylarginylphenylalanine (Leu-Trp-Met-Arg-Phe), was used in the same manner as in Example 35.

Figure 40:
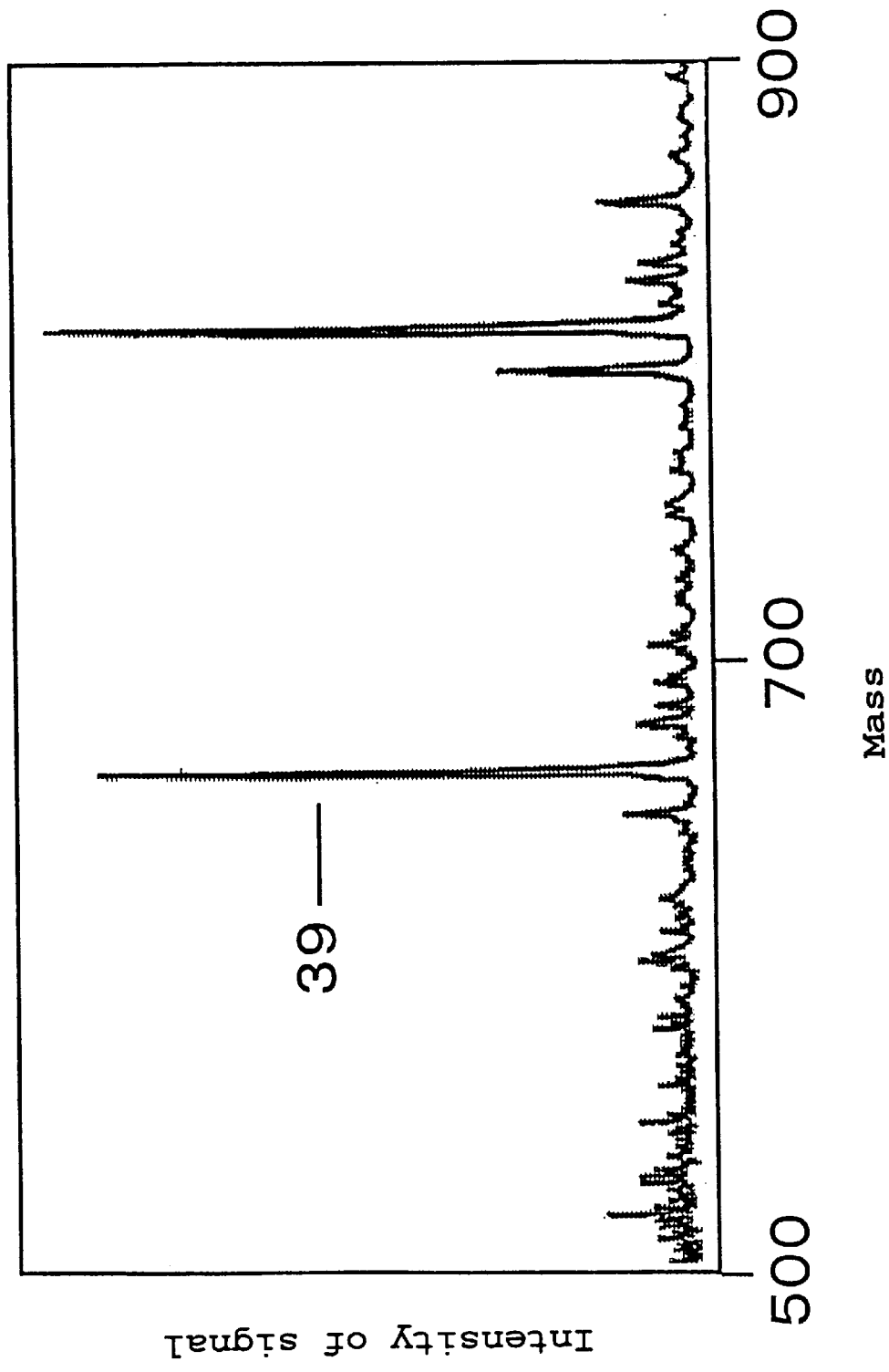
FIG. 40 shows a drawing showing a result of mass spectrometric analysis to confirm cleavage of the oxazolone ring.

FIG. 40 shows a result of mass spectrometric analysis of the sample obtained in the first and second processes described in Example 31. Here, the sample obtained in the first process was allowed to react with methanol in the presence of HFBA as the second process. The experimental procedure and apparatuses used for the reaction followed in the first process.

The reaction conditions were as follows.
Reaction conditions
Concentration of HFBA: 5% (methanol solution)
Reaction temperature: 25° C.
Reaction period: 30 minutes
The conditions for mass spectrometric analysis are the same as in Example 36.

A molecular ion (reference numeral 39) corresponding to the reaction product newly generated, whose amino terminus was acetylated, phenylalanine, C-terminal residue, was eliminated, and the carboxyl group at the C-terminus was esterified with a methyl group (Ac-LWMR-OMe, molecular weight of 661); hereinafter referred to as Ac-LWMRF-OMe) was detected to indicate cleavage of the oxazolone ring in the second process described in Example 2.

EXAMPLE 38

Here, cleavage of the oxazolone ring in the second process is described using a combination of HPLC and mass spectrometry.

Figure 41:
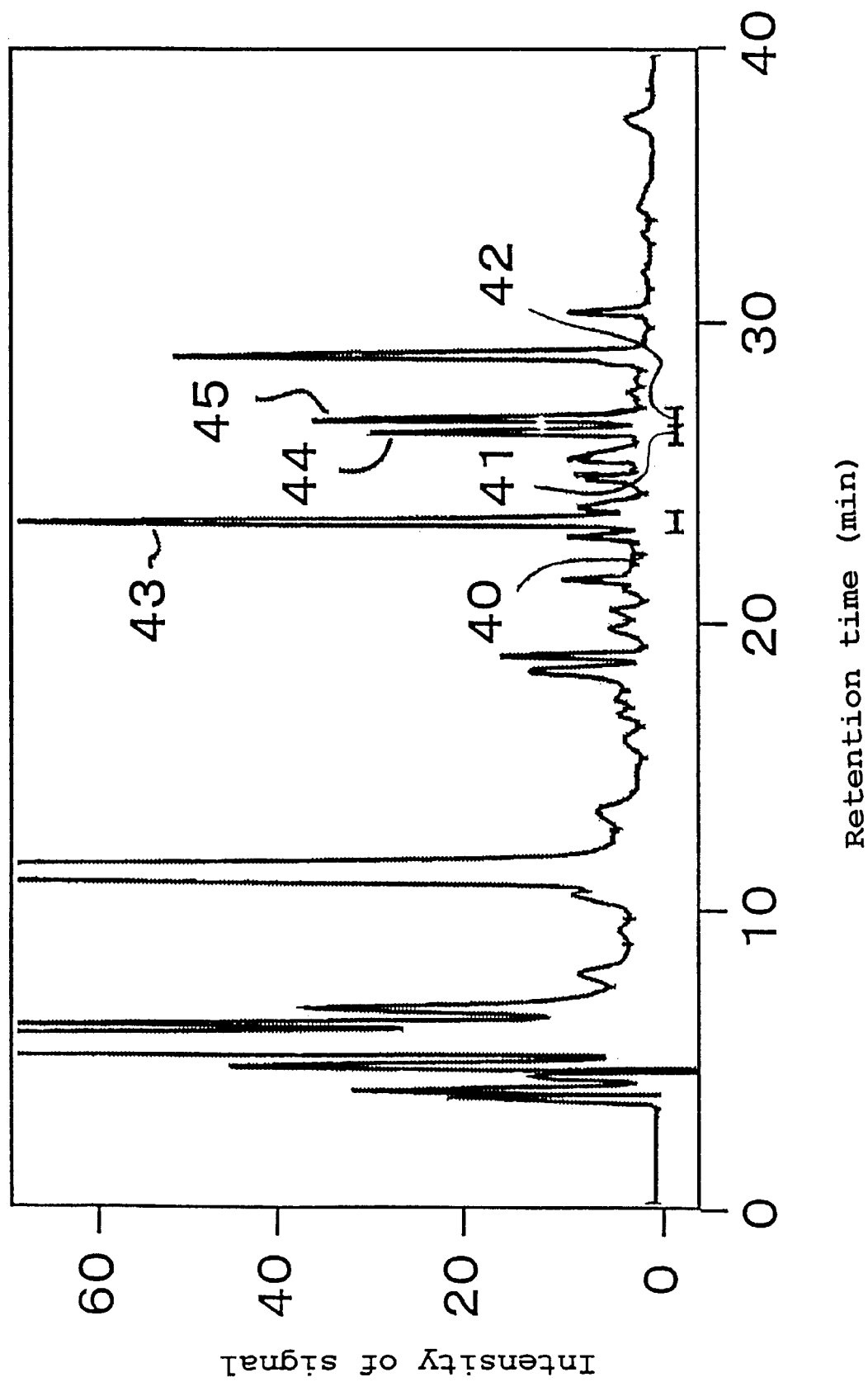
FIG. 41 shows a drawing showing a result of HPLC analysis to confirm cleavage of the oxazolone ring.

FIG. 41 shows a result of HPLC analysis of the reaction product obtained in the first and second processes described in Example 31. Here, the sample obtained in the first process was allowed to react with ethanol in the presence of HFBA as the second process.

The experimental procedure and apparatuses used for the reaction followed in the first process.

The reaction conditions were as follows.

Reaction conditions

Concentration of HFBA: 5% (ethanol solution)

Reaction temperature: 25° C.

Reaction period: 30 minutes

The conditions for HPLC analysis and procedure of preparing the sample were as follows.

Conditions for HPLC analysis

Analysis conditions

Column :C18 MICROBORE (Shiseido)

Elution conditions: Gradient elution with the following solution A and B.

Solution A: 0.1% TFA aqueous

Solution B: 80% acetonitrile aqueous containing 0.1% TFA

| Retention Time | Composition of Eluent |
| --- | --- |
| 0–5 min | Solution A, 80% |
| 5–25 min | Solution A, 80→40% (linear gradient) |
| 25–30 min | Solution A, 40% |

Preparation procedure of sample:

(1) Evaporate the sample under reduced pressure to dryness.

(2) Dissolve the residue in 0.1% TFA

Each peak was confirmed to correspond to each product as follows. Fraction 1 to 3 (corresponding to Reference numerals 40 to 42) in FIG. 41 was analyzed by mass spectrometry. The conditions for mass spectrometric analysis were as described in Example 36. In the figure, numeral 40 shows a fraction 1 separated by HPLC from the reaction product obtained in the first and second processes of Example 2. Numeral 41 shows a fraction 2 separated by HPLC from the reaction product obtained in the first and second processes of Example 2. Numeral 42 shows a fraction 3 separated by HPLC from the reaction product obtained in the first and second processes of Example 2. Numeral 43 shows a peak corresponding to the reaction product newly generated of the pentapeptide of Sequence No.3 of which the amino terminal amino acid is acetylated and the phenylalanine, the C-terminal residue, is eliminated, and the carboxyl group at the C-terminus is esterified with an ethyl group (molecular weight of 675). Numeral 44 shows a peak corresponding to the reaction product of the pentapeptide of Sequence No.3 of which the amino terminal amino acid is acetylated (molecular weight of 794). Numeral 45 shows a peak corresponding to the reaction product of the pentapeptide of Sequence No.3 of which the amino terminal amino acid is acetylated (molecular weight of 794).

Figure 42:
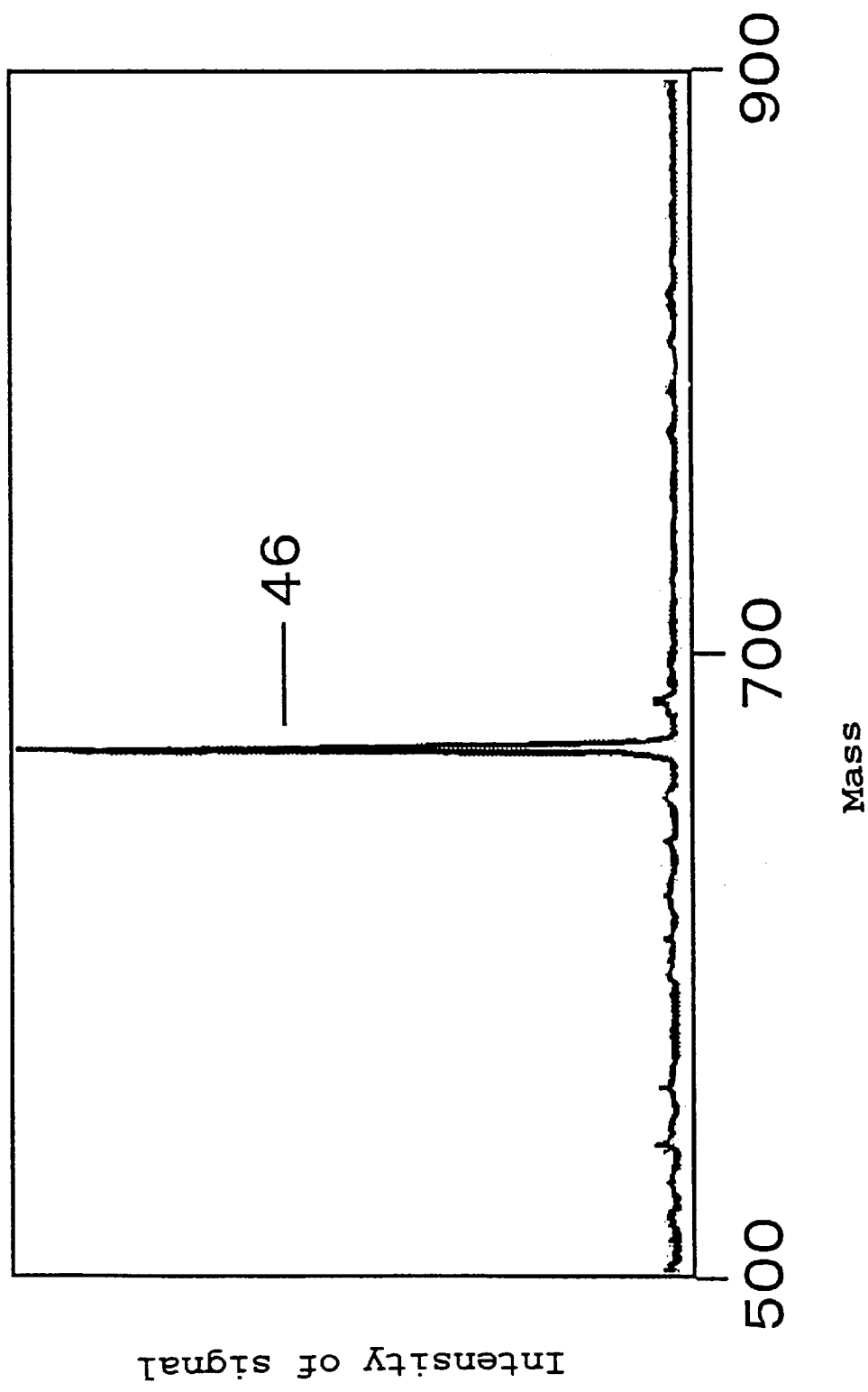
FIG. 42 shows a drawing showing a result of mass spectrometric analysis to confirm cleavage of the oxazolone ring of the product separated by HPLC.

FIG. 42 shows the result of Fraction 1 (Reference numeral 40). Here, Signal 46 from a molecular ion corresponding to the reaction product newly generated, whose amino terminal was acetylated, phenylalanine, C-terminal residue, was eliminated, and the carboxyl group at the C-terminus was esterified with an ethyl group (Ac-LWMR-OEt, molecular weight of 675) was detected. This result also indicates cleavage of the oxazolone ring in the second process of Example 31.

Figure 43:
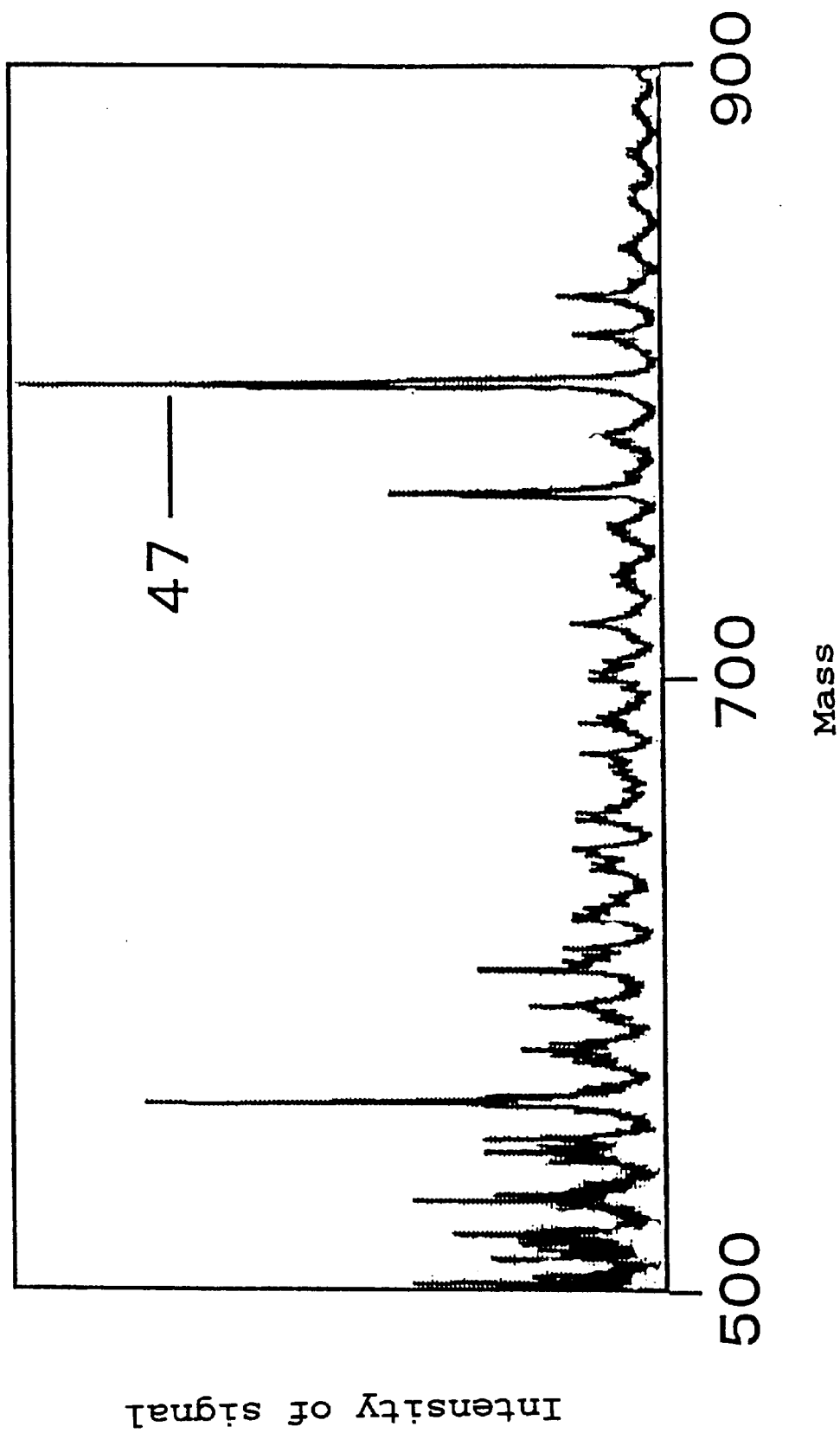
FIG. 43 shows a drawing showing a result of mass spectrometric analysis to confirm cleavage of the oxazolone ring of the product separated by HPLC.
Figure 44:
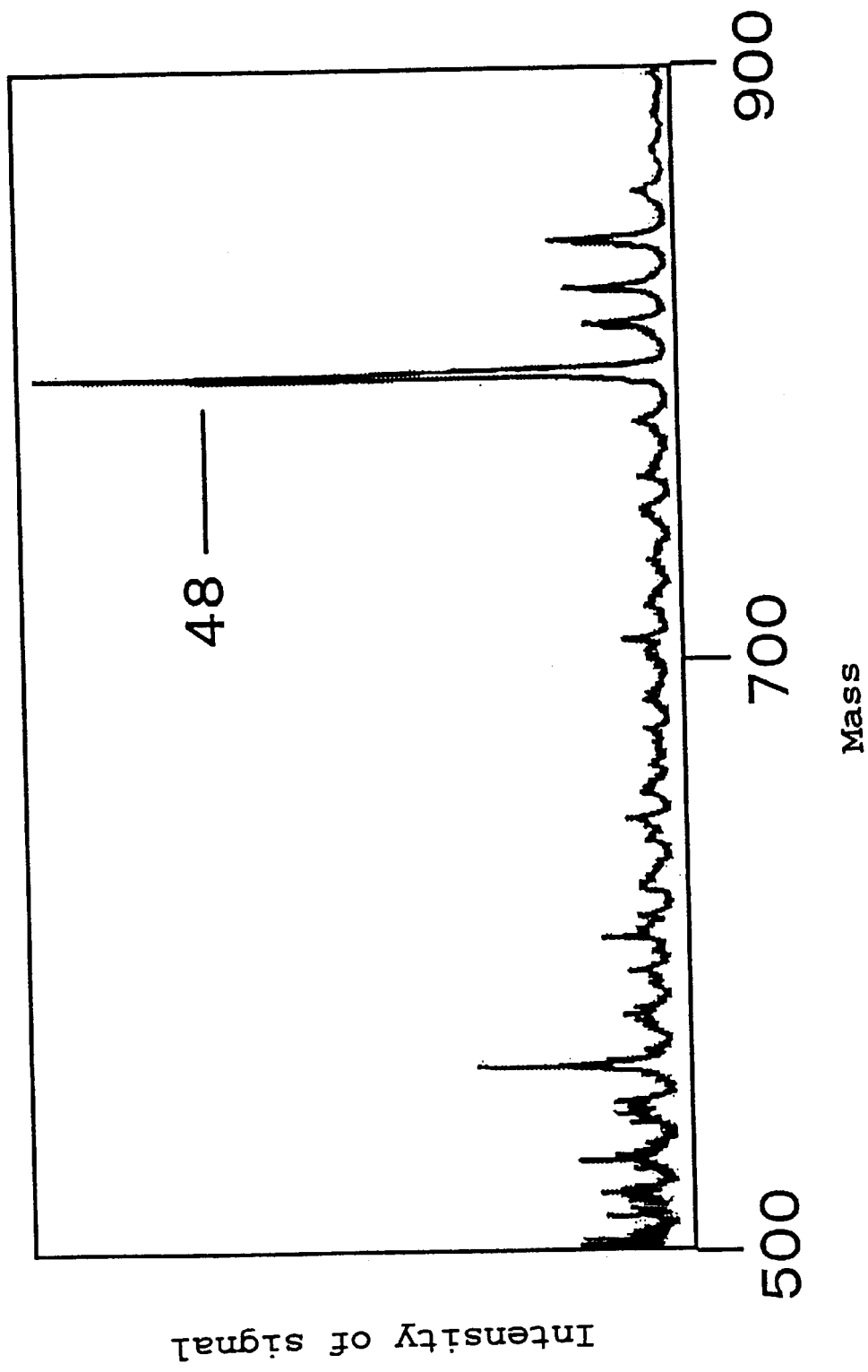
FIG. 44 shows a drawing showing a result of mass spectrometric analysis to confirm cleavage of the oxazolone ring of the product separated by HPLC.

FIG. 43 shows a result of mass spectrometric analysis of Fraction 2 (Reference numeral 41). FIG. 44 shows a result of mass spectrometric analysis of Fraction 3 (Reference numeral 42). In determination of these fractions, Signal 47 and 48 from molecular ions of the pentapeptide of Sequence No.3, whose amino terminal was acetylated (acetylleucyltriptophanylmethionylarginylphenylalanine, molecular weight of 794; hereinafter referred to as Ac-LWMRF-OH) was detected in each fraction. This seems to indicate racemization in generation of oxazolone in the first process. These results also indicate generation of an oxazolone ring in the first process and cleavage of the oxazolone ring in the second process.

EXAMPLE 39

Here, hydrolysis of the ester in the fifth process is described.

As the sample, a pentapeptide of Sequence No.3, leucyl-tryptophanylmethionylarginylphenylalanine (Leu-Trp-Met-Arg-Phe), was used in the same manner as in Example 36.

Figure 45:
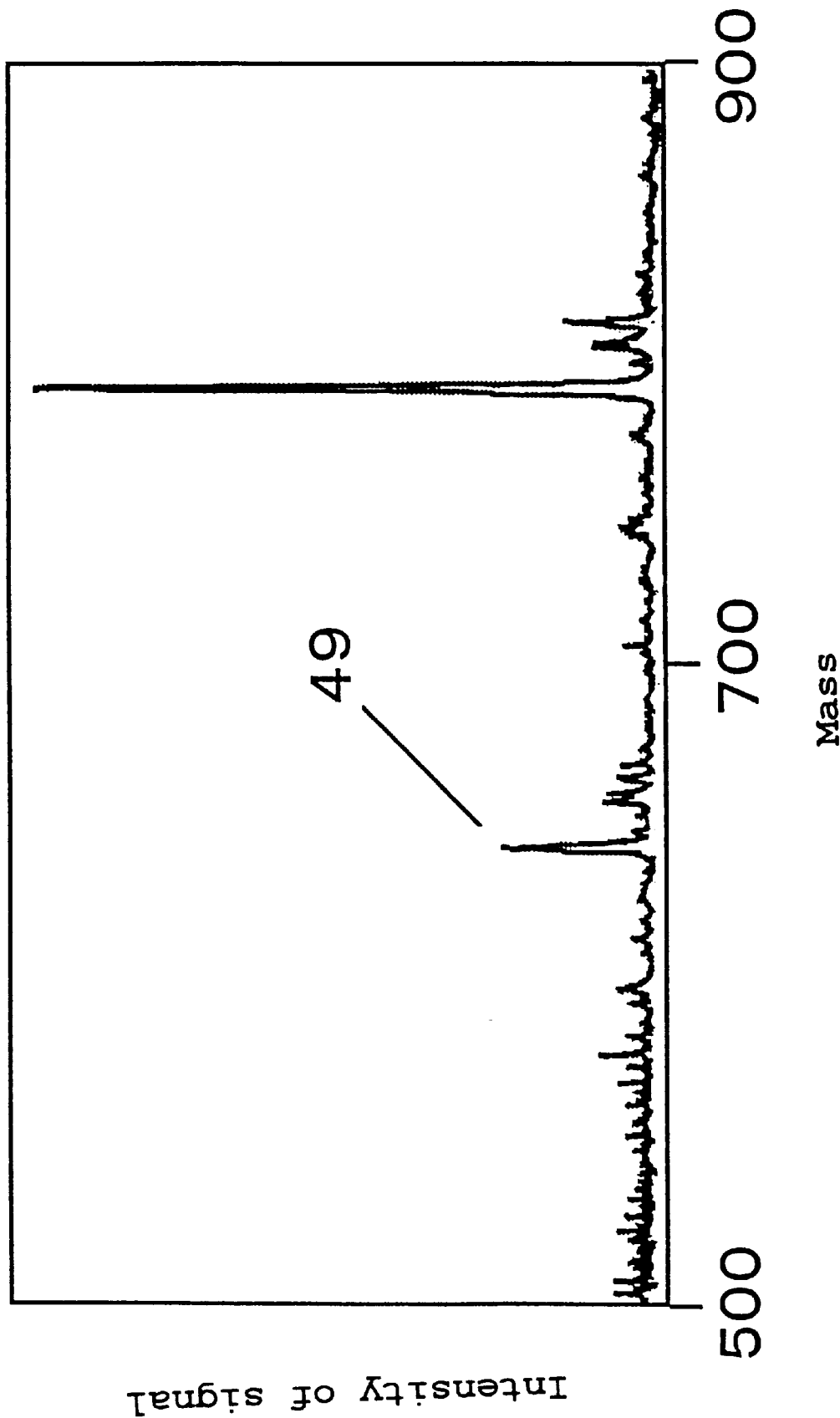
FIG. 45 shows a drawing showing a result of mass spectrometric analysis to confirm hydrolysis.

FIG. 45 shows a result of mass spectrometric analysis of the sample obtained in a series of the operations of the first to fifth processes described in Example 31. The conditions for mass spectrometric analysis were the same as in Example 36. Here, a molecular ion (reference numeral 49) corresponding to the reaction product newly generated, whose amino terminus was acetylated, the phenylalanine, the C-terminal residue, was eliminated, and the methyl ester of carboxyl group at the C-terminus was converted into a free carboxyl group (acetylleucyltriptophanylmethionylarginine, molecular weight of 647; hereinafter referred to as Ac-LWMR-OH) was detected to indicate hydrolysis of the ester in the fifth-process of Example 2.

Accordingly, the results of Example 30 to 39 are summarized as follows.

According to the present invention, in order to analyze the amino acid sequence from the C-terminus, a combination of a series of the operations consisting of the following first to fifth processes and the operation of isolating and identifying the amino acid or amino acid derivative obtained was repeatedly carried out.

First Process

A protein or a peptide is allowed to react with an acid anhydride, the amino terminal of the protein or the peptide is protected, and the amino acid residue at the C-terminus is modified to generate oxazolone or an intramolecular acid anhydride (when the C-terminal amino acid is aspartic acid).

Second Process

The reaction product in the first process is allowed to react with an alcohol in the presence of acid, the oxazolone contained therein is subjected to alcoholysis (esterification), and the carboxy-terminal amino acid is liberated or the intramolecular acid anhydride is ring-opened by alcoholysis.

Third Process

The reaction product in the second process is allowed to react with an acid anhydride, the amino acid residue at the C- terminus of the protein or the peptide, whose C-terminal is not blocked contained therein, is modified to generate oxazolone.

Fourth Process

The reaction product in the third process is allowed to react with an alcohol in the presence of acid, the oxazolone contained therein is subjected to alcoholysis (esterification), and the carboxy-terminal amino acid is liberated.

Fifth Process

The reaction product in the fourth process is allowed to react with an amine and the ester contained therein is hydrolyzed.

The present invention enables analysis of an amino acid sequence of a protein or a peptide from a C-terminus thereof without using enzymes by repeating a combination of a series of operations consisting of the processes described above and an operation of isolating and identifying the amino acid obtained, so that it prevents contamination by amino acids and peptides thereof by using enzymes and provides sequential determination which is suitable for microanalyses. Also the present invention provides cleavage of peptide bonds desired and accurate sequencing analysis.

What is claimed is:

1. In a method for amino acid sequencing of a protein or a peptide from a carboxy terminus thereof, carrying out a process comprising the steps of:

(1) modifying a carboxy-terminal amino acid of the protein or peptide by treating the protein or peptide with an acid anhydride having the general formula $CH_3-(CH_2)m-CO-O-CO-(CH_2)n-CH_3$, wherein m and n are integers of 0 or greater, which generates oxazolone at the carboxy terminus; and (2) liberating the modified carboxy-terminal amino acid and thereafter isolating and identifying the liberated amino acid or amino acid derivative.

2. In a method for amino acid sequencing of a protein or a peptide from a carboxy terminus thereof, carrying out a process comprising the steps of:

(1) modifying a carboxy-terminal amino acid of the protein or peptide by treating the protein or the peptide with an acid anhydride having the general formula $CH_3-(CH_2)m-CO-O-CO-(CH_2)n-CH_3$, wherein m and n are integers of 0 or greater, which protects the amino terminal and generates oxazolone at the carboxy terminus; and (2) liberating the modified carboxy-terminal amino acid and thereafter isolating and identifying the amino acid or amino acid derivative.

3. In a method for amino acid sequencing of a protein or a peptide from a carboxy terminus thereof, carrying out a process comprising the steps of:

(1) treating the protein or peptide with an acid anhydride to protect the amino terminal and to form oxazolone at the carboxy terminus;

(2) treating the protein or peptide having the carboxy terminus modified as oxazolone with an acid and an alcohol to liberate the carboxy-terminal amino acid; and (3) isolating and identifying the amino acid obtained in step (2).

4. A method for amino acid sequencing of a protein or a peptide from a carboxy terminus according to claim 3; wherein acetic acid is added to the reaction mixture in step (1).

5. In a method for amino acid sequencing of a protein or a peptide from a carboxy terminus thereof, carrying out a process comprising the steps of:

(1) treating the protein or peptide with an acid anhydride to protect the amino terminal and to form oxazolone at the carboxy terminus;

(2) treating the protein or peptide having the carboxy terminus modified as oxazolone with a solution containing an acid and an alcohol to liberate the carboxy-terminal amino acid; and (3) isolating and identifying the amino acid obtained in step (2).

6. A method for amino acid sequencing of a protein or a peptide from a carboxy terminus according to claim 5; wherein acetic acid is added to the reaction mixture in step (1).

7. In a method for amino acid sequencing of a protein or a peptide from a carboxy terminus thereof, carrying out a process comprising the steps of:

(1) treating the protein or peptide with an acid anhydride to protect the amino terminal and to form oxazolone at the carboxy terminus;

(2) treating the protein or peptide having the carboxy terminus modified as oxazolone with an ester to liberate the carboxy-terminal amino acid; and (3) isolating and identifying the amino acid obtained in step (2).

8. A method for amino acid sequencing of a protein or a peptide from a carboxy terminus according to claim 7; wherein acetic acid is added to the reaction mixture in step (1).

9. In a method for amino acid sequencing of a protein or a peptide from a carboxy terminus thereof, carrying out a process comprising the steps of:

(1) treating the protein or peptide with an acid anhydride to protect the amino terminal and to form oxazolone at the carboxy terminus;

(2) treating the protein or peptide having the carboxy terminus modified as oxazolone with an ester obtained from a solution containing an acid and an alcohol to liberate the carboxy-terminal amino acid; and (3) isolating and identifying the amino acid obtained in step (2).

10. A method for amino acid sequencing of a protein or a peptide from a carboxy terminus according to claim 9; wherein acetic acid is added to the reaction mixture in step (1).

11. In a method for amino acid sequencing of a protein or a peptide from a carboxy terminus thereof, carrying out a process comprising the steps of:

(1) treating the protein or peptide with an acid anhydride to protect the amino terminal and to form oxazolone at the carboxy terminus;

(2) treating the protein or peptide having the carboxy terminus modified as oxazolone with an alcohol to liberate the carboxy-terminus amino acid;

(3) treating the protein or peptide having the truncated carboxy terminus with an amine to hydrolyze an ester; and (4) isolating and identifying the amino acid obtained in step (2).

12. A method for amino acid sequencing of a protein or a peptide from a carboxy terminus according to claim 11; wherein acetic acid is added to the reaction mixture in step (1).

13. A method for amino acid sequencing of a protein or a peptide from a carboxy terminus according to claim 11; wherein step (2) is carried out in the presence of an acid.

14. A method for amino acid sequencing of a protein or a peptide from a carboxy terminus according to claim 11; wherein acetic acid is added to the reaction mixture in step (1), and the step of treating with an alcohol to liberate the carboxy-terminal amino acid is carried out in the presence of an acid.

15. In a method for amino acid sequencing of a protein or a peptide from a carboxy terminus thereof, carrying out a process comprising the steps of:

(1) treating the protein or peptide with an acid anhydride to protect the amino terminal and to form oxazolone at the carboxy terminus;

(2) treating the protein or peptide having the carboxy terminus modified as oxazolone with an alcohol to liberate the carboxy-terminal amino acid;

(3) treating the protein or peptide having the truncated carboxy terminus with an amine to hydrolyze an ester; and (4) isolating and identifying the amino acid obtained after performing step (3).

16. A method for amino acid sequencing of a protein or a peptide from a carboxy terminus according to claim 15; wherein acetic acid is added to the reaction mixture in step (1).

17. A method for amino acid sequencing of a protein or a peptide from a carboxy terminus according to claim 15; wherein step (2) is carried out in the presence of an acid.

18. A method for amino acid sequencing of a protein or a peptide from a carboxy terminus according to claim 15; wherein acetic acid is added to the reaction mixture in step (1), and the step of treating with an alcohol to liberate the carboxy-terminal amino acid is carried out in the presence of an acid.

19. In a method for amino acid sequencing of a protein or a peptide from a carboxy terminus thereof, carrying out a process comprising the steps of:

(1) treating the protein or peptide with an acid anhydride to protect the amino terminal and to form oxazolone at the carboxy terminus;

(2) treating the protein or peptide having the carboxy terminus modified as oxazolone with an alcohol to liberate the carboxy-terminal amino acid;

(3) treating the protein or peptide having the truncated carboxy terminus with an aqueous solution of an amine to hydrolyze an ester; and (4) isolating and identifying the amino acid obtained in step (2).

20. A method for amino acid sequencing of a protein or a peptide from a carboxy terminus according to claim 19; wherein acetic acid is added to the reaction mixture in step (1).

21. A method for amino acid sequencing of a protein or a peptide from a carboxy terminus according to claim 19; wherein step (2) is carried out in the presence of an acid.

22. A method for amino acid sequencing of a protein or a peptide from a carboxy terminus according to claim 19; wherein acetic acid is added to the reaction mixture in step (1), and the step of treating with an alcohol to liberate the carboxy-terminal amino acid is carried out in the presence of an acid.

23. In a method for amino acid sequencing of a protein or a peptide from a carboxy terminus thereof, carrying out a process comprising the steps of:

(1) treating the protein or peptide with an acid anhydride to protect the amino terminal and to form oxazolone at the carboxy terminus;

(2) treating the protein or peptide having the carboxy terminus modified as oxazolone with an alcohol to liberate the carboxy-terminal amino acid;

(3) treating the protein or peptide having the truncated carboxy terminus with an aqueous solution of an amine to hydrolyze an ester; and (4) isolating and identifying the amino acid obtained after performing step (3).

24. A method for amino acid sequencing of a protein or a peptide from a carboxy terminus according to claim 23; wherein acetic acid is added to the reaction mixture in step (1).

25. A method for amino acid sequencing of a protein or a peptide from a carboxy terminus according to claim 23; wherein step (2) is carried out in the presence of an acid.

26. A method for amino acid sequencing of a protein or a peptide from a carboxy terminus according to claim 23; wherein acetic acid is added to the reaction mixture in step (1), and the step of treating with an alcohol to liberate the carboxy-terminal amino acid is carried out in the presence of an acid.

27. In a method for amino acid sequencing of a protein or a peptide from a carboxy terminus thereof, carrying out a process comprising the steps of:

(1) treating the protein or peptide with an acid anhydride to protect an amino group, to form an oxazolone at the carboxy terminus when the carboxy-terminal amino acid is not aspartic acid, and to form an intramolecular acid anhydride at the carboxy terminus when the carboxy-terminal amino acid is aspartic acid;

(2) treating the protein or peptide with an alcohol to liberate the carboxy-terminal amino acid when the carboxy terminal is oxazolone and to alcoholize the intramolecular acid anhydride when the carboxy terminal is an intramolecular acid anhydride;

(3) treating the protein or peptide with an acid anhydride to form oxazolone at the carboxy terminal at the carboxy terminus when the carboxy-terminal amino acid was aspartic acid;

(4) treating the protein or peptide with an alcohol to liberate the carboxy-terminal amino acid;

(5) treating the reaction mixture with an amine to hydrolyze the ester; and (6) isolating and identifying the amino acid obtained in step (2), and isolating and identifying the amino acid obtained in step (5).

28. A method for amino acid sequencing of a protein or a peptide from a carboxy terminus according to claim 27; wherein the step (2) and step (4) are carried out in the presence of an acid.

29. In a method for amino acid sequencing of a protein or a peptide from a carboxy terminus thereof, carrying out a process comprising the steps of:

(1) treating the protein or peptide with an acid anhydride to protect an amino group, to form an oxazolone at the carboxy terminus when the carboxy-terminal amino acid is not aspartic acid, and to form an intramolecular acid anhydride at the carboxy terminus when the carboxy-terminal amino acid is aspartic acid;

(2) treating the protein or peptide with an alcohol to liberate the carboxy-terminal amino acid when the carboxy terminal is oxazolone and to alcoholize the intramolecular acid anhydride when the carboxy terminal is an intramolecular acid anhydride;

(3) treating the protein or peptide with an acid anhydride to form oxazolone at the carboxy terminal at the carboxy terminus when the carboxy-terminal amino acid was aspartic acid;

(4) treating the protein or peptide with an alcohol to liberate the carboxy-terminal amino acid;

(5) treating the reaction mixture with an amine to hydrolyze the ester; and (6) isolating and identifying the amino acid obtained in step (2).

30. A method for amino acid sequencing of a protein or a peptide from a carboxy terminus according to claim 29; wherein the step (2) and step (4) are carried out in the presence of an acid.

31. In a method for amino acid sequencing of a protein or a peptide from a carboxy terminus thereof, carrying out a process comprising the steps of:

(1) treating the protein or peptide with an acid anhydride to protect an amino group, to form an oxazolone at the carboxy terminus when the carboxy-terminal amino acid is not aspartic acid, and to form an intramolecular acid anhydride at the carboxy terminus when the carboxy-terminal amino acid is aspartic acid;

(2) treating the protein or peptide with an alcohol to liberate the carboxy-terminal amino acid when the carboxy terminal is oxazolone and to alcoholize the intramolecular acid anhydride when the carboxy terminal is an intramolecular acid anhydride;

(3) treating the protein or peptide with an acid anhydride to form oxazolone at the carboxy terminal at the carboxy terminus when the carboxy-terminal amino acid was aspartic acid;

(4) treating the protein or peptide with an alcohol to liberate the carboxy-terminal amino acid;

(5) treating the reaction mixture with an amine to hydrolyze the ester; and (6) isolating and identifying the amino acid obtained in step (2).

32. A method for amino acid sequencing of a protein or a peptide from a carboxy terminus according to claim 31;

wherein the step (2) and step (4) are carried out in the presence of an acid.

33. In a method for amino acid sequencing of a protein or a peptide from a carboxy terminus thereof, carrying out a process comprising the steps of:
   (1) treating the protein or peptide with an acid anhydride to protect an amino group, to form an oxazolone at the carboxy terminus when the carboxy-terminal amino acid is not aspartic acid, and to form an intramolecular acid anhydride at the carboxy terminus when the carboxy-terminal amino acid is aspartic acid;
   (2) treating the protein or peptide with an alcohol to liberate the carboxy-terminal amino acid when the carboxy terminal is oxazolone and to alcoholize the intramolecular acid anhydride when the carboxy terminal is an intramolecular acid anhydride;
   (3) treating the protein or peptide with an acid anhydride to form oxazolone at the carboxy terminal at the carboxy terminus when the carboxy-terminal amino acid was aspartic acid;
   (4) treating the protein or peptide with an alcohol to liberate the carboxy-terminal amino acid;
   (5) treating the reaction mixture with an amine to hydrolyze the ester; and
   (6) isolating and identifying the amino acid obtained in step (4).

34. A method for amino acid sequencing of a protein or a peptide from a carboxy terminus according to claim 23; wherein the step (2) and step (4) are carried out in the presence of an acid.

35. In a method for amino acid sequencing of a protein or a peptide from a carboxy terminus thereof, carrying out a process comprising the steps of:
   (1) treating the protein or peptide with an acid anhydride to protect an amino group, to form an oxazolone at the carboxy terminus when the carboxy-terminal amino acid is not aspartic acid, and to form an intramolecular acid anhydride at the carboxy terminus when the carboxy-terminal amino acid is aspartic acid;
   (2) treating the protein or peptide with an alcohol to liberate the carboxy-terminal amino acid when the carboxy terminal is oxazolone and to alcoholize the intramolecular acid anhydride when the carboxy terminal is an intramolecular acid anhydride;
   (3) treating the protein or peptide with an acid anhydride to form oxazolone at the carboxy terminal at the carboxy terminus when the carboxy-terminal amino acid was aspartic acid;
   (4) treating the protein or peptide with an alcohol to liberate the carboxy-terminal amino acid;
   (5) treating the reaction mixture with an amine to hydrolyze the ester; and
   (6) isolating and identifying the amino acid obtained in step (5).

36. A method for amino acid sequencing of a protein or a peptide from a carboxy terminus according to claim 35; wherein the step (2) and step (4) are carried out in the presence of an acid.

37. In a method for amino acid sequencing of a protein or a peptide from a carboxy terminus thereof, carrying out a process comprising the steps of:
   (1) treating the protein or peptide with an acid anhydride to protect an amino group, to form an oxazolone at the carboxy terminus when the carboxy-terminal amino acid is not aspartic acid, and to form an intramolecular acid anhydride at the carboxy terminus when the carboxy-terminal amino acid is aspartic acid;
   (2) treating the protein or peptide with an alcohol to liberate the carboxy-terminal amino acid when the carboxy terminal is oxazolone and to alcoholize the intramolecular acid anhydride when the carboxy terminal is an intramolecular acid anhydride;
   (3) treating the protein or peptide with an acid anhydride to form oxazolone at the carboxy terminal at the carboxy terminus when the carboxy-terminal amino acid was aspartic acid;
   (4) treating the protein or peptide with an alcohol to liberate the carboxy-terminal amino acid;
   (5) treating the reaction mixture with an amine to hydrolyze the ester; and
   (6) isolating and identifying the amino acid obtained in step (2) and isolating and identifying the amino acid obtained in step (5).

38. A method for amino acid sequencing of a protein or a peptide from a carboxy terminus according to claim 37; wherein the step (2) and step (4) are carried out in the presence of an acid.

39. In a method for amino acid sequencing of a protein or a peptide from a carboxy terminus thereof, carrying out a process comprising the steps of:
   (1) treating the protein or peptide with an ester of a halogenated formic acid to protect an amino group, to form an oxazolone at the carboxy terminus when the carboxy-terminal amino acid is not aspartic acid, and to form an intramolecular acid anhydride at the carboxy terminus when the carboxy-terminal amino acid is aspartic acid;
   (2) treating the protein or peptide with an alcohol to liberate the carboxy-terminal amino acid when the carboxy terminal is oxazolone and to alcoholize the intramolecular acid anhydride when the carboxy terminal is an intramolecular acid anhydride;
   (3) treating the protein or peptide with an ester of halogenated formic acid to form oxazolone at the carboxy terminal at the carboxy terminus when the carboxy-terminal amino acid was aspartic acid;
   (4) treating the protein or peptide with an alcohol to liberate the carboxy-terminal amino acid;
   (5) treating the reaction mixture with an amine to hydrolyze the ester; and
   (6) isolating and identifying the amino acid obtained in step (2).

40. A method for amino acid sequencing of a protein or a peptide from a carboxy terminus according to claim 39; wherein the step (2) and step (4) are carried out in the presence of an acid.

41. In a method for amino acid sequencing of a protein or a peptide from a carboxy terminus thereof, carrying out a process comprising the steps of:
   (1) treating the protein or peptide with an ester of a halogenated formic acid to protect an amino group, to form an oxazolone at the carboxy terminus when the carboxy-terminal amino acid is not aspartic acid, and to form an intramolecular acid anhydride at the carboxy terminus when the carboxy-terminal amino acid is aspartic acid;
   (2) treating the protein or peptide with an alcohol to liberate the carboxy-terminal amino acid when the carboxy terminal is oxazolone and to alcoholize the intramolecular acid anhydride when the carboxy terminal is an intramolecular acid anhydride;

(3) treating the protein or peptide with an ester of halogenated formic acid to form oxazolone at the carboxy terminal at the carboxy terminus when the carboxy-terminal amino acid was aspartic acid;

(4) treating the protein or peptide with an alcohol to liberate the carboxy-terminal amino acid;

(5) treating the reaction mixture with an amine to hydrolyze the ester; and (6) isolating and identifying the amino acid obtained in step (3).

42. A method for amino acid sequencing of a protein or a peptide from a carboxy terminus according to claim 41; wherein the step (2) and step (4) are carried out in the presence of an acid.

43. In a method for amino acid sequencing of a protein or a peptide from a carboxy terminus thereof, carrying out a process comprising the steps of:

(1) treating the protein or peptide with an ester of a halogenated formic acid to protect an amino group, to form an oxazolone at the carboxy terminus when the carboxy-terminal amino acid is not aspartic acid, and to form an intramolecular acid anhydride at the carboxy terminus when the carboxy-terminal amino acid is aspartic acid;

(2) treating the protein or peptide with an alcohol to liberate the carboxy-terminal amino acid when the carboxy terminal is oxazolone and to alcoholize the intramolecular acid anhydride when the carboxy terminal is an intramolecular acid anhydride;

(3) treating the protein or peptide with an ester of halogenated formic acid to form oxazolone at the carboxy terminal at the carboxy terminus when the carboxy-terminal amino acid was aspartic acid;

(4) treating the protein or peptide with an alcohol to liberate the carboxy-terminal amino acid;

(5) treating the reaction mixture with an amine to hydrolyze the ester; and (6) isolating and identifying the amino acid obtained in step (4).

44. A method for amino acid sequencing of a protein or a peptide from a carboxy terminus according to claim 43; wherein the step (2) and step (4) are carried out in the presence of an acid.

45. In a method for amino acid sequencing of a protein or a peptide from a carboxy terminus thereof, carrying out a process comprising the steps of:

(1) treating the protein or peptide with an ester of a halogenated formic acid to protect an amino group, to form an oxazolone at the carboxy terminus when the carboxy-terminal amino acid is not aspartic acid, and to form an intramolecular acid anhydride at the carboxy terminus when the carboxy-terminal amino acid is aspartic acid;

(2) treating the protein or peptide with an alcohol to liberate the carboxy-terminal amino acid when the carboxy terminal is oxazolone and to alcoholize the intramolecular acid anhydride when the carboxy terminal is an intramolecular acid anhydride;

(3) treating the protein or peptide with an ester of halogenated formic acid to form oxazolone at the carboxy terminal at the carboxy terminus when the carboxy-terminal amino acid was aspartic acid;

(4) treating the protein or peptide with an alcohol to liberate the carboxy-terminal amino acid;

(5) treating the reaction mixture with an amine to hydrolyze the ester; and (6) isolating and identifying the amino acid obtained in step (5).

46. A method for amino acid sequencing of a protein or a peptide from a carboxy terminus according to claim 45; wherein the step (2) and step (4) are carried out in the presence of an acid.

\* \* \* \* \*

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 5
      (B) TYPE: amino acid
      (C) STRANDEDNESS: Not Applicable
      (D) TOPOLOGY: linear (ii) MOLECULE TYPE: peptide (xi) SEQUENCE DESCRIPTION: SEQ ID NO:1:

Ala Trp Met Arg Phe
1               5

(2) INFORMATION FOR SEQ ID NO:2:

(i) SEQUENCE CHARACTERISTICS:
      (A) LENGTH: 6
      (B) TYPE: amino acid
      (C) STRANDEDNESS: Not Applicable
      (D) TOPOLOGY: linear (ii) MOLECULE TYPE: peptide (xi) SEQUENCE DESCRIPTION: SEQ ID NO:2:

Ala Trp Met Arg Phe Ala
1               5

(2) INFORMATION FOR SEQ ID NO:3:

(i) SEQUENCE CHARACTERISTICS:
      (A) LENGTH: 5
      (B) TYPE: amino acid
      (C) STRANDEDNESS: Not Applicable
      (D) TOPOLOGY: linear (ii) MOLECULE TYPE: peptide (xi) SEQUENCE DESCRIPTION: SEQ ID NO:3:

Leu Trp Met Arg Phe
1               5